US008101189B2

(12) United States Patent
Leclerc et al.

(10) Patent No.: US 8,101,189 B2
(45) Date of Patent: *Jan. 24, 2012

(54) VACCINES AND IMMUNOPOTENTIATING COMPOSITIONS AND METHODS FOR MAKING AND USING THEM

(75) Inventors: Denis Leclerc, Fossambault sur le Lac (CA); Nathalie Majeau, Fossambault sur le Lac (CA); Constantino III Roberto Lopez-Macias, Mexico City (MX); Alain Lamarre, Laval (CA)

(73) Assignee: Folia Biotech Inc., Quebec, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/556,678

(22) Filed: Nov. 3, 2006

(65) Prior Publication Data

US 2007/0166322 A1 Jul. 19, 2007

Related U.S. Application Data

(63) Continuation-in-part of application No. 10/609,417, filed on Jul. 1, 2003, now Pat. No. 7,641,896.

(60) Provisional application No. 60/393,659, filed on Jul. 5, 2002, provisional application No. 60/732,659, filed on Nov. 3, 2005.

(51) Int. Cl.
  *A61K 35/00* (2006.01)
  *C12N 15/00* (2006.01)
(52) U.S. Cl. ............... 424/216.1; 424/201.1; 424/202.2; 435/5; 435/69.1; 435/69.7
(58) Field of Classification Search .................. None
  See application file for complete search history.

(56) References Cited

U.S. PATENT DOCUMENTS

| 5,420,026 | A  | 5/1995  | Payne |
| 5,443,969 | A  | 8/1995  | Wilson |
| 5,958,422 | A  | 9/1999  | Lomonossoff |
| 5,977,438 | A  | 11/1999 | Turpen et al. |
| 6,042,832 | A  | 3/2000  | Koprowski et al. |
| 6,232,099 | B1 | 5/2001  | Chapman et al. |
| 6,544,779 | B1 | 4/2003  | Cichutek et al. |
| 6,627,202 | B2 | 9/2003  | Murray |
| 7,018,826 | B1 | 3/2006  | Hildt et al. |
| 7,641,896 | B2 | 1/2010  | Leclerc et al. |
| 2003/0202982 | A1 | 10/2003 | Birkett |
| 2005/0048082 | A1 | 3/2005  | Leclerc et al. |
| 2009/0280145 | A1 | 11/2009 | Leclerc et al. |
| 2010/0047264 | A1 | 2/2010  | Leclerc |
| 2010/0111996 | A1 | 5/2010  | Leclerc |
| 2010/0316665 | A1 | 12/2010 | Leclerc et al. |

FOREIGN PATENT DOCUMENTS

| EP | 0 445 625 | 9/1991 |
| EP | 1 006 123 | 6/2000 |
| EP | 1 167 530 | 1/2002 |
| WO | WO-87/01386 | 3/1987 |
| WO | WO-92/03537 | 3/1992 |
| WO | WO-96/12027 | 4/1996 |
| WO | WO-97/39134 | 10/1997 |
| WO | WO-98/08375 | 3/1998 |
| WO | 98/50071 A1 | 11/1998 |
| WO | WO-99/18220 | 4/1999 |
| WO | WO-99/28488 | 6/1999 |
| WO | WO-99/50424 | 10/1999 |
| WO | WO-00/06717 | 2/2000 |
| WO | WO-00/46376 | 8/2000 |
| WO | WO-01/18199 | 3/2001 |
| WO | WO-01/26682 | 4/2001 |
| WO | WO-01/27282 | 4/2001 |
| WO | WO-01/66778 | 9/2001 |
| WO | WO-01/73078 | 10/2001 |
| WO | WO-02/00169 | 1/2002 |
| WO | WO-02/04007 | 1/2002 |
| WO | WO-02/102410 | 12/2002 |
| WO | WO-2004/004761 | 1/2004 |
| WO | 2005055957 A2 | 6/2005 |
| WO | WO-2008/058369 | 5/2008 |
| WO | WO-2008/058396 | 5/2008 |
| WO | WO2008089569 A1 | 7/2008 |

OTHER PUBLICATIONS

Tang et al., (Recent advances in DNA vaccine of hepatitis virus, Hepatobiliary & Pancreatic Dis. Inter., 2002, vol. 1, p. 228-231.*
Machuca et al. Intervirology 1999, vol. 42 p. 37-42.*
Letvin, 2006, Nature Immunology, vol. 6, p. 930-939.*
Jager et al. (Clinical Cancer Vaccine Trials, Current Opinion in Immunology, 2002, vol. 14, p. 178-182.*
Short et al. (Virology, 1986, vol. 152, p. 280-283).*
Sit et al. (Journal of General Virology, 1989, vol. 70, p. 2325-2331).*
Sit et al. Journal of General Virology, 1993, vol. 74, p. 1133-1140.*
Abouhaidar, J. Gen. Virol. (1988) 69:219-226.
Abouhaidar et al., J. Gen. Virol. (1989) 70:1871-1875.
Abouhaidar et al., Virology (1978) 90(1):54-59.
Bigras et al., *Maturation and diversification of antiviral B cell repertoires*, CIHR Institute of Infection and Immunity New Investigator Forum (poster presentation), Apr. 15-17, 2005, Prague, Czech Republic.
Canizares et al., Cell Biol. (2005) 83(3):263-270.

(Continued)

*Primary Examiner* — Agnieszka Boesen
(74) *Attorney, Agent, or Firm* — Gavrilovich, Dodd & Lindsey; Gregory P. Einhorn

(57) ABSTRACT

An immunopotentiating composition comprising a papaya mosaic virus (PapMV), or a virus-like particle (VLP) derived from PapMV coat protein, which is capable of functioning as an adjuvant and thus potentiating an immune response in an animal is provided. The immunopotentiating composition can further comprise an immunogen, which can be fused or otherwise linked to the VLP, or not linked to the VLP. The immunopotentiating composition is capable of potentiating a humoral and/or a cellular response in the animal and is suitable for use as an adjuvant or vaccine. Methods of potentiating an immune response in an animal comprising administering to the animal an immunopotentiating composition are also provided have application in both human and veterinary medicine.

44 Claims, 31 Drawing Sheets

OTHER PUBLICATIONS

Denis et al., The adjuvant effect of the Papaya Mosaic Virus vaccine platform in explained by the multimerization of the nucleocapsid carrier protein, Immunology conference (poster presentation), Jun. 8-10, 2005, Radisson SAS Hotel, Prague, Czech Republic.
Denis et al., *The plant potexvirus Papaya Mosaic Virus triggers a strong immune response in mice*, International Congress on Immunology (poster presentation), Jul. 18-23, 2004, Montreal, Quebec, Canada.
Guang-Shu et al., Heilongjiang Agriculture Science (2001) 1:44-47 (Full article: Chinese; Relevant portion: English).
Lacasse et al., *Evaluation du potential vaccinal de pseudoparticules dur virus de la mosaique de la papaye exprimant des epitopes etrangers*, Immunology conference (abstract and slide presentation), Nov. 5, 2005, Auberge du Lac-a-l'Eau-Claire, Quebec, Canada (English translation included).
Leclerc, Development of a papaya mosaic virus vaccination platform, Immunology conference (slide presentation), Jun. 8-10, 2005, Radisson SAS Hotel, Prague, Czech Republic.
Lecours et al., Protein Expression and Purification (2006) 47:273-280.
Martinez et al., Virology (2003) 305(2):428-435.
Moron et al., Journal of Immunol. (2003) 171:2242-2250.
Ruedl et al., Eur. J. Immunol. (2002) 32(3):818-825.
Stubbs, Phil. Trans. R. Soc. Lond. (1999) 354:551-557.
Tremblay et al., *Assembly and RNA-binding activity of mutated recombinant Papaya Mosaic Virus capsid proteins*, American Society of Virology Conference (slide presentation), Jul. 10, 2004, McGill University, Montreal, Quebec, Canada.
Tremblay et al., FEBS Journal (2006) 273:14-25.
Wong et al., J. Virol. (2001) 75(3):1229-1235.
Zhang et al., J. Mol. Biol. (1993) 234(3):885-887.
Restriction Requirement for U.S. Patent Publication No. 2005/0048082, mailed on Mar. 8, 2005.
Restriction Requirement for U.S. Patent Publication No. 2005/0048082, mailed on Sep. 12, 2005.
Non-Final Office Action for U.S. Patent Publication No. 2005/0048082, mailed on Dec. 20, 2005.
Final Office Action for U.S. Patent Publication No. 2005/0048082, mailed on Sep. 6, 2006.
Non-Final Office Action for U.S. Patent Publication No. 2005/0048082, mailed on Apr. 2, 2007.
Non-Final Office Action for U.S. Patent Publication No. 2005/0048082, mailed on Sep. 11, 2007.
U.S. Appl. No. 10/609,417, filed Jul. 1, 2003.
Bach, Endocrine Reviews (1994) 15(4):516-542.
Bachmann et al., Science (1993) 262:1448-1451.
Bachmann et al., Immunology Today (1996) 17(12):553-557.
Baratova et al., Virology (1992) 188:175-180.
Belanger et al., The FASEB Journal (2000) 14:2323-2328.
Blanco et al., Scand. J. Infect. Dis. (1993) 25:73-80.
Brennan et al., Journal of Virology (1999) 73(2):930-938.
Brennan et al., Molec. Biot. (2001) 17:15-26.
Chiu et al., The Lancet (1999) 354:2002.
Cohen, Science (1999) 285:26-30.
Cooke et al., Nature Immunol. (2001) 2(9):810-815.
Cruz et al., PNAS USA (1996) 93:6286-6290.
Cryz, Vaccine (1999) 17:S1-S5.
Dalsgaard et al., Nature Biotech. (1997) 15:248-252.
Daniel et al., PNAS USA (1996) 93:956-960.
Gajewski et al., J. Exp. Med. (1994) 179:481-491.
Gonzalez et al., Microbiol. Immunol. (1993) 37(10):793-799.
Gonzalez et al., Arch. Med. Res. (1995) 26:S99-S103.
Grinna et al., Yeast (1989) 5:107-115.
Igietseme et al., Exp. Rev. Vaccines (2004) 3(1):23-34.
Ikegami, "Papaya Mosaic Potexvirus as an Expression Vector for Foreign Peptides" M.S. Thesis, Botany, Univ. of Toronto (1995).
Isibasi et al., Vaccine (1992) 10(12):811-813.
Isibasi et al., Infect. Immun. (1988) 56(11):2953-2959.
Isibasi et al., Ann. NY Acad. Sci. (1994) 730:350-352.
Kawamura et al., J. Immunol. (1986) 136(1):58-65.
Koprowski et al., Vaccine (2001) 19:2735-2741.
Kratz, PNAS USA (1999) 96:1915-1920.
Leclerc et al., JBC (1998) 273(4):29015-29021.
Leclerc et al., Journal of Virology (1999) 73:553-560.
Leclerc et al., Virus Genes (2001) 22(2):159-165.
Lee-Shanok, "Construction and Preliminary Characterization of Papaya Mosaic Virus as an Expression Vector for the Presentation of Foreign Epitopes" M.S. Thesis, Univ. of Toronto (1999) p. 1-108.
Levine et al., Vaccine (1999) 17:S22-S27.
Lopez-Marcias et al., NY Acad. Sci. (1995) 772:285-288.
Makino et al., Exp. Anim. (1980) 29:1-3.
Maldonaldo et al., Arch. Med. Res. (2000) 31:S71-S73.
Marusic et al., J. of Virology (2001) 75(18):8434-8439.
Medzhitov et al., Seminars in Immunology (2000) 12:185-188.
Netter et al., Journal of Virology (2001) 75(5):2130-2141.
Pang et al., Trends Microbiol. (1998) 6:131-133.
Parriagua-Solis et al., Immunol. Infect. Dis. (1995) 5:244-249.
Plotkin et al., Arch. Intern. Med. (1995) 155:2293-2299.
Porta et al., Reviews in Medical Virology (1998) 8:25-41.
Robins et al., J. Infect. Dis. (1984) 150(3):436-449.
Roit, Essential Immunology, Oxford/Blackwell, London, 7th ed. (1991) pp. 65-83.
Saier, Mol. Microbiol. (2000) 35(4):699-710.
Savory et al., (1995) 615-634.
Schultz, Curr. Opin. Cell. Biol. (1993) 5:701-707.
Scorer et al., Gene (1993) 136:111-119.
Scott et al., Science (1990) 249(4967):386-390.
Sedlik, J. Virology (2000) P5769-5775.
Simone et al., Diabetes Care (1999) 22(Suppl. 2):B7-B15.
Sit et al., J. Gen. Virol. (1993) 74:1133-1140.
Sit et al., J. Gen. Virol. (1989) 70:2325-2331.
Storni, J. Immunology (2002) 168:2880-2886.
Taylor et al., Science (1999) 285:107-109.
Terskikh et al., PNAS USA (1997) 94:1663-1668.
Tian et al., Nat. Med. (1996) 2(12):1348-1353.
Tschopp et al., Bio/technology (1987) 5:1305-1308.
Turpen et al., Bio/technology (1995) 13:53-57.
Usha et al., Virology (1993) 197:366-374.
Wong et al., J. Virol. (2001) 75:1229-1235.
Ikegami et al., Canadian Journal of Plant Pathology (1996) 18(1):92.
Short et al., Virology (1986) 152:280-283.
Anindya and Savithri, Virology (2003) 316(2):325-336.
Antonis et al., Vaccine (2006) 24:5481-5490.
Ault, Obstet Gynecol Surv (2006) 61:S26-S31.
Biosgerault et al., J Immunol (2005) 174:3432-3439.
Fagan et al., J Med Virol (1987) 21:49-56.
Harper et al., Lancet (2004) 364:1757-1765.
Ionescu et al., J Pharm Sci (2006) 95:70-79.
Maurer et al., Eur J Immunol (2005) 35:2031-2040.
Mihailova et al., Vaccine (2006) 4369-4377.
Non-Final Office Action for U.S. Appl. No. 10/609,417, mailed on Apr. 24, 2008.
Notice of Allowance for U.S. Appl. No. 10/609,417, mailed on Jul. 9, 2009.
Ogasawara et al., In Vivo (2006) 20:319-324.
Pumpens et al., Intervirology (2002) 45:24-32.
Saini and Vrati, J Virol (2003) 77:3487-3494.
Stills, Harold F. Jr. (2005) Adjuvants and Antibody Production: Dispelling the Myths Associated with Freund's Complete and Other Adjuvants. ILAR Journal vol. 46, No. 3, pp. 280-293.
Boesen, Agnieszka. U.S.Non-Final Office Action, date of mailing of report Apr. 1, 2010, U.S. Appl. No. 12/384,476.
Boesen, Agnieszka. U.S. Final Office Action, date of mailing of report Oct. 13, 2010, U.S. Appl. No. 12/384,476.
Brennan, et al., "A Chimaeric Plant Virus Vaccine Protects Mice Against a Bacterial Infection", Microbiology, 1999, vol. 145, pp. 2061-2067.
Chackerian, et al. (2001) "Conjugation of a Self-antigen to Papillomavirus-like Particles Allows for efficient Induction of Protective Autoantibodies", Journal of Clinical Investigation, 108(3):415-23.
Grgacic, et al. (2006) "Virus-Like Particles: Passport to Immune Recognition", Methods 40(1): 60-5.
Jegerlehner, et al. (2002) "A Molecular Assembly System that Renders Antigens of Choice Highly Repetitive for Induction of Protective B cell Responses", Vaccine, Aug. 19; 20(25-26):3104-12.

Lagging, et al. (1995) "Immune Responses to Plasmid DNA Encoding the Hepititis C Virus Core Protein", Journal of Virology 69(9):5859-5863.

Murthy, et al., "Similarities in the Genomic Sequence and Coat Protein Structure of Plant Viruses, Porc. Int. Symp. Bioml. Struct. Interactions", Suppl. J. Biosci, 1985, vol. 8, No. 3&4, pp. 815-821.

Stills, (2005) "Adjuvant and Antibody Production", ILAR Journal, vol. 46, No. 3, pp. 280-293.

Boesen, Agnieszka, USPTO U.S.Non-Final Office Action, date of mailing of report Jun. 1, 2011, U.S. Appl. No. 12/384,476.

EPO Communication pursuant to Article 93(3) EPC; Oct. 5, 2011; EPO.

Erickson, et al. (1978) The Self-Assembly of Papaya Mosaic Virus; Virology 90:36-46.

Extended European Search Report, Oct. 17, 2011; EPO.

Japan patent office office action (Notification of Reason(s) for Refusal Summarized); Nov. 8, 2011, JPTO.

* cited by examiner

A
M 1 2 3 4 5 6 7 8 9 10
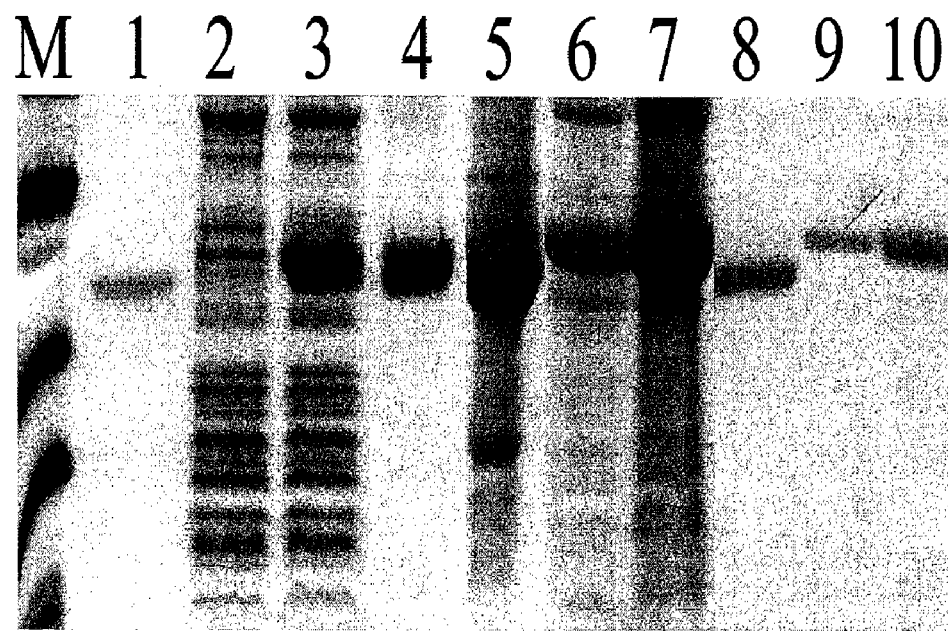
B
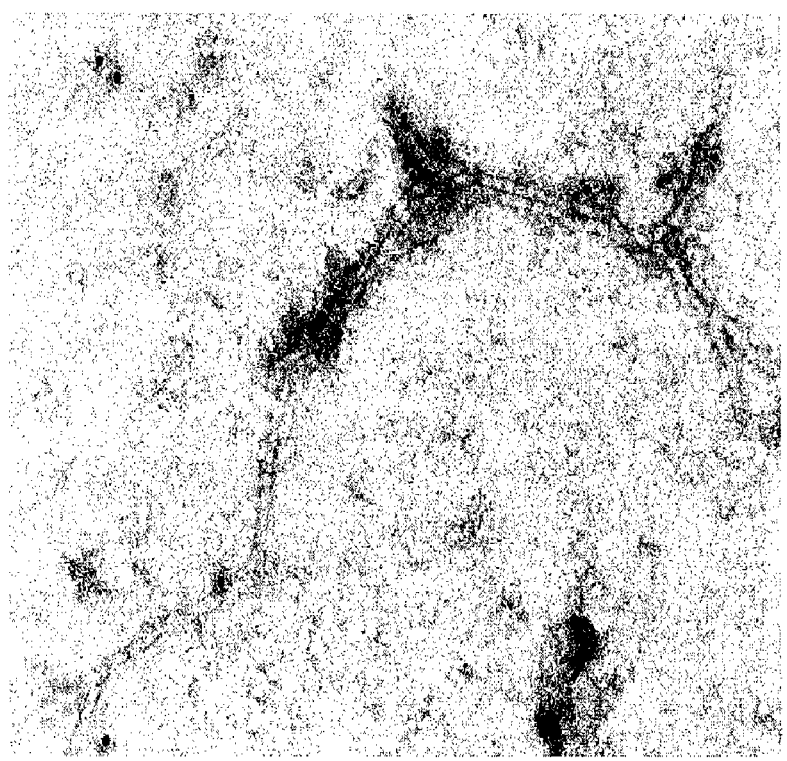
FIGURE 1

A
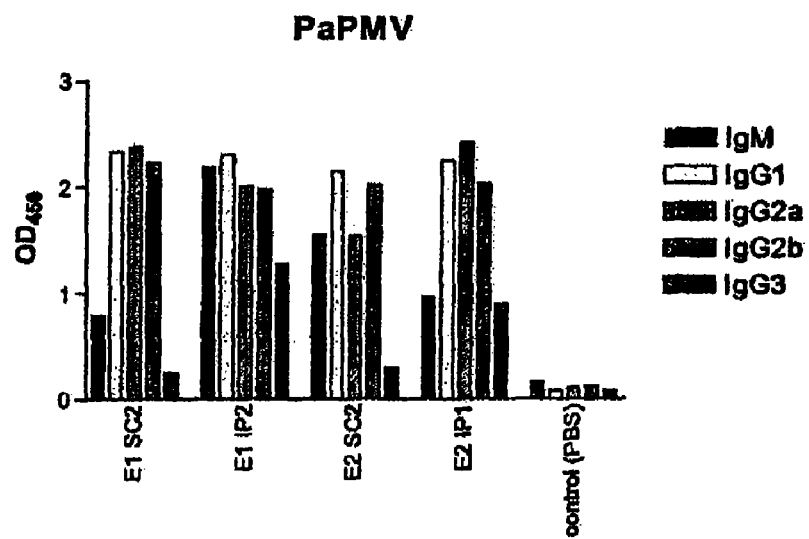
B
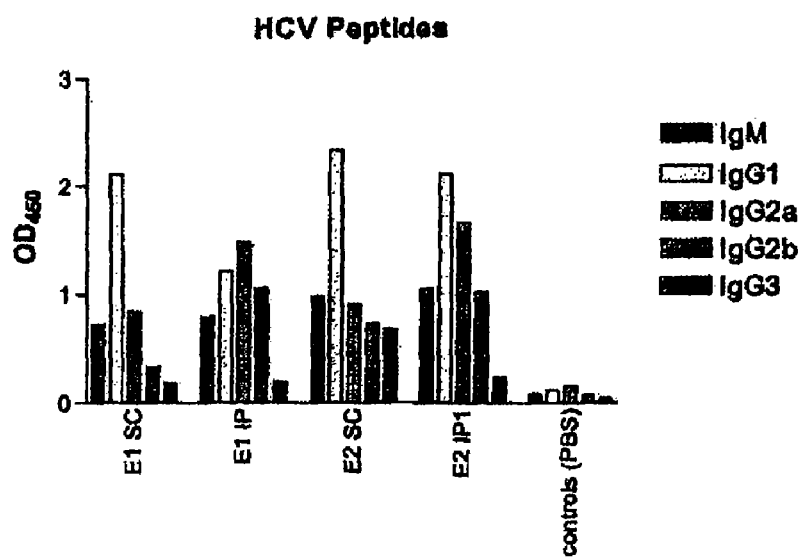
FIGURE 7

A.
>gi|9629172|ref|NP_044334.1| capsid protein [Papaya mosaic virus]
MSKSSMSTPNIAFPAITQEQMSSIKVDPTSNLLPSQEQLKSVSTLMVAAKVPAASVTTVA
LELVNFCYDNGSSAYTTVTGPSSIPEISLAQLASIVKASGTSLRKFCRYFAPIIWNLRTDK
MAPANWEASGYKPSAKFAAFDFFDGVENPAAMQPPSGLIRSPTQEERIANATNKQVHLF
QAAAQDNNFTSNSAFITKGQISGSTPTIQFLPPPE

B.
ATGTCTAAGTCAAGTATGTCCACACCCAACATAGCCTTCCCCGCCATCACCCAGGAA
CAGATGAGCTCGATTAAGGTCGATCCAACGTCCAATCTTCTGCCCTCCCAAGAGCAG
TTAAAGTCAGTGTCCACCCTCATGGTAGCTGCTAAGGTTCCAGCAGCCAGTGTTACA
ACTGTGGCATTGGAGTTGGTCAACTTCTGCTATGACAATGGGTCCAGCGCGTACACC
ACAGTGACTGGCCCATCATCAATACCGGAGATATCACTGGCACAATTGGCTAGTATT
GTCAAAGCTTCCGGCACTTCCCTTAGAAAATTCTGCCGGTACTTCGCGCCAATAATC
TGGAATCTGAGGACGGACAAAATGGCTCCTGCCAATTGGGAGGCTTCAGGATACAA
GCCAAGCGCCAAATTTGCCGCGTTCGACTTCTTCGACGGGGTGGAGAATCCGGCGG
CCATGCAACCCCCTTCGGGACTAATCAGGTCGCCGACCCAGGAAGAGCGGATTGCC
AATGCTACCAACAAACAGGTGCATCTCTTCCAAGCCGCGGCACAGGACAACAACTT
TACCAGCAACTCCGCCTTCATCACCAAAGGCCAAATTTCTGGGTCAACCCCAACCAT
CCAATTCCTTCCACCCCCCGAATAA

C.
MASTPNIAFP AITQEQMSSI KVDPTSNLLP SQEQLKSVST LMVAAKVPAA
SVTTVALELV NFCYDNGSSA YTTVTGPSSI PEISLAQLAS IVKASGTSLR KFCRYFAPII
WNLRTDKMAP ANWEASGYKP SAKFAAFDFF DGVENPAAMQ PPSGLTRSPT
QEERIANATN KQVHLFQAAA QDNNFASNSA FITKGQISGS TPTIQFLPPP E

```
              203
PapMV    .QFLPPPETS .............TTRHHHHHH
PapMV-p33 .QFLPPPETSGGGLLLKAVYNFATMTTRHHHHHH
```

B.

```
              184
PapMV     ... QFLPPPETS .....  .........  .....  TTRHHHHHH*
PapMV gp100 ... QFLPPPETS [SSAFT IMDQVPFSV SVSQL]  TRHHHHHH*
```

↑ HLA-A*0201 ↑
                  epitopes

Flanking residues from the antigen

FIGURE 18

A.
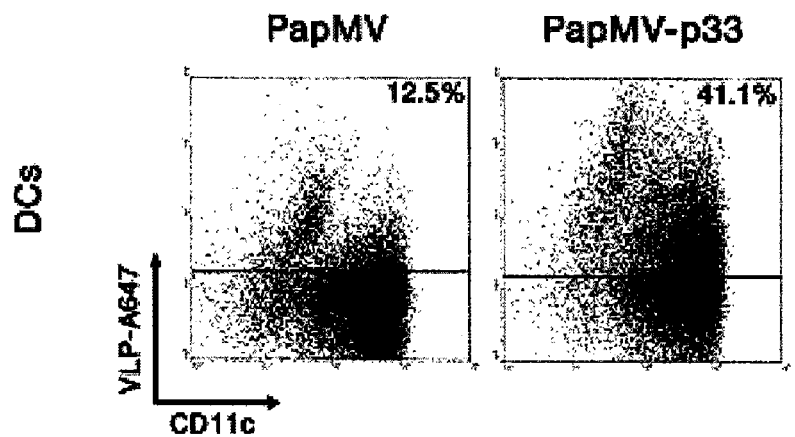
B.
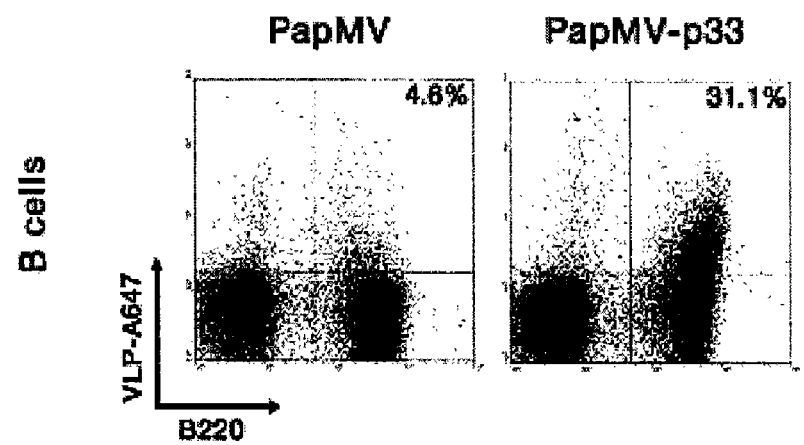
C.
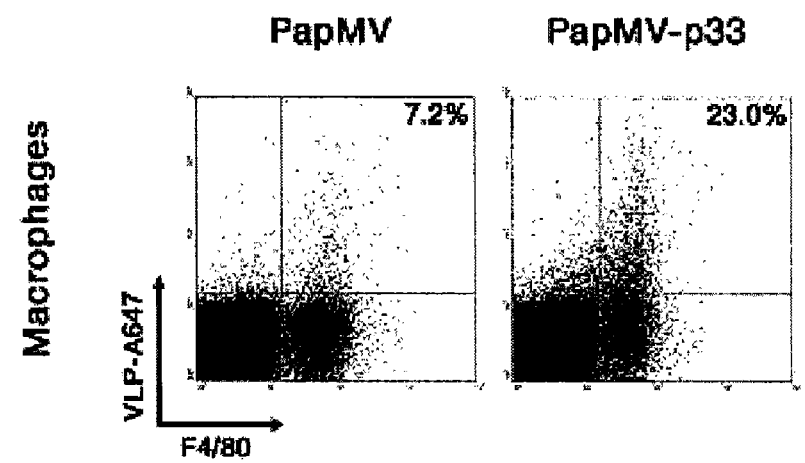
FIGURE 19

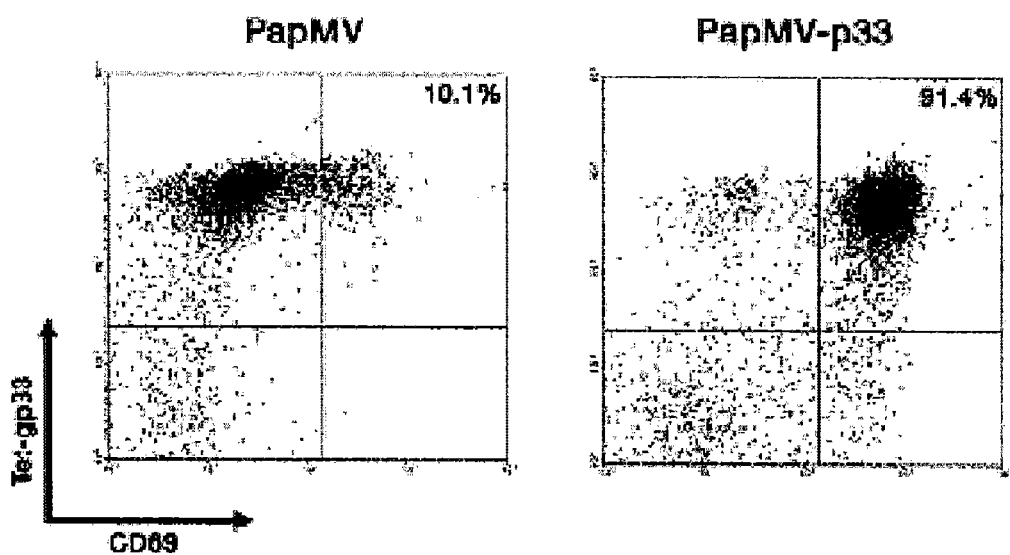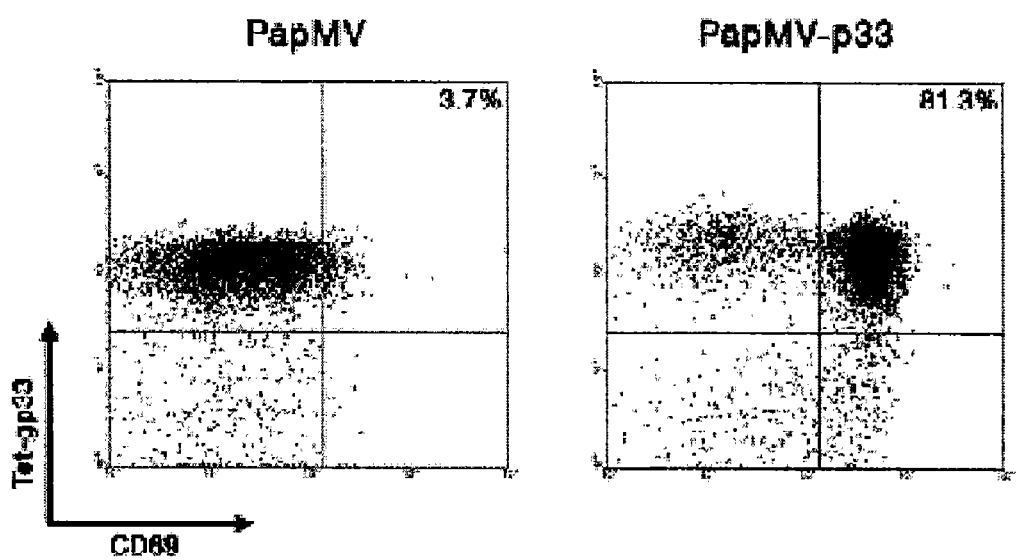
FIGURE 22

VACCINES AND IMMUNOPOTENTIATING COMPOSITIONS AND METHODS FOR MAKING AND USING THEM

CROSS REFERENCE TO RELATED APPLICATIONS

This application is a continuation-in-part of U.S. patent application Ser. No. 10/609,417, filed Jul. 1, 2003 now U.S. Pat. No. 7,641,896, which claims priority from U.S. Provisional Patent Application Ser. No. 60/393,659, filed Jul. 5, 2002. This application also claims priority from U.S. Provisional Patent Application Ser. No. 60/732,659, filed Nov. 3, 2005. The contents of all of the aforementioned applications are hereby specifically incorporated by reference in their entirety.

FIELD OF THE INVENTION

The present invention relates to the field of vaccine formulations and adjuvants and, in particular, to viral particles having an immunopotentiating effect and methods for enhancing an immune response in a human or other animal.

BACKGROUND OF THE INVENTION

Vaccination is one of the most efficient methods to fight against infectious diseases. Over the last past 15 years, genetic engineering has allowed the precise identification of protein fragments that are responsible for the protective immune response and, as a result, new vaccination strategies have emerged. Immunisation of animals with appropriate immunogenic peptides prompts the production of neutralising antibodies that can control diseases. The expression of those immunogenic peptides in heterologous systems has provided the basis of subunit vaccines.

Although it has been demonstrated that chemically synthesised oligopeptides are capable of stimulating the production of antibodies against the protein from which they are derived, the peptides themselves have generally been found to be insufficiently immunogenic to serve as vaccines. Accordingly, there has been considerable interest in developing epitope-presentation systems, in which the peptide sequence is fused to a carrier molecule capable of assembly into a macromolecular structure.

Specific immunity can be enhanced by the use of immunopotentiators, such as adjuvants, when administering an antigen to a host. The immune response is mediated by a variety of cells in the immune system. There are two types of immune response: humoral immunity mediated by antibodies, and cellular immunity mediated primarily by cytotoxic T lymphocytes. Antigen presenting cells ("APC") process and present antigen to both B and T cells. B cells secrete specific antibodies as a result of activation and T cells either become helper cells to the humoral response or cytotoxic cells and directly attack the antigen. Adjuvants have been shown to augment one or both of these immune responses.

Adjuvants are compounds which enhance the immune systems response when administered with antigen producing higher antibody titres and prolonged host response. Commonly used adjuvants include Incomplete Freund's Adjuvant (which consists of a water in oil emulsion), Freund's Complete Adjuvant (which comprises the above with the addition of *Mycobacterium tuberculosis*), and alum. The difficulty, however, in using these materials in humans, for example, is that they are toxic or may cause the host to develop lesions at the site of injection.

Carriers of immunogens of different natures that have been genetically engineered have been described. For example, cowpea mosaic virus (CPMV), tobacco mosaic virus X (TMVX), and alfalfa mosaic virus (AIMV) are known to having been modified for the presentation of epitopes of interest. Another plant viral vector, potato virus X (PVX), a member of the potexvirus group, is known to tolerate carriage of a complete protein overcoat. Also, U.S. Pat. Nos. 6,232,099 and 6,042,832, International Patent applications published under numbers WO 97/39134, WO 02/04007, WO 01/66778, WO 02/00169, and EP application 1167530, all describe different variations of virus-like particles carrying foreign proteins in fusion with endogenous proteins.

MHC class I and MHC class II associated antigen presentation is generally governed by two separate pathways. Endogenous antigens produced intracellularly reach the MHC class I pathway and prime for cytotoxic T cell (CTL) responses if presented by professional antigen presentation cells (APC). Induction of CTL responses is, therefore, usually confined to pathogens that replicate intracellularly. In contrast, T helper cell responses are primed by exogenous protein antigens, which reach the MHC class II pathway in professional APC (Braciale et al., 1987, Immunol. Rev. 98; 95-114; Heemels and Ploegh, 1995, Ann. Rev. Biochem. 64; 463-491; Yewdell et al., 1999, Immunol. Rev. 172; 97-108). These two pathways, however, are not completely separated and it is possible that exogenous antigens are presented in association with MHC class I molecules.

Certain virus-like particles (VLPs) have been reported to induce a CTL response even when they do not carry genetic information (Ruedl et al., 2002, Eur. J. Immunol. 32; 818-825; Storni, et al., 2002, J. Immunol., 168:2880-2886) and can not actively replicate in the cells where they are invaginated. The cross-presentation of a VLP carrying an epitope from lymophocytic choriomeningitis virus by dendritic cells in vivo has been described (Ruedl et al., 2002, ibid). The ability of a VLP carrying an epitope from lymophocytic choriomeningitis virus (LCMV) to prime a CTL response has also been described, however, this VLP was unable to induce the CTL response when administered alone and failed to mediate effective protection from viral challenge. An effective CTL response was induced only when the VLP was used in conjunction with anti-CD40 antibodies or CpG oligonucleotides (Storni, et al., 2002, ibid). An earlier report indicated that porcine parvovirus-like particles (PPMV) carrying a peptide from LCMV were able to protect mice against a lethal LCMV challenge (Sedlik, et al., 2000, J. Virol., 74:5769-5775).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide adjuvant viral particles and uses thereof. In accordance with one aspect of the present invention, there is provided an immunopotentiating composition comprising papaya mosaic virus (PapMV), or a virus-like particle (VLP) derived from PapMV coat protein, wherein said PapMV or said VLP is capable of potentiating an immune response in an animal.

In accordance with another aspect, there is provided a vaccine comprising an immunopotentiating composition of the present invention and one or more immunogens.

In accordance with another aspect, there is provided a method of preparing the immunopotentiating composition of the present invention, said method comprising the steps of: (a) providing a polynucleotide encoding said PapMV coat protein; (b) expressing said polynucleotide in a host cell to provide said PapMV coat protein, and (c) allowing said PapMV coat protein to multimerise and assemble to form said VLP.

In accordance with another aspect of the present invention, there is provided a polynucleotide encoding a PapMV coat protein, said PapMV coat protein being capable of multimerization to form a virus-like particle (VLP).

In accordance with one aspect, there is provided a recombinant PapMV coat protein encoded by the polynucleotide of the present invention.

In accordance with one aspect, there is provided a pharmaceutical kit comprising the immunopotentiating composition of the present invention.

In accordance with one embodiment of the present invention, there is provided an immunogen-carrier complex having an immunopotentiation property, consisting of a viral-like particle (VLP) carrying at least one immunogen in fusion with a protein or fragment thereof of said VLP, that may be used in the preparation of a composition for inducing an immune response against the protein or fragment thereof.

In another embodiment of the present invention there is provided a composition comprising a viral-like particle (VLP) and a protein or an extract derived from a virus, bacteria or parasite, that may be used as a vaccine.

In a further embodiment of the present invention, there is provided a method for immunopotentiating an immune response in a human or an animal which comprises administering to said human or animal an immunogen-carrier consisting of a viral-like particle (VLP) carrying at least one immunogen in fusion with a protein or fragment thereof of said VLP, or administering a VLP or a fragment thereof concomitantly with an antigen not directly linked to said VLP.

In another embodiment of the present invention, there is provided a polynucleotide encoding an immunogen-carrier complex consisting of a viral-like particle (VLP) carrying at least one immunogen in fusion with a protein. In a further embodiment, there is provided a polynucleotide encoding an immunogen-carrier complex consisting of a fragment of a VLP, or a VLP alone, said immunogen-carrier complex having the capacity of being assembled when expressed in a plant cell, an animal cell or a microorganism.

Another embodiment of the present invention also provides for the use of a papaya mosaic virus (PapMV) as an adjuvant.

All publications, patents, patent applications cited herein are hereby expressly incorporated by reference for all purposes.

BRIEF DESCRIPTION OF THE DRAWINGS

These and other features of the invention will become more apparent in the following detailed description in which reference is made to the appended drawings.

FIG. 1 illustrates (A) tricine SDS-PAGE analysis of the PapMV coat protein, and (B) immunogold labelling of a PapMV virus-like particle (VLP) carrying a fused peptide showing that the fused peptide is exposed at the surface of the PapMV VLP.

FIG. 7 illustrates the immune response to (A) PapMV VLPs fused to the E1 or E2 peptide of hepatitis C virus (HCV) when administered subcutaneously (SC) or intraperitoneally (IP) to mice, as compared to (B) the immune response to the E1 and E2 HCV peptides alone.

PapMV, (B) PapMV VLP fused to the gp33 CTL epitope flanked by the 3 adjacent amino acids found in the LCMV glycoprotein sequence (PapMV-gp33-6aa), and (C) PapMV VLP fused to the gp33 CTL epitope (PapMV-gp33).

Figure 11:
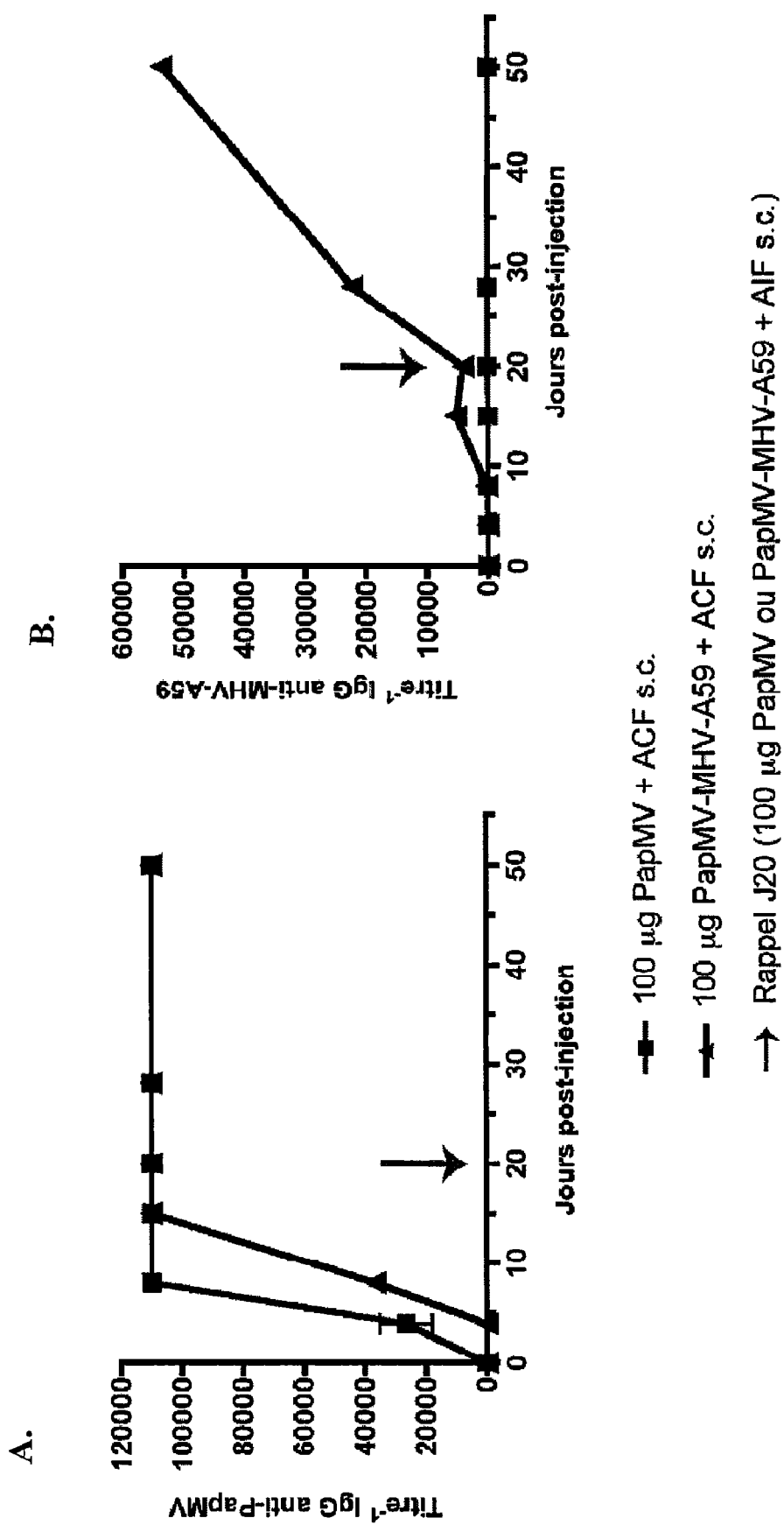

FIG. 11 demonstrates the production of (A) anti-PapMV and (B) anti-MHV-A59 IgGs in mice injected with PapMV or a PapMV VLP expressing an epitope from the S surface glycoprotein of the mouse hepatitis virus, MHV-A59 (PapMV-MHV-A59); the downward arrow indicates administration of a booster at day 20.

Figure 12:
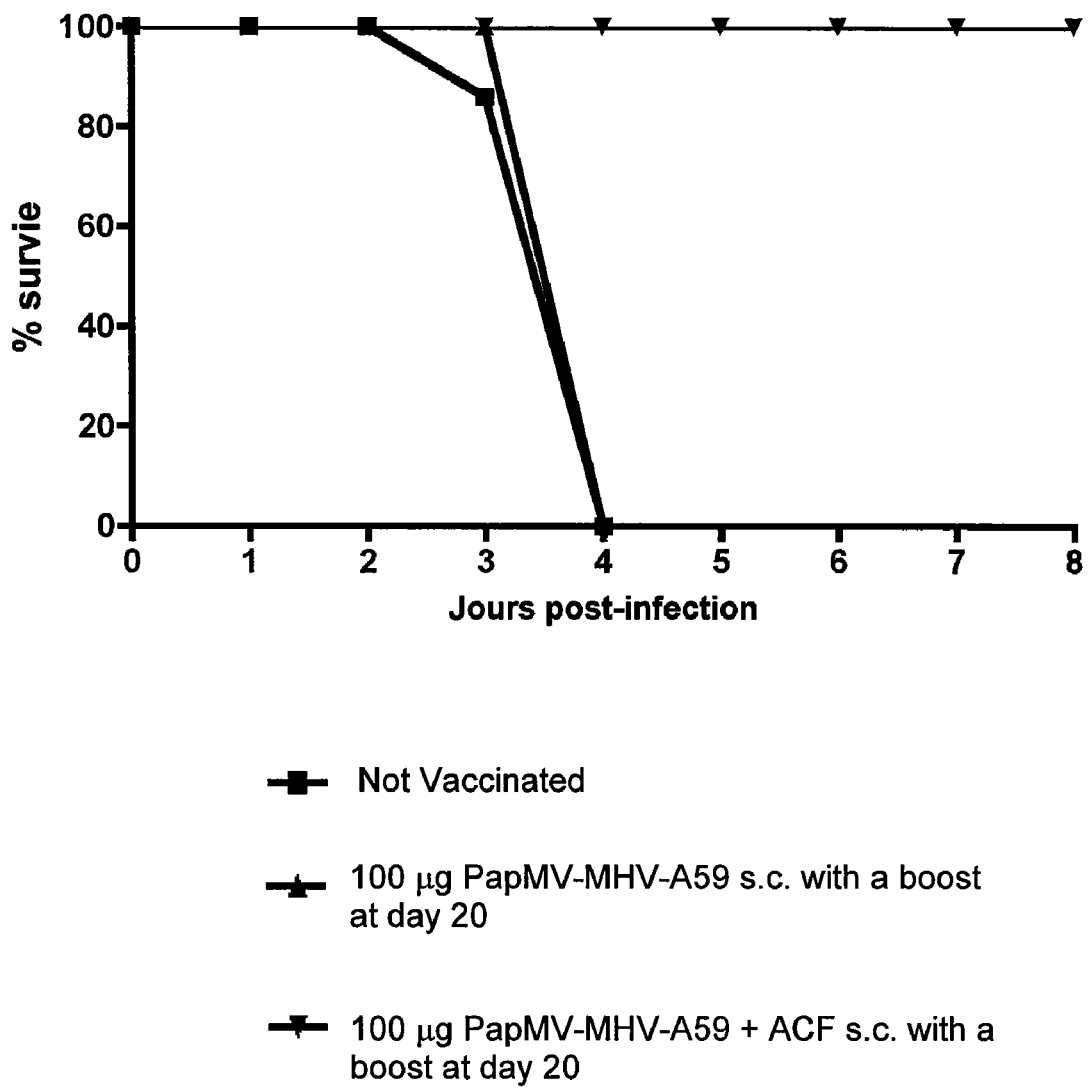

FIG. 12 demonstrates the % survival of mice vaccinated with a PapMV VLP expressing an epitope from the S surface glycoprotein of the mouse hepatitis virus MHV-A59 (PapMV-MHV-A59) and subsequently challenged with a lethal dose of MHV-A59.

Figure 13:
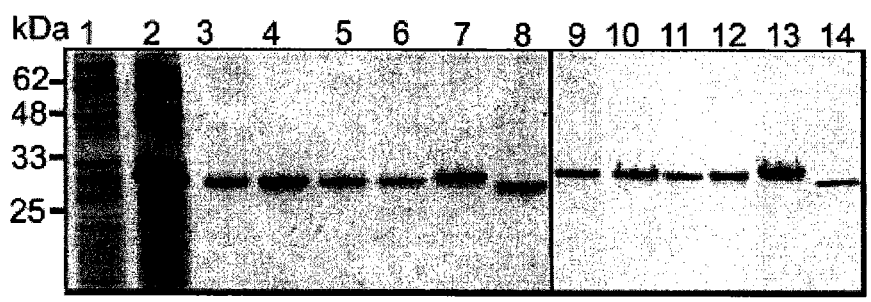

FIG. 13 presents (A) an alignment of a consensus sequence derived from 18 known potexvirus coat protein sequences with the papaya mosaic virus coat protein (PapMV CP) sequence in the conserved region represented by amino acids 90 to 169 of PapMV coat protein; and (B) shows the Coomassie staining profile of recombinant mutant PapMV coat proteins: CPΔN5 (lanes 1, 2 and 3), K97A (lane 4), R104K105R108/A (lane 5), E128A (lane 6) and E148A (lane 7) as compared to PapMV CP from virus purified from plants (lane 8), and the results of Western blotting the purified recombinant proteins: CPΔN5 (lane 9), K97A (lane 10), R104K105R108/A (lane 11), E128A (lane 12), E148A (lane 13) and purified virus from infected plants (lane 14).

Figure 14:
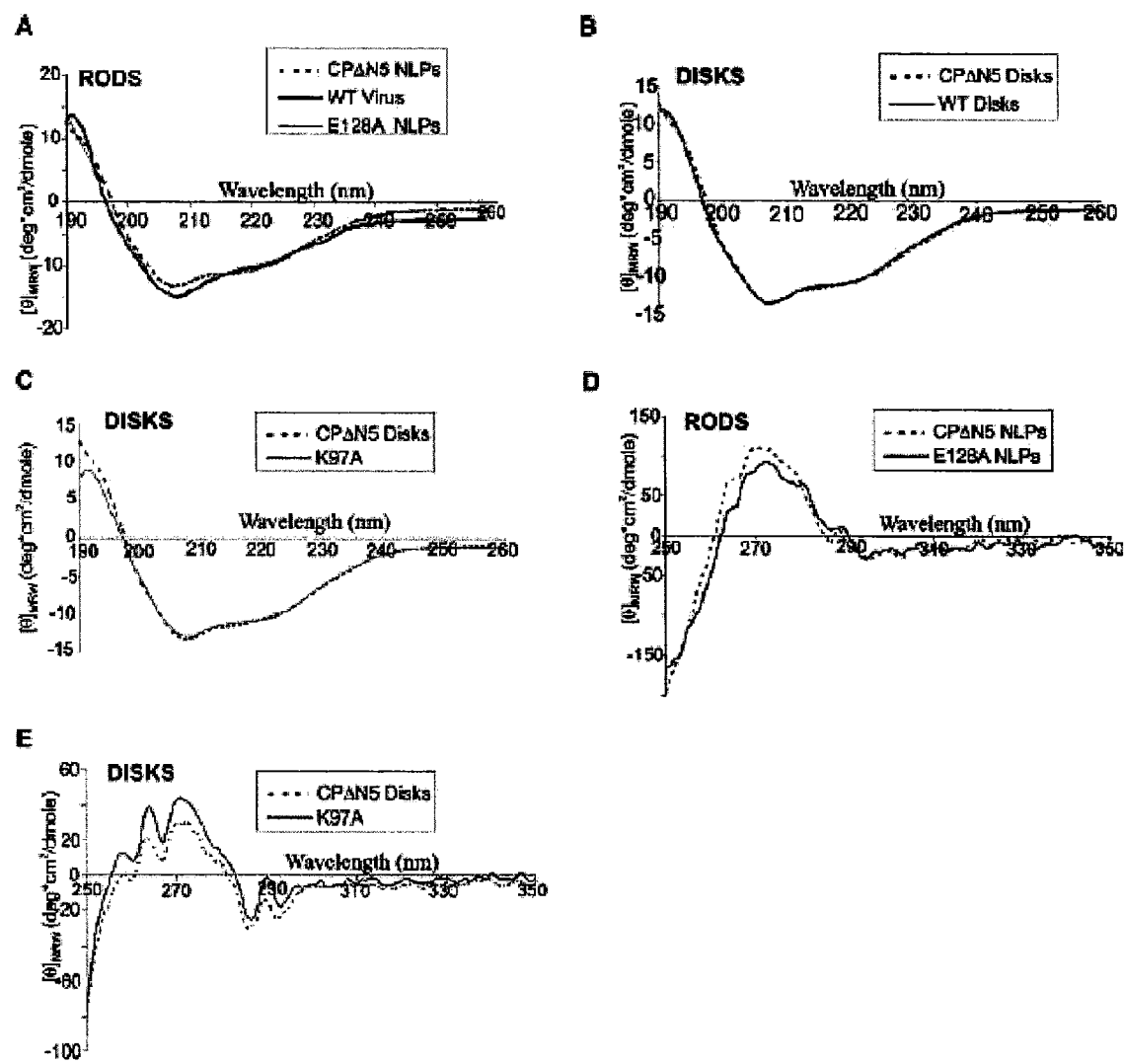

FIG. 14 presents circular dichroism (CD) spectra of wild-type (WT) PapMV and PapMV virus-like particles (VLPs) comprising the recombinant mutant PapMV coat proteins CPΔN5, E128A or K97A; (A) shows far-UV spectra of WT virus (black line), CPΔN5 (dotted line) and E128A VLPs (grey line), (B) shows far-UV spectra of isolated disks from the WT virus by the acetic acid method (black line) and high speed supernatant of the CPΔN5 protein (disks) (dotted line), (C) shows far-UV spectra of the CPΔN5 protein (disks) (dotted line) and the K97A protein (grey line), (D) shows far-UV spectra of the CPΔN5 and E128A VLPs between 250 and 350 nm, and (E) shows far-UV spectra of the CPΔN5 and K97A disks between 250 and 350 nm.

Figure 15:
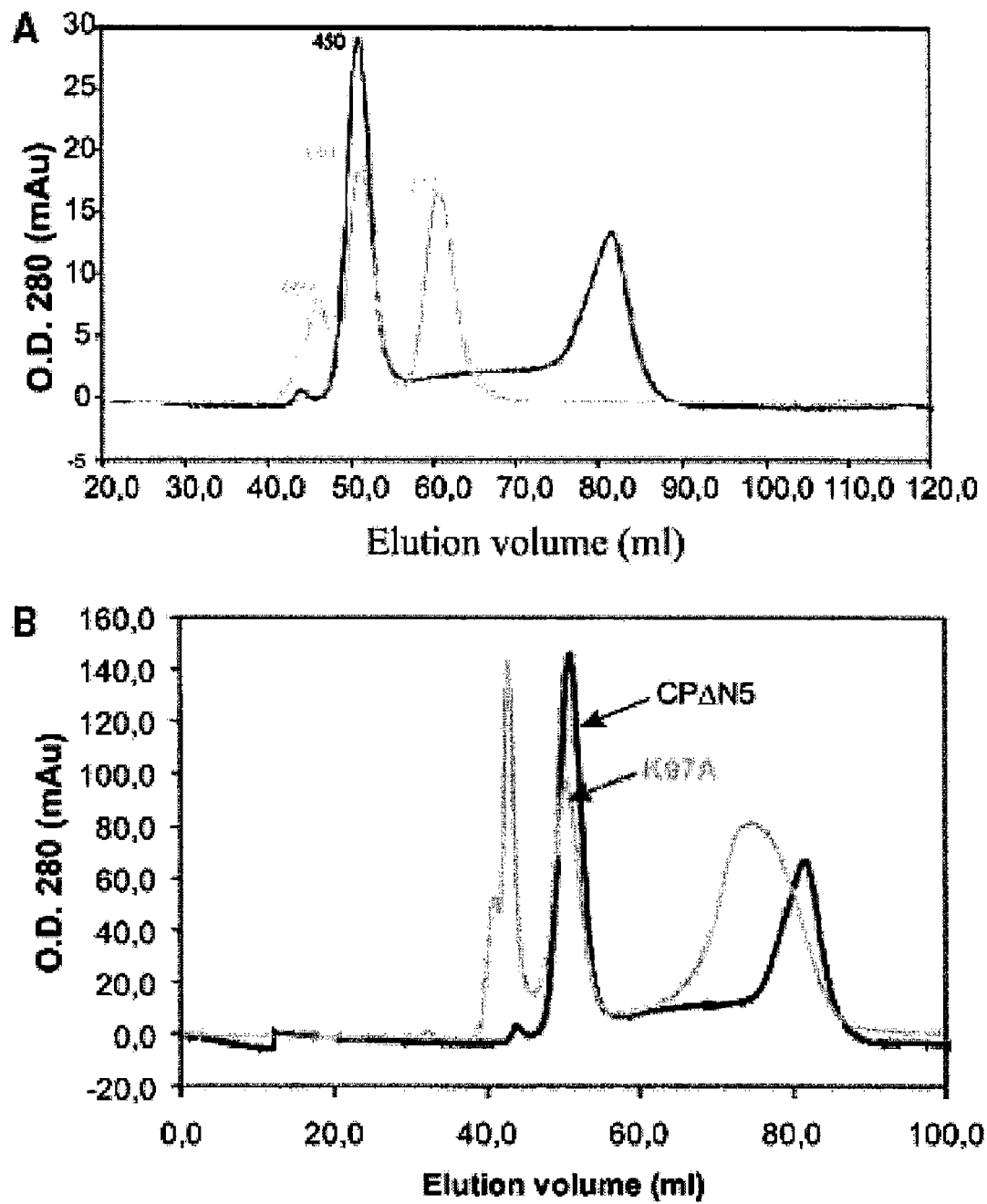

FIG. 15 presents the results of a gel filtration analysis of the recombinant mutant PapMV coat proteins, CPΔN5 and K97A; (A) depicts the protein elution profile for the CPΔN5 purified protein (black line; grey line: molecular weight markers), and (B) depicts the protein elution profile for the CPΔN5 purified protein (black line) and the K97A purified protein (grey line).

Figure 16:
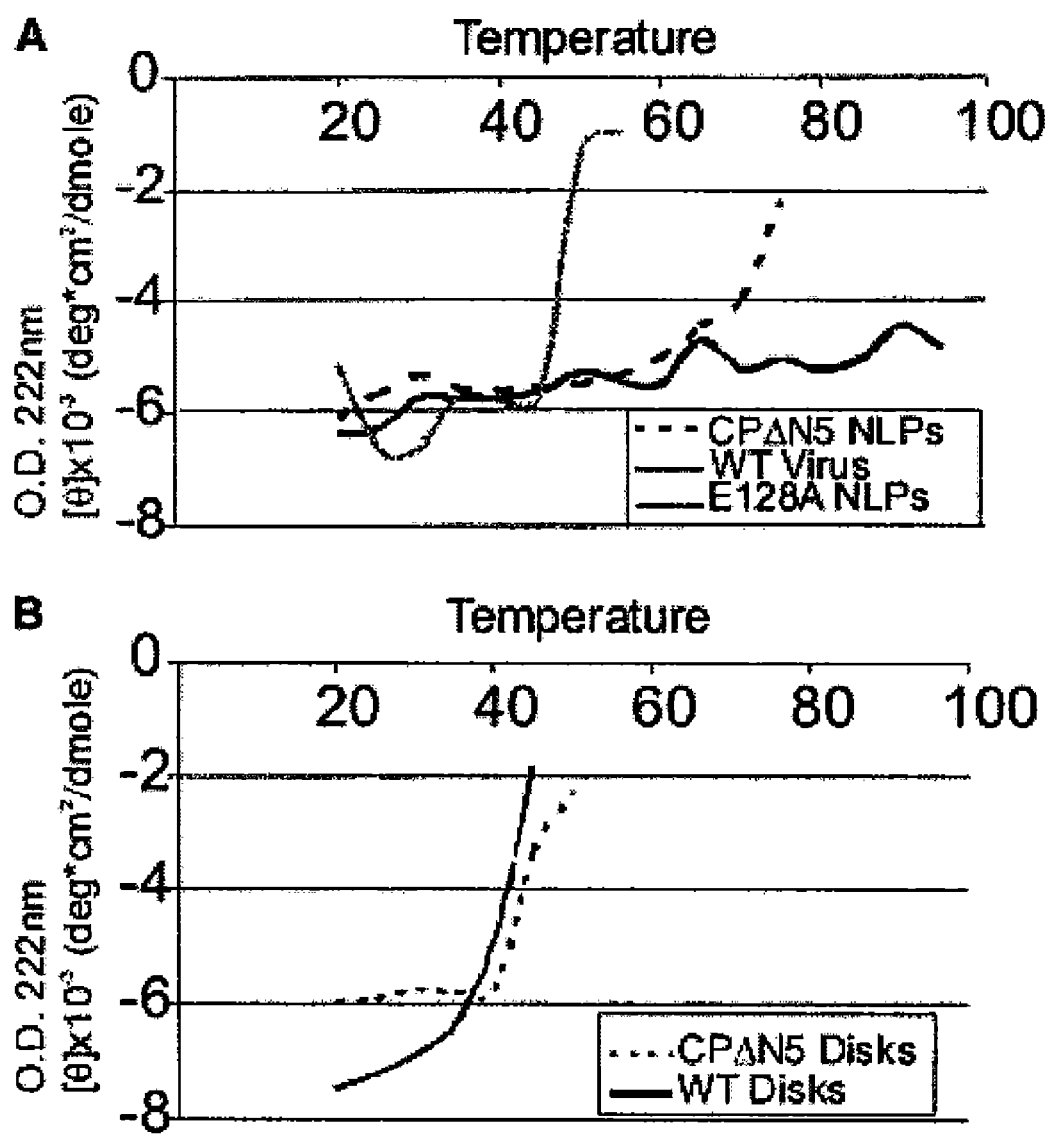

FIG. 16 presents circular dichroism (CD) spectra temperature-induced denaturation curves for the recombinant mutant and wild-type (WT) PapMV coat proteins; (A) shows the profiles for CPΔN5 and E128A mutant VLPs and WT virus, and (B) shows the profiles for CPΔN5 and WT disks. Spectra are presented in units of mean residue ellipticity. Unfolding was monitored by recording [Q] at 222 nm as a function of temperature. All CD spectra shown were generated with proteins at a concentration of 1 mg/ml in 10 mM NaP buffer pH 7.2.

FIG. 17 presents (A) the amino acid sequence for the papaya mosaic virus coat (or capsid) protein (GenBank Accession No. NP_044334.1; SEQ ID NO: 1), and (B) the nucleotide sequence encoding the papaya mosaic coat protein (GenBank Accession No. NC_001748 (nucleotides 5889-6536); SEQ ID NO:2), and (C) the amino acid sequence of the mutant PapMV coat protein CPΔN5 (SEQ ID NO:3).

FIG. 18 presents (A) the C-terminal sequences of PapMV coat protein and a PapMV coat protein-gp33 fusion in which the lymphocytic choriomeningitis virus (LCMV) immunodominant p33 peptide (SEQ ID NO:4; denoted in bold and underlined type) was fused between the C-terminus of the PapMV coat protein and a 6×His tag (6His), and (B) the C-terminal sequence of PapMV coat protein and a PapMV coat protein-gp100 fusion containing the HLA-A*0201 restricted epitope from gp100 (position 209-217 with an M at position 210; SEQ ID NO:5; denoted in bold and underlined type).

FIG. 19 presents the results of flow cytometry analysis of cells isolated from spleens from C57BL/6 mice which had been injected with a PapMV VLP or a PapMV VLP expressing the gp33 CTL epitope found in the LCMV glycoprotein sequence (PapMV-gp33); (A) illustrates the total amount of CD11c$^+$ splenic dendritic cells (DCs); (B) illustrates the amount of B220$^+$ cells in the negative fraction obtained after magnetic purification of CD11c$^+$ cells, and (C) illustrates the amount of F4/80$^+$ cells in the negative fraction. Values shown in each upper right quadrant represent the percentages of a given cell population associated with labeled VLPs within the total population.

Figure 20:
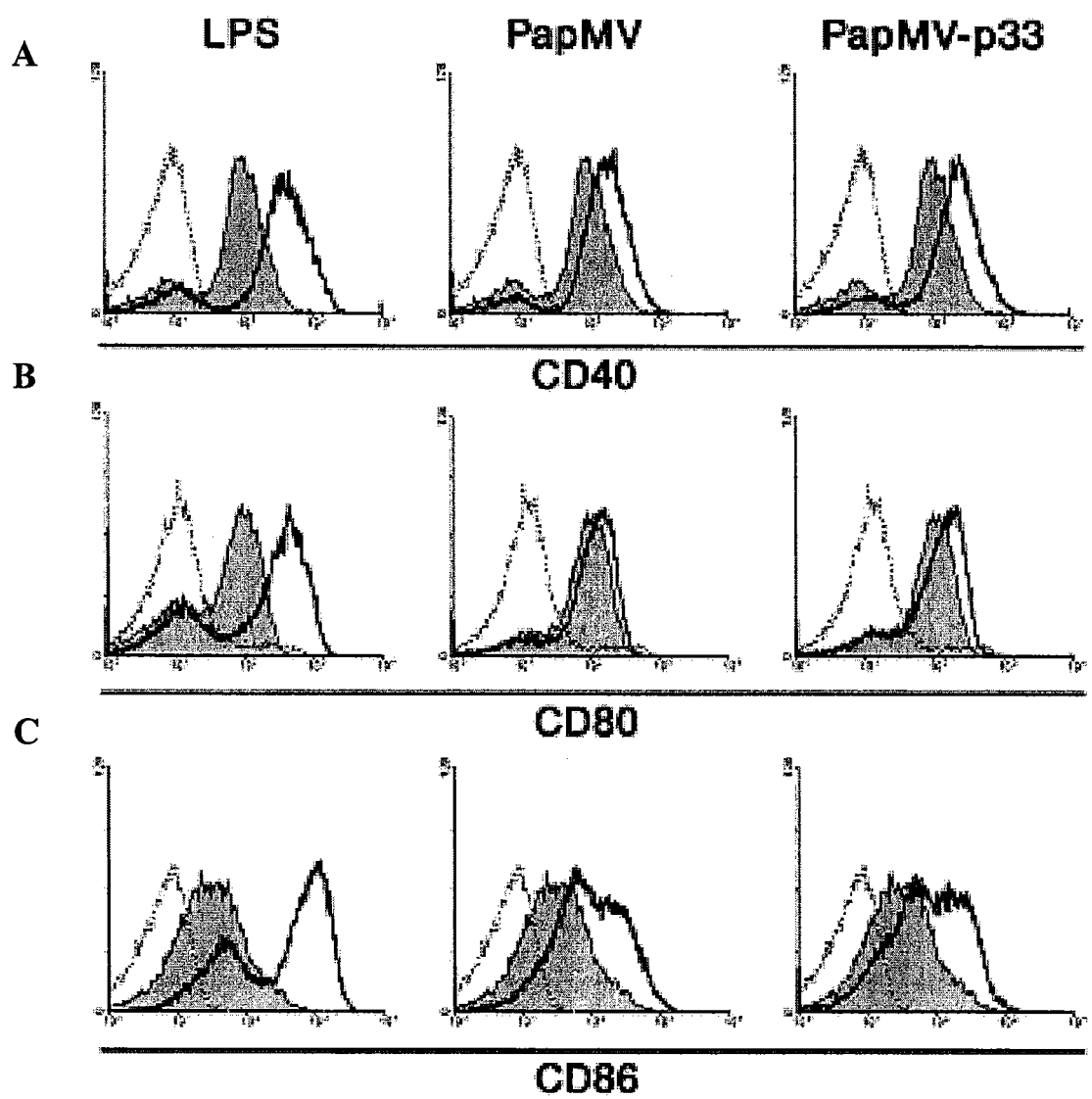

FIG. 20 presents the results of flow cytometry analysis of purified CD11c$^+$ dendritic cells (DCs) isolated from spleens from C57BL/6 mice which had been injected with a PapMV VLP or a PapMV VLP expressing the gp33 CTL epitope found in the LCMV glycoprotein sequence (PapMV-gp33); the purified CD11c$^+$ DCs were stained with labelled CD11c-specific antibodies in combination with (A) labelled anti-CD40, (B) labelled CD80, and labelled CD86. Data are gated on the CD11c$^+$ population. Isotypic controls are shown by dotted lines, PBS injected (control) mice are denoted by the filled histograms and VLP injected mice are denoted by the bold lines.

Figure 21:
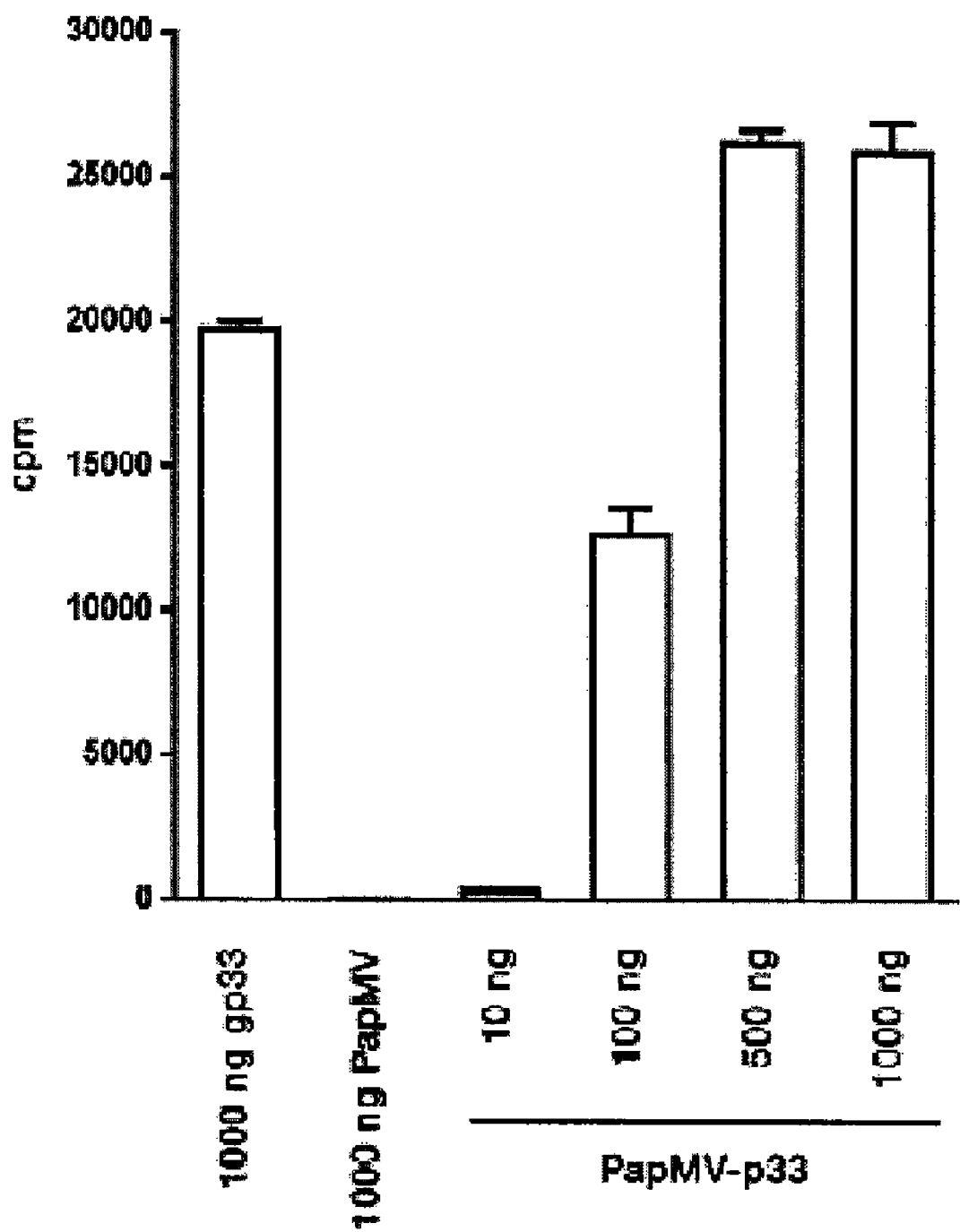

FIG. 21 demonstrates in vitro proliferation of p33-specific CD8$^+$ T lymphocytes after contact with splenic dendritic cells (DCs) treated with a PapMV VLP or a PapMV VLP expressing the gp33 CTL epitope found in the LCMV glycoprotein sequence (PapMV-gp33). Proliferation was assayed by $^3$H-thymidine incorporation to cellular DNA.

FIG. 22 presents the results of flow cytometry analysis of (A) the activation of p33-specific CD8$^+$ T lymphocytes following co-culture between specific T cells and dendritic cells (DCs) treated with a PapMV VLP or a PapMV VLP expressing the gp33 CTL epitope found in the LCMV glycoprotein sequence (PapMV-gp33). Cells were stained with FITC-labelled anti-CD8 antibodies, PerCP-labelled anti-CD69 antibodies and PE-labelled p33-specific tetramers. (C) total spleen cells isolated from P14 mice injected with a PapMV VLP or a PapMV VLP expressing the gp33 CTL epitope found in the LCMV glycoprotein sequence (PapMV-gp33). Cells were stained with FITC-labelled anti-CD8 antibodies, PerCP-labelled anti-CD69 antibodies and PE-labelled p33-specific tetramers. Data are gated on the CD8$^+$ T cell population. Values shown in the upper right quadrants represent the percentages of activated p33-specific CD8$^+$ T lymphocytes within the total spleen p33-specific CD8$^+$ T lymphocytes population.

Figure 23:
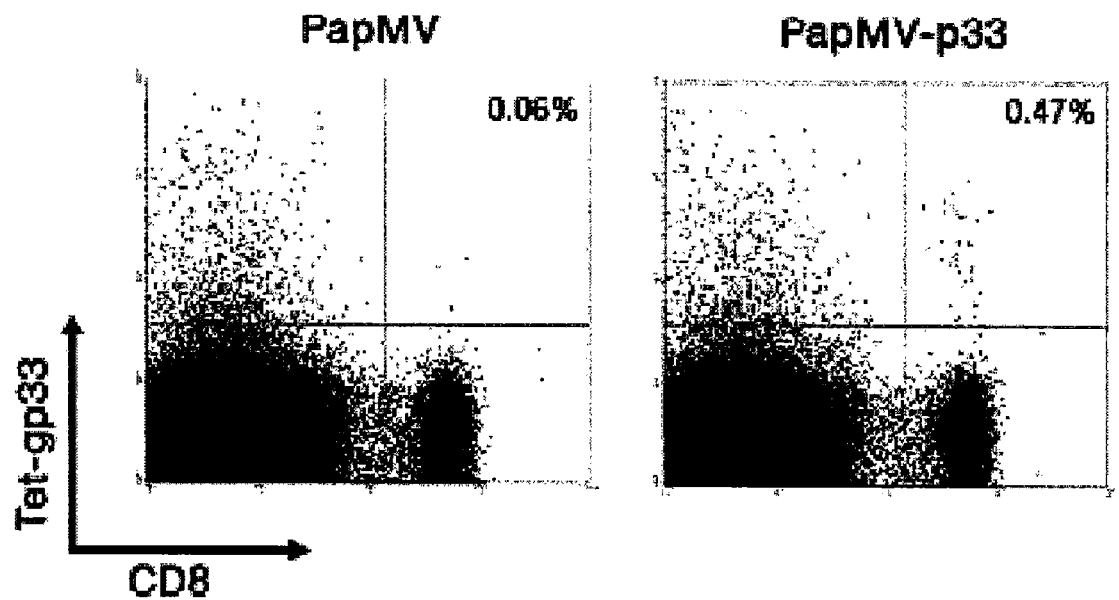

FIG. 23 presents results from the immunization of C57BL/6 mice with a PapMV VLP or a PapMV VLP expressing the gp33 CTL epitope found in the LCMV glycoprotein sequence (PapMV-gp33). Total spleen cells were double-stained with labelled anti-CD8 antibodies and labelled p33-specific tetramers. Data are gated on total lymphocyte populations. Values shown in the upper right quadrants represent the percentage of p33-specific CD8$^+$ T lymphocytes within the total CD8$^+$ T lymphocyte population.

Figure 24:
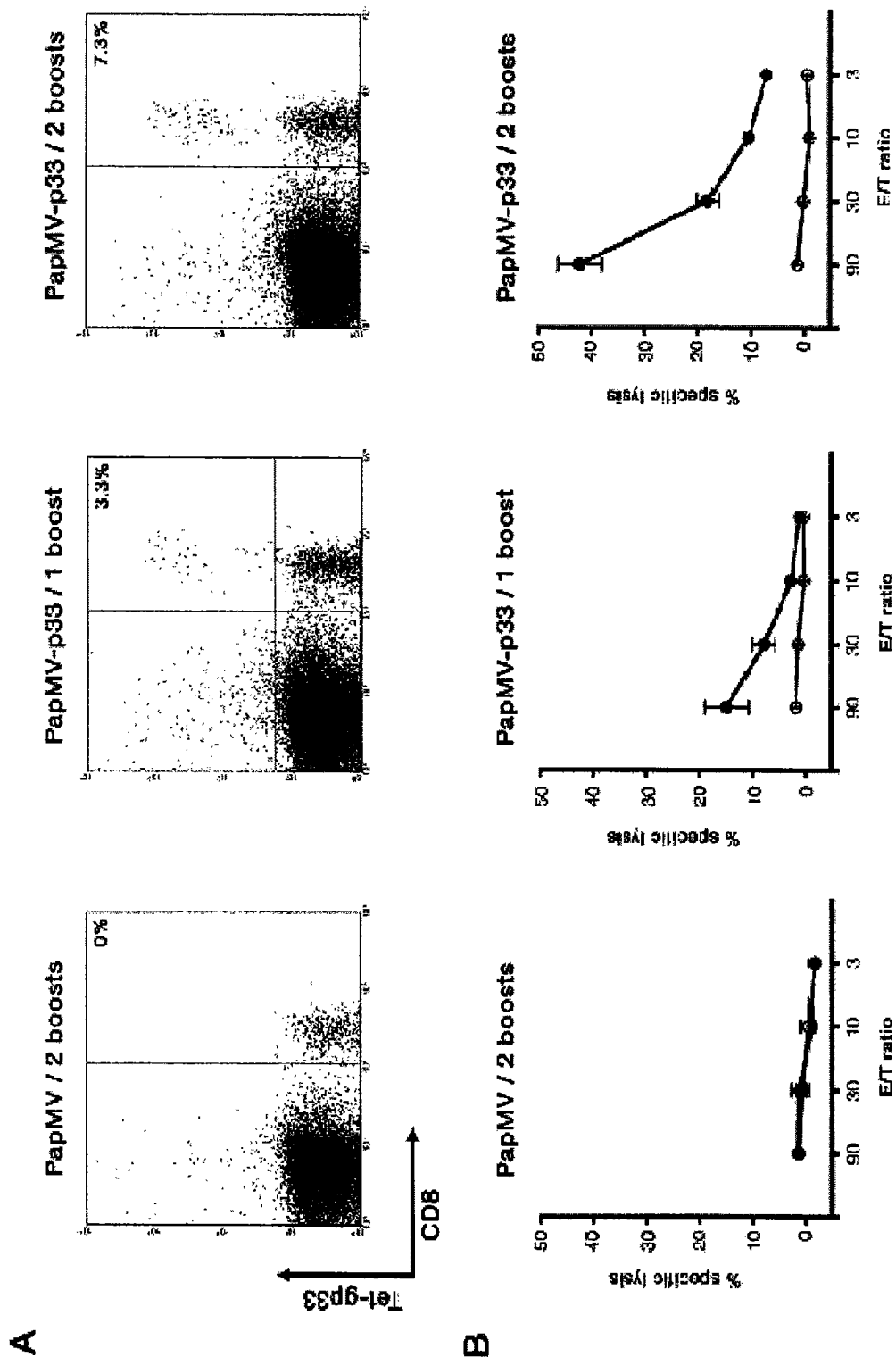

FIG. 24 presents results from LCMV challenge experiments using C57BL/6 mice immunized with either a PapMV VLP or a PapMV VLP expressing the gp33 CTL epitope found in the LCMV glycoprotein sequence (PapMV-gp33). (A) presents flow cytometry results demonstrating expansion of effector p33-specific CD8$^+$ T lymphocytes following LCMV infection of the immunized C57BL/6 mice. Total spleen cells were double-stained with FITC-labelled anti-CD8 antibodies and PE-labelled p33-specific tetramers. Data are gated on total lymphocyte populations. Values shown in the upper right quadrants represent percentages of p33-specific CD8$^+$ T lymphocytes within the total CD8$^+$ T lymphocyte population. (B) demonstrates the cytotoxic activity of spleen cells from the immunized mice as determined by standard $^{51}$Cr release assay on unpulsed (open circle) or p33-pulsed (closed circle) EL-4 target cells.

Figure 25:
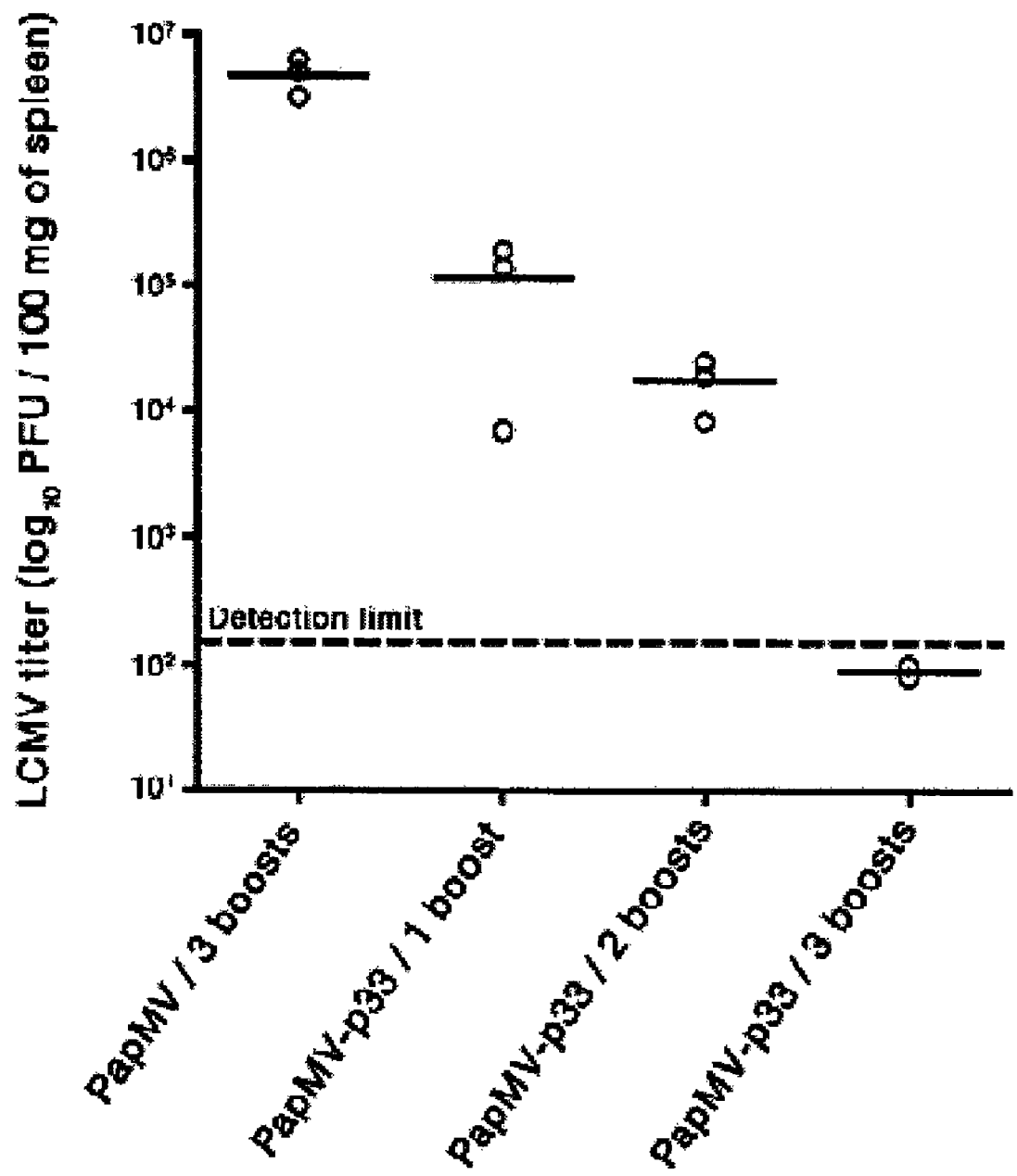

FIG. 25 presents LCMV titers determined by a standard focus forming assay using spleens from C57BL/6 mice immunized with either a PapMV VLP or a PapMV VLP expressing the gp33 CTL epitope found in the LCMV glycoprotein sequence (PapMV-gp33) and subsequently challenged with 200 PFU of LCMV.

Figure 26:
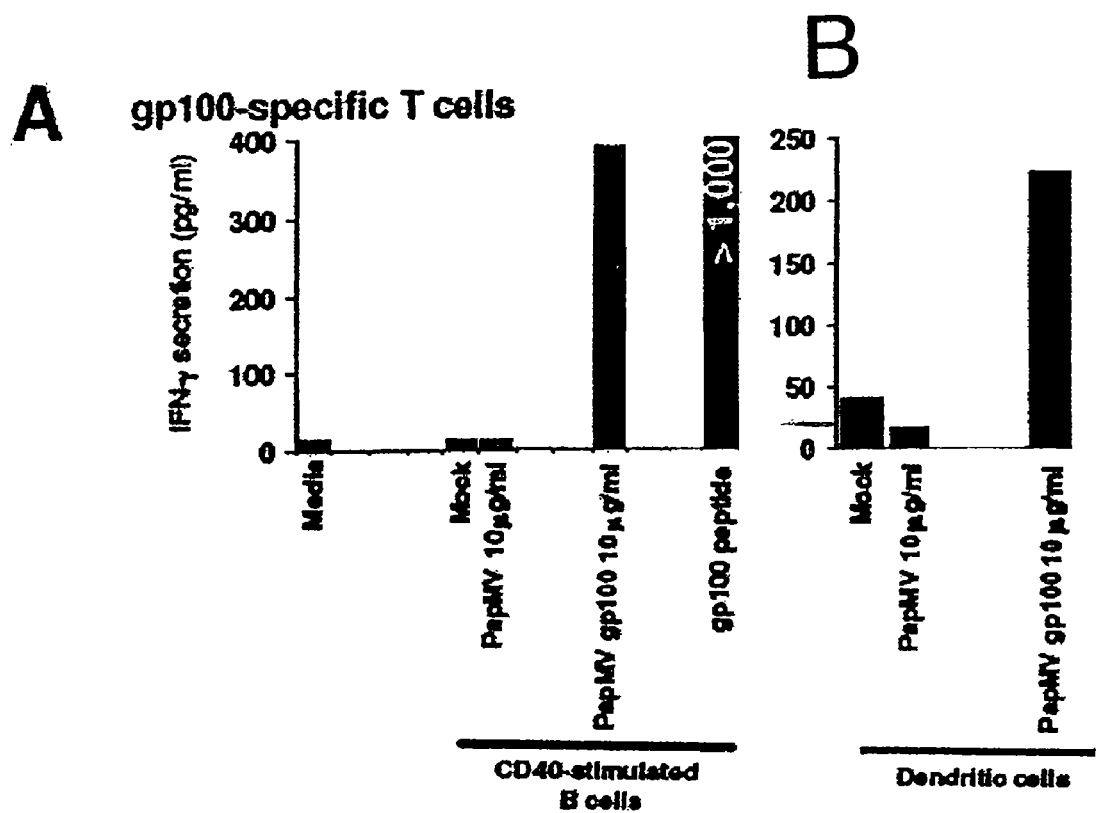

FIG. 26 presents evidence of T cell activation as revealed by IFN-γ secretion from (A) CD40-activated B lymphocytes and (B) dendritic cells (DCs) prepared from an HLA-A*0201 donor and pulsed with a PaPMV-gp100 VLP at various concentrations.

Figure 27:
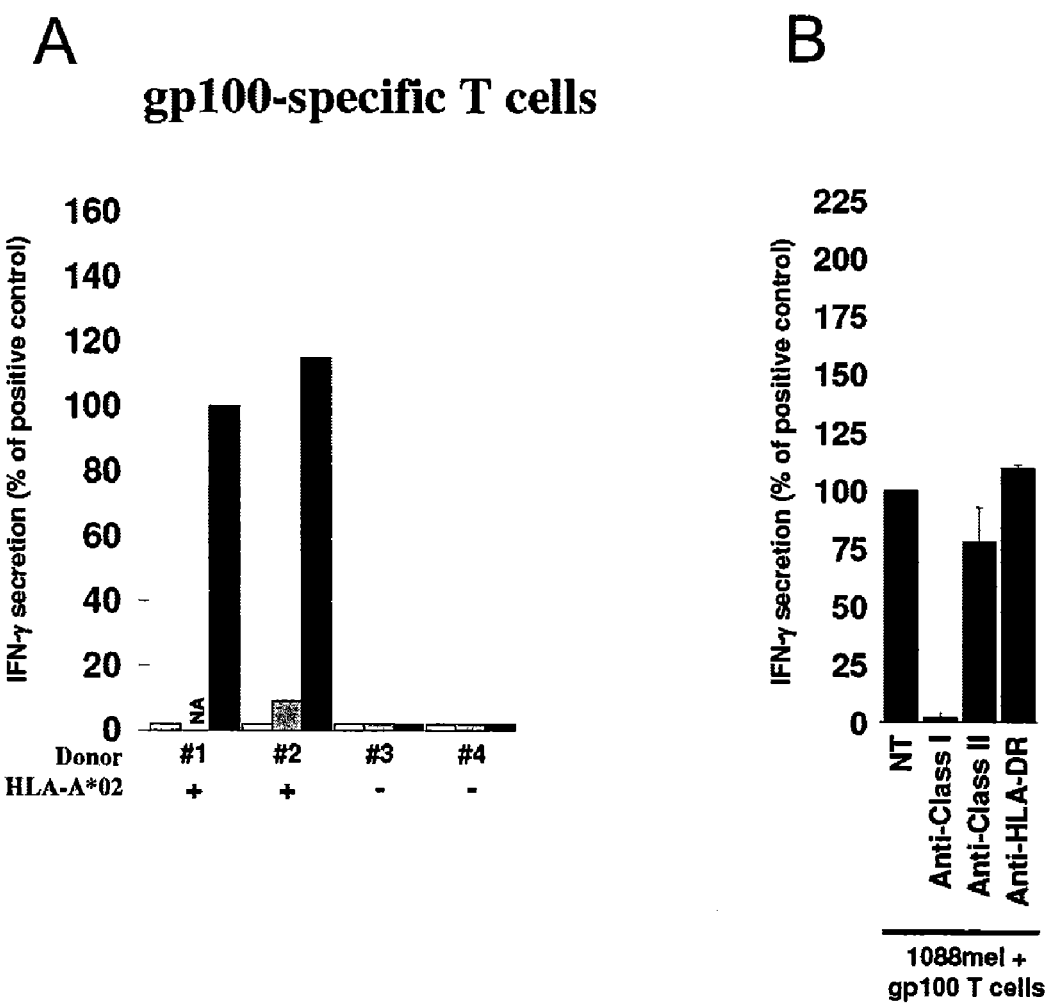

FIG. 27 presents the percentage of recognition based on IFN-γ secretion assay (with 100+ corresponding to the amount secreted by positive controls) for A) PapMV-gp100 pulsed CD40-activated B lymphocytes prepared from HLA-A*02 positive or negative donors that were co-cultured with gp100-specific T cells, and (B) a HLA-A*0201$^+$ and gp100$^+$ melanoma line pulsed HLA-A*02$^+$ CD40-activated B cells that was incubated with antibodies blocking MHC class I, class II or HLA-DR presentation.

Figure 28:
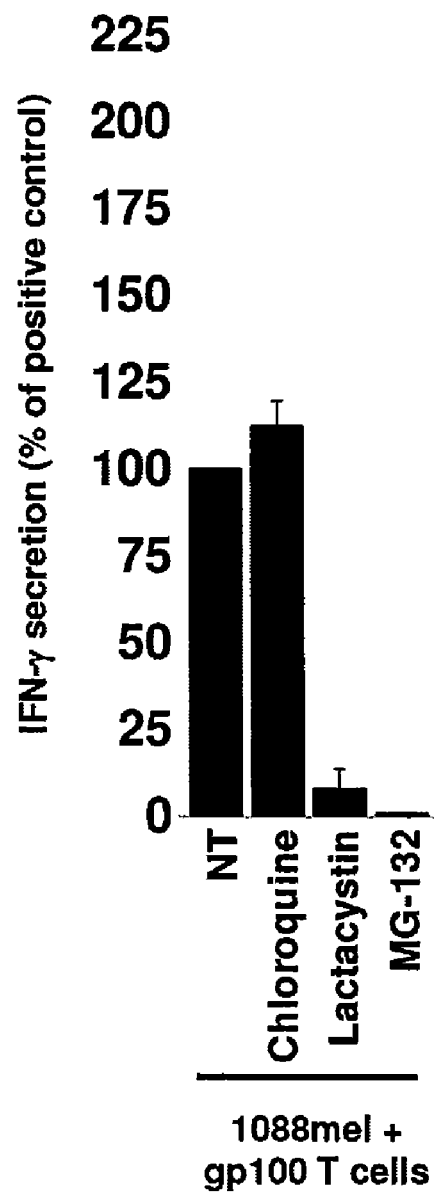

FIG. 28 presents the percentage of recognition based on IFN-γ secretion assay (with 100% corresponding to the amount secreted by positive controls) for a HLA-A*0201+ and gp100+ melanoma line that was incubated with chloroquine, or the proteasome inhibitors lactacystin and MG-132.

Figure 29:
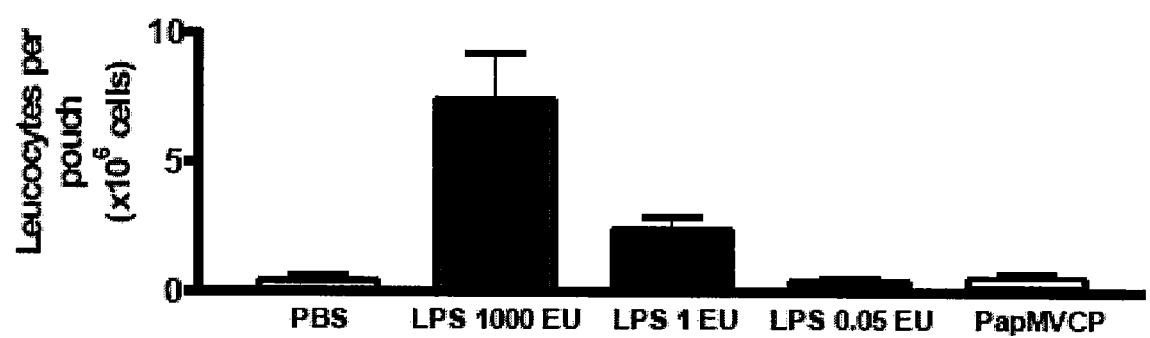

FIG. 29 presents a comparison of the pro-inflammatory response of PapMVCP and LPS in dorsal air pouches raised in CD-1 mice. Data represent the mean±SEM of 5 mice. The results are representative of two identical and independent experiments.

Figure 30:
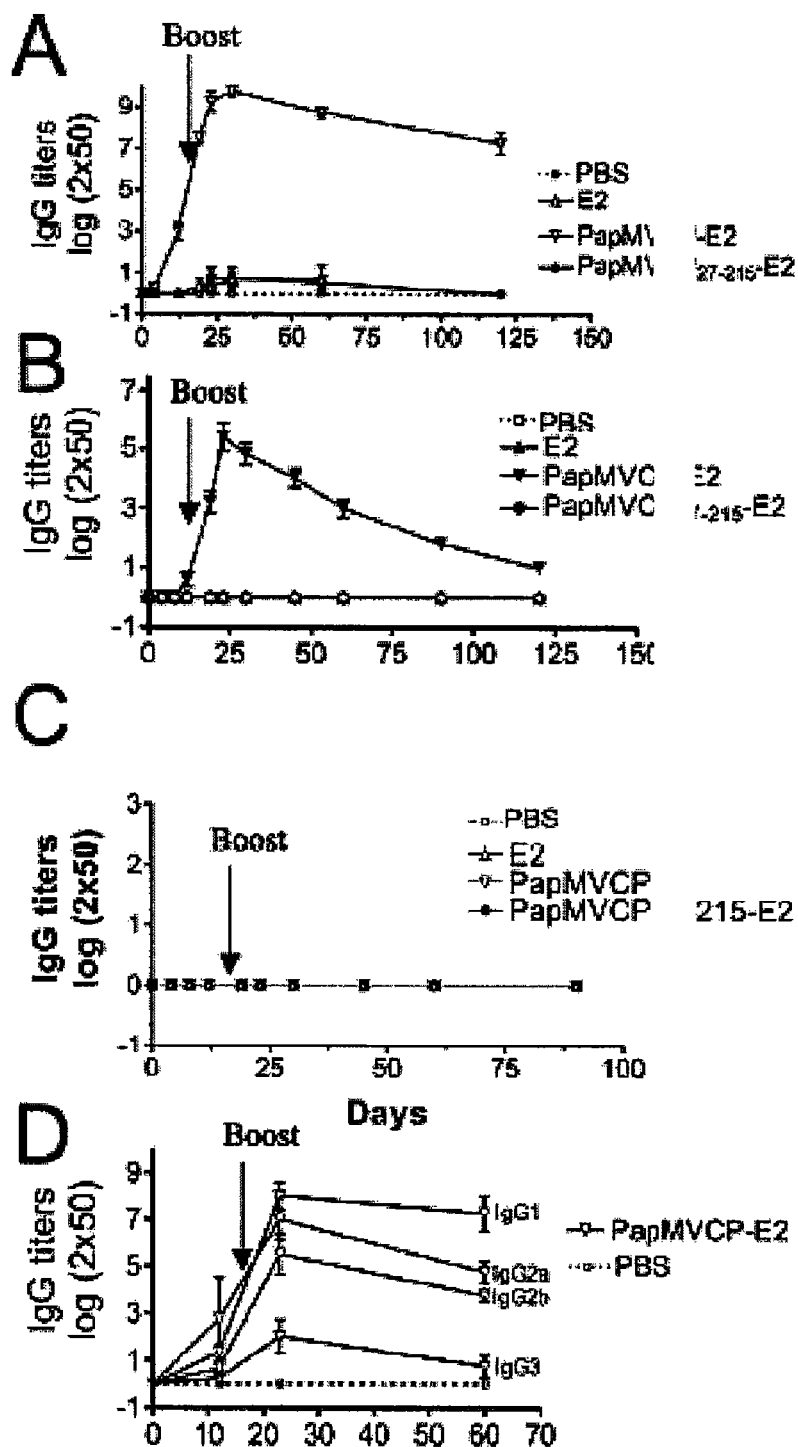

FIG. 30 illustrates the kinetics of the antibody response in C3H/HeJ mice injected subcutaneously with the multimeric PapMVCP-E2, the monomeric counterpart (PapMVCP27-215-E2), HCV E2 peptide alone, or PBS; (A) IgG antibody response specific for the PapMV capsid protein (ELISA plates were coated with PapMV-CP or PapMV$_{27-215}$), (B) IgG antibody response against the HCV E2 epitope (ELISA plates were coated with the HCV E2 peptide fused to the CaMV pIII cargo protein), (C) IgG antibody response to the CaMV pIII cargo protein, (D) IgG isotyping for the HCV E2 epitope antibody response, showing a balanced Th1/TH2 antibody isotyping profile. The results are expressed as antibody endpoint titer, defined as when the D.O value is 3-fold higher than the background value obtained with a 1:50 dilution of serum from PBS-injected mice. Data represent the average of antibody titers from 4 (A) or 5 (B, C, D) mice. These results are representative of two identical and independent experiments. Black arrows on the graphs indicate the booster injections on day 15.

Figure 31:
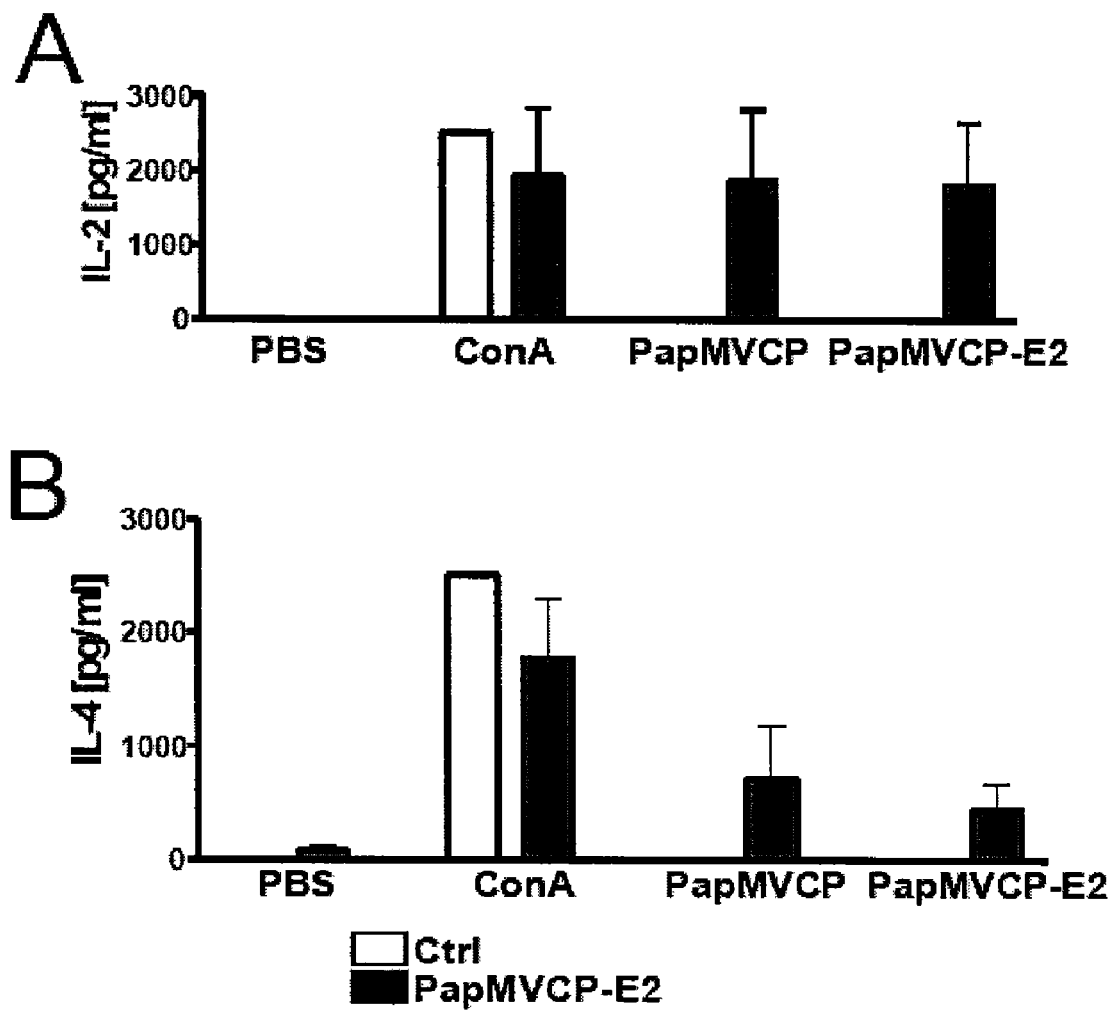

FIG. 31 presents cytokine profiles of reactivated splenocytes with multimeric PapMVCP-E2. Data represent the mean±SEM of 3 mice. White bars: control mice immunised with PBS; black bars: mice immunised with PapMVCP-E2.

DETAILED DESCRIPTION OF THE INVENTION

The present invention provides for an immunopotentiating composition comprising a papaya mosaic virus (PapMV), or a virus-like particle (VLP) derived from PapMV coat protein, which is capable of functioning as an adjuvant and thus potentiating an immune response in an animal. The immunopotentiating composition can further comprise an immunogen, which can be either fused or otherwise linked to the VLP or not linked to the VLP. The immunopotentiating composition is capable of potentiating a humoral and/or a cellular response in the animal.

In one embodiment, therefore, the present invention provides for an immunogen-carrier comprising a virus-like particle (VLP) derived from papaya mosaic virus coat protein. By "derived from" it is meant that the VLP comprises coat proteins that have an amino acid sequence substantially identical to the sequence of the wild-type coat protein and may optionally includes one or more immunogens fused to the coat protein. In accordance with this embodiment, the coat proteins or fusion proteins are capable of multimerisation and assembly into VLPs and each VLP thus comprises a plurality of such proteins. In one embodiment, the VLP comprises a plurality of fusion proteins each of which comprises a first (viral) portion derived from papaya mosaic virus coat protein fused to a second (immunogen) portion that comprises one or more immunogens. In one embodiment of the present invention, the immunogen-carrier is capable of inducing a humoral and/or cellular immune response in an animal. The immunogen-carrier is thus suitable for the development of vaccines against diseases which requires an active participation of one or both of these two branches of the immune system.

The present invention further provides for a recombinant PapMV coat protein that is capable of multimerization and formation of a VLP. The coat protein can be further engineered to include one or more immunogens in fusion with the coat protein such that, upon assembly to form a VLP, the one or more immunogens are exposed on the surface of the VLP. Also provided are polynucleotides encoding recombinant PapMV coat proteins and fusion proteins comprising the PapMV coat protein.

A virus or pseudovirus genetically modified to express the fusion protein forms a further embodiment of the present invention, as does a host cell infected with such a virus or pseudovirus.

The present invention also provides for methods of potentiating an immune response in an animal comprising administering to the animal an immunopotentiating composition comprising an immunogen and a papaya mosaic virus (PapMV), or a virus-like particle (VLP) derived from PapMV coat protein. In one embodiment, the immunopotentiating composition is administered in the form of an immunogen-carrier. The immunopotentiating compositions are suitable for use in man as well as other vertebrate species capable of generating an immune response, and thus have application in both human and veterinary medicine.

DEFINITIONS

Unless defined otherwise, all technical and scientific terms used herein have the same meaning as commonly understood by one of ordinary skill in the art to which this invention belongs.

As used herein, the term "about" refers to approximately a +/−10% variation from a given value. It is to be understood that such a variation is always included in any given value provided herein, whether or not it is specifically referred to.

The term "immunogen" as used herein refers to a molecule, molecules, a portion or portions of a molecule, or a combination of molecules, up to and including whole cells and tissues, which are capable of inducing an immune response in a subject. The immunogen may comprise a single epitope or it may comprise a plurality of epitopes. The term thus encompasses peptides, carbohydrates, proteins, nucleic acids, and various microorganisms, in whole or in part, including viruses, bacteria and parasites. Antigens and haptens are also encompassed by the term "immunogen" as used herein.

As used herein, a "chimeric protein" is a protein that is created when two or more genes that normally code for two separate proteins or protein fragments recombine, either naturally or as the result of human intervention, to provide a polynucleotide encoding a protein (the "chimeric protein") that is a combination of all or part of each of those two proteins. In the context of the present invention, a "fusion protein" is considered to be a "chimeric protein."

The expression "fusion capsid protein" or "fusion coat protein" are used interchangeably herein to refer to a fusion protein in which one of the proteins in the fusion is a plant virus capsid (or coat) protein.

The expression "protective immunity," as used herein, is intended to mean the ability of an animal, such as a mammal, bird, or fish, to resist (delayed onset of symptoms, reduced severity of symptoms or lack of symptoms), as a result of its exposure to an antigen, disease or death that otherwise follows contact with the antigen. Protective immunity is achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Mucosal immunity can be stimulated by an oral vaccine. The primary result of protective immunity is the destruction of the pathogen, or inhibition of its ability to replicate itself, or reduction in the symptoms of a disease.

"Humoral immunity," as used herein, refers to the result of IgG antibodies and IgM antibodies in serum.

"Cellular immunity," as used herein, can be achieved, for example, through cytotoxic T lymphocytes or through delayed-type hypersensitivity that involves macrophages and T lymphocytes, as well as other mechanisms involving T cells without a requirement for antibodies.

A "recombinant virus" is one in which the genetic material of a virus has combined with other genetic material.

The term "polypeptide" or "peptide," as used herein, is intended to mean a molecule in which there is at least four amino acids linked by peptide bonds.

The expression "viral nucleic acid," as used herein, may be the genome (or a majority thereof) of a virus, or a nucleic acid molecule complementary in base sequence to that genome. A DNA molecule that is complementary to viral RNA is also considered viral nucleic acid, as is a RNA molecule that is complementary in base sequence to viral DNA.

The term "virus-like particle" (VLP), as used herein, refers to self-assembling particles which have a similar physical appearance to virus particles and includes pseudoviruses. Virus-like particles may lack or possess dysfunctional copies of certain genes of the wild-type virus, and this may result in the virus-like-particle being incapable of some function which is characteristic of the wild-type virus, such as replication and/or cell-cell movement. VLPs devoid of viral nucleic acids are also contemplated.

The term "vaccine," as used herein, refers to a material capable of producing an immune response and can include a fusion protein, a particle comprising the fusion protein, or a preparation, such as plant material, of which the wild-type protein is a part.

The term "immunopotentiator," as used herein, is intended to mean a substance that, when mixed with an immunogen, elicits a greater immune response than the immunogen alone. For example, an immunopotentiator can enhance immunogenicity and provide a superior immune response. An immunopotentiator can act, for example, by enhancing the expression of co-stimulators on macrophages and other antigen-presenting cells.

The term "immune response," as used herein, refers to an alteration in the reactivity of the immune system of a subject in response to an immunogen and may involve antibody production, induction of cell-mediated immunity, complement activation and/or development of immunological tolerance.

The terms "immunization" and "vaccination" are used interchangeably herein to refer to the administration of a vaccine to a subject for the purposes of raising an immune response and can have a prophylactic effect, a therapeutic effect, or a combination thereof. Immunization can be accomplished using various methods depending on the subject to be treated including, but not limited to, intraperitoneal injection (i.p.), intravenous injection (i.v.), intramuscular injection (i.m.), oral administration, spray administration and immersion.

As used herein, the terms "treat," "treated," or "treating" when used with respect to a disease or pathogen refers to a treatment which increases the resistance of a subject to the disease or to infection with a pathogen (i.e. decreases the likelihood that the subject will contract the disease or become infected with the pathogen) as well as a treatment after the subject has contracted the disease or become infected in order to fight a disease or infection (for example, reduce, eliminate, ameliorate or stabilise a disease or infection).

The term "subject" or "patient" as used herein refers to an animal in need of treatment.

The term "animal," as used herein, refers to both human and non-human animals, including, but not limited to, mammals, birds and fish, and encompasses domestic, farm, zoo and wild animals, such as, for example, cows, pigs, horses, goats, sheep or other hoofed animals, dogs, cats, chickens, ducks, non-human primates, guinea pigs, rabbits, ferrets, rats, hamsters and mice.

"Naturally-occurring," as used herein, as applied to an object, refers to the fact that an object can be found in nature. For example, an organism (including a virus), or a polypeptide or polynucleotide sequence that is present in an organism that can be isolated from a source in nature and which has not been intentionally modified by man in the laboratory is naturally-occurring.

The term "substantially identical," as used herein in relation to a nucleic acid or amino acid sequence indicates that, when optimally aligned, for example using the methods described below, the nucleic acid or amino acid sequence shares at least 70%, at least 75%, at least 80%, at least 85%, at least 90%, at least 95%, at least 96%, at least 97%, at least 98% or at least 99% sequence identity with a defined second nucleic acid or amino acid sequence (or "reference sequence"). "Substantial identity" may be used to refer to various types and lengths of sequence, such as full-length sequence, functional domains, coding and/or regulatory sequences, promoters, and genomic sequences. Percent identity between two amino acid or nucleic acid sequences can be determined in various ways that are within the skill of a worker in the art, for example, using publicly available computer software such as Smith Waterman Alignment (Smith, T. F. and M. S. Waterman (1981) *J Mol Biol* 147:195-7); "Best-Fit" (Smith and Waterman, *Advances in Applied Mathematics*, 482-489 (1981)) as incorporated into GeneMatcher Plus™, Schwarz and Dayhof (1979) *Atlas of Protein Sequence and Structure*, Dayhof, M. O., Ed pp 353-358; BLAST program (Basic Local Alignment Search Tool (Altschul, S. F., W. Gish, et al. (1990) *J Mol Biol* 215: 403-10), and variations thereof including BLAST-2, BLAST-P, BLAST-N, BLAST-X, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. In general, for amino acid sequences, the length of comparison sequences will be at least 10 amino acids. One skilled in the art will understand that the actual length will depend on the overall length of the sequences being compared and may be at least 20, at least 30, at least 40, at least 50, at least 60, at least 70, at least 80, at least 90, at least 100, at least 110, at least 120, at least 130, at least 140, at least or at least 200 amino acids, or it may be the full-length of the amino acid sequence. For nucleic acids, the length of comparison sequences will generally be at least 25 nucleotides, but may be at least 50, at least 100, at least 125, at least 150, at least 200, at least 250, at least 300, at least 350, at least 400, at least 450, at least 500, at least 550, or at least 600 nucleotides, or it may be the full-length of the nucleic acid sequence.

The terms "corresponding to" or "corresponds to" indicate that a nucleic acid sequence is identical to all or a portion of a reference nucleic acid sequence. In contradistinction, the term "complementary to" is used herein to indicate that the nucleic acid sequence is identical to all or a portion of the complementary strand of a reference nucleic acid sequence. For illustration, the nucleic acid sequence "TATAC" corresponds to a reference sequence "TATAC" and is complementary to a reference sequence "GTATA."

Immunopotentiating Compositions

The immunopotentiating compositions of the present invention comprise a PapMV or a virus-like particle (VLP) derived from a PapMV coat protein. The immunopotentiating compositions can further comprise one or more immunogens that can optionally be fused to the coat protein. The immunopotentiating compositions are capable of potentiating a humoral and/or cellular immune response in a mammal.

As is known in the art, one way to obtain a good response of B cells is to present the antigen in an organized manner. Repetitively arranged epitopes have been shown to cross-link to B cell receptor efficiently and induce a prompt T-independent IgM response followed later by an IgG response. Therefore, a good strategy to increase the immunogenicity of the epitopes and the recognition and presentation to the immune system is the expression of the immunodominant epitopes in an organized fashion, for example, on the surface of a plant virus such as PapMV. Particularly, PapMV fulfils several characteristics of a good adjuvant and carrier because it is a phylogenetically distant antigen, it is exogenous to the animal immune system, it is molecularly very complex and it is an organized structure that has a high molecular weight.

In one embodiment of the present invention, therefore, there is provided a method in which the benign high copy number rod-shaped papaya mosaic virus (PapMV) is used to produce an immunogen-carrier complex comprising an immunogen connected to a viral coat protein subunit. When assembled, the virus particles comprise long helical arrays of coat protein subunits (which are typically coat protein-foreign protein fusion molecules) per virion. Generally, the immunogen portion will be displayed on the outer surface of the virus particles.

The coat protein of papaya mosaic virus (PapMV), for example, but without limiting it thereto, is an excellent candidate for the development of such a immunogen-carrier. This virus harbours a crystalline rod shape and is very repetitive (over 1200 copies of the same subunit per virion). As demonstrated herein, it has been surprisingly recognized by the applicant that a crystalline and repetitive structure is not only recognised by the innate immune system, but has in addition an adjuvant effect on the immune system of an immunized host. Immunization experiments with PapMV indicate that this virus induces a very strong immune response in mice and is an excellent vector for the development of a vaccine.

Accessory cells such as macrophages, B lymphocytes, and dendritic cells are essential for the induction of T cell-dependent immune responses. Accessory cells present antigens to MHC-restricted T cells and produce membrane-associated and secreted costimulators that enhance the proliferation and differentiation of T lymphocytes. Therefore, the presence of competent accessory cells stimulates T cell-dependent immune responses, and their absence leads to deficient responses. Resting macrophages and naïve, unstimulated B lymphocytes sented by such antigen-presenting cells (APCs) may fail to stimulate naïve CD4+ T cells, and may even induce T cell tolerance. In contrast, dendritic cells and activated macrophages and B cells do express costimulators, as well as high levels of APCs. In one embodiment of the present invention, a mechanism of action of the immunogen-carrier of the present invention is to enhance the expression of costimulators on macrophages and other APCs. Because of this, the administration of immunogens in the form of an immunogen-carrier of the invention, which acts simultaneously as an adjuvant, can promote cell-mediated immunity and T cell-dependent antibody production.

PapMV Virus-Like Particles

In accordance with the present invention, the PapMV viral-like particles (VLPs) are formed from recombinant PapMV coat proteins that have self-assembled to form a VLP. When assembled, each VLP comprises a long helical array of coat protein subunits. The wild-type virus comprises over 1200 coat protein subunits and is about 500 nm in length. VLPs that are either shorter or longer than the wild-type virus can still, however, be effective. In one embodiment of the present invention, the VLP comprises at least 50 coat protein subunits. In another embodiment, the VLP comprises between about 50 and about 1500 coat protein subunits. In an alternative embodiment, the VLP is at least 40 nm in length. In another embodiment, the VLP is between about 40 nm and about 600 nm in length.

The VLPs of the present invention can be prepared from a plurality of recombinant coat proteins having identical amino acid sequences, such that the final VLP when assembled comprises identical coat protein subunits, or the VLP can be prepared from a plurality of recombinant coat proteins having different amino acid sequences, such that the final VLP when assembled comprises variations in its coat protein subunits.

The coat protein used to form the VLP can be the entire PapMV coat protein, or part thereof, or it can be a genetically modified version of the PapMV coat protein, for example, comprising one or more amino acid deletions, insertions, replacements and the like, provided that the coat protein retains the ability to multimerise and assemble into a VLP. The amino acid sequence of the wild-type PapMV coat (or capsid) protein is known in the art (see, Sit, et al., 1989, *J. Gen. Virol.*, 70:2325-2331, and GenBank Accession No. NP$_{13}$ 044334.1) and is provided herein as SEQ ID NO:1 (see FIG. 17A). The nucleotide sequence of the PapMV coat protein is also known in the art (see, Sit, et al. ibid., and GenBank Accession No. NC_001748 (nucleotides 5889-6536)) and is provided herein as SEQ ID NO:2 (see FIG. 17B).

As noted above, the amino acid sequence of the recombinant PapMV coat protein comprised by the VLP need not correspond precisely to the parental sequence, i.e. it may be a "variant sequence." For example, the recombinant protein may be mutagenized by substitution, insertion or deletion of one or more amino acid residues so that the residue at that site does not correspond to either the parental (reference) sequence. One skilled in the art will appreciate, however, that such mutations will not be extensive and will not dramatically affect the ability of the recombinant coat protein to multimerise and assemble into a VLP. The ability of a variant version of the PapMV coat protein to assemble into multimers and VLPs can be assessed, for example, by electron microscopy following standard techniques, such as the exemplary methods set out in the Examples provided herein.

Recombinant coat proteins that are fragments of the wild-type protein that retain the ability to multimerise and assemble into a VLP (i.e. are "functional" fragments) are, therefore, also contemplated by the present invention. For example, a fragment may comprise a deletion of one or more amino acids from the N-terminus, the C-terminus, or the interior of the protein, or a combination thereof. In general, functional fragments are at least 100 amino acids in length. In one embodiment of the present invention, functional fragments are at least 150 amino acids, at least 160 amino acids, at least 170 amino acids, at least 180 amino acids, and at least 190 amino acids in length. Deletions made at the N-terminus of the protein should generally delete fewer than 25 amino acids in order to retain the ability of the protein to multimerise.

In accordance with the present invention, when a recombinant coat protein comprises a variant sequence, the variant sequence is at least about 70% identical to the reference sequence. In one embodiment, the variant sequence is at least about 75% identical to the reference sequence. In other embodiments, the variant sequence is at least about 80%, at least about 85%, at least about 90%, at least about 95%, and at least about 97% identical to the reference sequence. In a specific embodiment, the reference amino acid sequence is SEQ ID NO:1.

In one embodiment of the present invention, the VLP comprises a genetically modified (i.e. variant) version of the PapMV coat protein. In another embodiment, the PapMV coat protein has been genetically modified to delete amino acids from the N- or C-terminus of the protein and/or to include one or more amino acid substitutions. In a further embodiment, the PapMV coat protein has been genetically modified to delete between about 1 and about 10 amino acids from the N- or C-terminus of the protein.

In a specific embodiment, the PapMV coat protein has been genetically modified to remove one of the two methionine codons that occur proximal to the N-terminus of the protein (i.e. at positions 1 and 6 of SEQ ID NO:1) and can initiate translation. Removal of one of the translation initiation codons allows a homogeneous population of proteins to be produced. The selected methionine codon can be removed, for example, by substituting one or more of the nucleotides that make up the codon such that the codon codes for an amino acid other than methionine, or becomes a nonsense codon. Alternatively all or part of the codon, or the 5' region of the nucleic acid encoding the protein that includes the selected codon, can be deleted. In a specific embodiment of the present invention, the PapMV coat protein has been genetically modified to delete between 1 and 5 amino acids from the N-terminus of the protein. In a further embodiment, the genetically modified PapMV coat protein has an amino acid sequence substantially identical to SEQ ID NO:3, with or without the 6×His tag.

When the recombinant coat protein comprises a variant sequence that contains one or more amino acid substitutions, these can be "conservative" substitutions or "non-conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group. A non-conservative substitution involves the replacement of one amino acid residue by another residue having different side chain properties, for example, replacement of an acidic residue with a neutral or basic residue, replacement of a neutral residue with an acidic or basic residue, replacement of a hydrophobic residue with a hydrophilic residue, and the like.

In one embodiment of the present invention, the variant sequence comprises one or more non-conservative substitutions. Replacement of one amino acid with another having different properties may improve the properties of the coat protein. For example, as described herein, mutation of residue 128 of the coat protein improves assembly of the protein into VLPs. In one embodiment of the present invention, therefore, the coat protein comprises a mutation at residue 128 of the coat protein in which the glutamic residue at this position is substituted with a neutral residue. In a further embodiment, the glutamic residue at position 128 is substituted with an alanine residue.

Likewise, the nucleic acid sequence encoding the recombinant coat protein need not correspond precisely to the parental reference sequence but may vary by virtue of the degeneracy of the genetic code and/or such that it encodes a variant amino acid sequence as described above. In one embodiment of the present invention, therefore, the nucleic acid sequence encoding a the recombinant coat protein is at least about 70% identical to the reference sequence. In another embodiment, the nucleic acid sequence encoding the recombinant coat protein is at least about 75% identical to the reference sequence. In other embodiments, the nucleic acid sequence encoding the recombinant coat protein is at least about 80%, at least about 85% or at least about 90% identical to the reference sequence. In a specific embodiment, the reference nucleic acid sequence is SEQ ID NO:2.

In accordance one embodiment of the present invention, there is provided a VLP carrying one or more immunogens in fusion with an endogenous viral protein to form an "immunogen-carrier" capable of immunopotentiation or exerting an adjuvant effect. In accordance with this embodiment, the VLP comprises fusion coat proteins that include a first (viral) portion that is a recombinant PapMV coat protein fused to a second (immunogen) portion that comprises one or more immunogens. A polynucleotide coding for the immunogen portion can be inserted at or adjacent a terminus of the polynucleotide coding for the viral portion, such that upon translation, the fusion protein has the viral portion at one end and the immunogen portion at the opposite end. It is not necessary for the viral portion to comprise the entire coat protein, but this remains an alternative choice. The fusion coat protein retains the ability to assemble with other fusion coat proteins or with wild-type coat protein to form an immunogen-carrier VLP.

The viral portion of the fusion protein on which the immunogen is attached, is preferably disposed on the outer surface of the VLP in order to enhance immune recognition of the immunogen. Thus the immunogen can be attached at the amino- (N-) or carboxy- (C-) terminus of the coat protein, or it can be inserted in an internal loop of the coat protein which is disposed on the outer surface of the VLP. In one embodiment of the present invention, the immunogen is fused to the C-terminus of the PapMV coat protein.

In a further embodiment of the present invention, the VLPs have a regular multivalent and true helical structure which can be more immunogenic than aggregation of protein or free subunits of proteins, and can be easily assembled from an encoding nucleic acid. Also the greater stability of the particle can provide a long lasting exposure of the immunogen portion to the immune system.

Immunogens

The immunopotentiating compositions of the present invention immunopotentiate, or boost, an immune reaction against a given immunogen. It is known particularly that small molecules often act only poorly as immunogens, for example, in their ability to elicit antibodies in an in vivo system. Attachment of such immunogens to a immunogen-carrier of the present invention, or co-administration of the immunogen with a PapMV VLP, that itself is antigenic, will give rise to improved antibody response and/or other immune response to the smaller molecule.

A variety of immunogens are known in the art and are suitable for use in the immunopotentiating compositions of the present invention. The immunogen can be as small as a hapten, or relatively large, such as a part of a virus or bacteria. The size and type of immunogen selected is not critical to the practice of the present invention. The immunogen may be specific or recognised for surface structures on T cells, B cells, NK cells and macrophages, or Class I or Class II APC associated cell surface structures. In one embodiment, the invention is especially useful for small weakly immunogenic haptens. Examples of immunogens include, but are not limited to, several immunogenic peptides of the HCV surface envelope proteins, *Salmonella typhii* peptides derived from the porin protein, the peptide a9-23 of insulin, and various cancer antigens.

When the immunogen is to be fused to the VLP to form an immunogen-carrier, the immunogen can vary in size from small to quite large. In one example of this combination, of interest to the health care field, a small portion of the Hepatitis B surface antigen, comprising a sequence of determined amino acids, which is not itself antigenic, can be fused to the VLP and the resulting immunogen-carrier used to elicit antibodies in an in vivo system that may cross-react with the native surface antigen of the VLP and also strongly with the whole hepatitis virus. Regardless of the immunogen selected, it must be coupled to the carrier VLP in such a way as not to interfere with the recognition of the immunogen by the host's immune system.

Preparation of the VLPs

The recombinant coat proteins to be used to prepare the VLPs of the present invention can be readily prepared by standard genetic engineering techniques by the skilled worker provided with the sequence of the wild-type protein. Methods of genetically engineering proteins are well known in the art (see, for example, Ausubel et al. (1994 & updates) *Current Protocols in Molecular Biology*, John Wiley & Sons, New York).

Isolation and cloning of the nucleic acid sequence encoding the wild-type protein can be achieved using standard techniques (see, for example, Ausubel et al., ibid.). For example, the nucleic acid sequence can be obtained directly from the PapMV by extracting RNA by standard techniques and then synthesizing cDNA from the RNA template (for example, by RT-PCR). PapMV can be purified from infected papaya leaves that show mosaic symptoms by standard techniques (see, for example Example X provided herein).

The nucleic acid sequence encoding the coat protein is then inserted directly or after one or more subcloning steps into a suitable expression vector. One skilled in the art will appreciate that the precise vector used is not critical to the instant invention. Examples of suitable vectors include, but are not limited to, plasmids, phagemids, cosmids, bacteriophage, baculoviruses, retroviruses or DNA viruses. The coat protein can then be expressed and purified as described in more detail below.

Alternatively, the nucleic acid sequence encoding the coat protein can be further engineered to introduce one or more mutations, such as those described above, by standard in vitro site-directed mutagenesis techniques well-known in the art. Mutations can be introduced by deletion, insertion, substitution, inversion, or a combination thereof, of one or more of the appropriate nucleotides making up the coding sequence. This can be achieved, for example, by PCR based techniques for which primers are designed that incorporate one or more nucleotide mismatches, insertions or deletions. The presence of the mutation can be verified by a number of standard techniques, for example by restriction analysis or by DNA sequencing.

As noted above, the coat proteins can also be engineered to produce fusion proteins comprising one or more immunogens fused to the coat protein. Methods for making fusion proteins are well known to those skilled in the art. DNA sequences encoding a fusion protein can be inserted into a suitable expression vector as noted above.

One of ordinary skill in the art will appreciate that the DNA encoding the coat protein or fusion protein can be altered in various ways without affecting the activity of the encoded protein. For example, variations in DNA sequence may be used to optimize for codon preference in a host cell used to express the protein, or may contain other sequence changes that facilitate expression.

One skilled in the art will understand that the expression vector may further include regulatory elements, such as transcriptional elements, required for efficient transcription of the DNA sequence encoding the coat or fusion protein. Examples of regulatory elements that can be incorporated into the vector include, but are not limited to, promoters, enhancers, terminators, and polyadenylation signals. The present invention, therefore, provides vectors comprising a regulatory element operatively linked to a nucleic acid sequence encoding a genetically engineered coat protein. One skilled in the art will appreciate that selection of suitable regulatory elements is dependent on the host cell chosen for expression of the genetically engineered coat protein and that such regulatory elements may be derived from a variety of sources, including bacterial, fungal, viral, mammalian or insect genes.

In the context of the present invention, the expression vector may additionally contain heterologous nucleic acid sequences that facilitate the purification of the expressed protein. Examples of such heterologous nucleic acid sequences include, but are not limited to, affinity tags such as metal-affinity tags, histidine tags, avidin/streptavidin encoding sequences, glutathione-S-transferase (GST) encoding sequences and biotin encoding sequences. The amino acids corresponding to expression of the nucleic acids can be removed from the expressed coat protein prior to use according to methods known in the art. Alternatively, the amino acids corresponding to expression of heterologous nucleic acid sequences can be retained on the coat protein if they do not interfere with its subsequent assembly into VLPs.

In one embodiment of the present invention, the coat protein is expressed as a histidine tagged protein. The histidine tag can be located at the carboxyl terminus or the amino terminus of the coat protein.

The expression vector can be introduced into a suitable host cell or tissue by one of a variety of methods known in the art. Such methods can be found generally described in Ausubel et al. (ibid.) and include, for example, stable or transient transfection, lipofection, electroporation, and infection with recombinant viral vectors. One skilled in the art will understand that selection of the appropriate host cell for expression of the coat protein will be dependent upon the vector chosen. Examples of host cells include, but are not limited to, bacterial, yeast, insect, plant and mammalian cells. The precise host cell used is not critical to the invention. The coat proteins can be produced in a prokaryotic host (e.g., *E. coli*, *A. salmonicida* or *B. subtilis*) or in a eukaryotic host (e.g., *Saccharomyces* or *Pichia*; mammalian cells, e.g., COS, NIH 3T3, CHO, BHK, 293, or HeLa cells; or insect cells).

If desired, the coat proteins can be purified from the host cells by standard techniques known in the art (see, for example, in *Current Protocols in Protein Science*, ed. Coligan, J. E., et al., Wiley & Sons, New York, N.Y.) and sequenced by standard peptide sequencing techniques using either the intact protein or proteolytic fragments thereof to confirm the identity of the protein.

The recombinant coat proteins of the present invention are capable of multimerisation and assembly into VLPs. In general, assembly takes place in the host cell expressing the coat protein. The VLPs can be isolated from the host cells by standard techniques, such as those described in the Examples section provided herein. The VLPs can be further purified by standard techniques, such as chromatography, to remove contaminating host cell proteins or other compounds, such as LPS. In one embodiment of the present invention, the VLPs are purified to remove LPS.

In one embodiment of the present invention, the coat proteins assemble to provide a virus or pseudovirus in the host cell and can be used to produce infective virus particles which comprise nucleic acid and fusion protein. This can enable the infection of adjacent cells by the infective virus or pseudovirus particle and expression of the fusion protein therein. In this embodiment, the host cell used to replicate the virus or pseudovirus can be a plant cell, insect cell, mammalian cell or bacterial cell that will allow the virus to replicate. In one embodiment of the present invention, the cell is a bacterial cell, such as *E. coli*. The cell may be a natural host cell for the virus from which the virus-like particle is derived, but this is not necessary. The host cell can be infected initially with virus or pseudovirus in particle form (i.e. in assembled rods comprising nucleic acid and a protein) or alternatively in nucleic acid form (i.e. RNA such as viral RNA; cDNA or run-off transcripts prepared from cDNA) provided that the virus nucleic acid used for initial infection can replicate and cause production of whole virus particles having the chimeric protein.

Uses

The immunopotentiating compositions of the present invention are suitable for use as adjuvants to potentiate an immune response in an animal, or as vaccines to induce a protective or therapeutic immune response to an immunogen in an animal. In one embodiment of the present invention, the immunopotentiating compositions induce both a humoral and a cellular immune response.

The immunopotentiating compositions can thus be formulated as pharmaceutical compositions comprising PapMV, or a PapMV VLP and one or more immunogens together with a pharmaceutically acceptable carrier, diluent, and/or excipient. Suitable carriers, diluents, and/or excipients are well known in the art. If desired, an adjuvant or other active ingredient optionally may be included in the compositions. In accordance with one embodiment of the present invention, the immunopotentiating compositions are capable of efficiently potentiating an immune response in the absence of any additional adjuvants.

For administration to an animal, the compositions can be formulated for administration by a variety of routes. For example, the compositions can be formulated for oral, topical, rectal or parenteral administration or for administration by inhalation or spray. The term parenteral as used herein includes subcutaneous injections, intravenous, intramuscular, intrathecal, intrasternal injection or infusion techniques. In one embodiment of the present invention, the compositions are formulated for topical, rectal or parenteral administration or for administration by inhalation or spray. In another embodiment, the compositions are formulated for parenteral administration.

The immunopotentiating compositions preferably comprise an effective amount of the PapMV or PapMV VLP of the invention. The term "effective amount" as used herein refers to an amount of an agent required to exhibit a detectable immunopotentiating effect. The effective amount of PapMV or a PapMV VLP for a given indication can be estimated initially, for example, either in cell culture assays or in animal models, usually in rodents, rabbits, dogs, pigs or primates. The animal model may also be used to determine the appropriate concentration range and route of administration. Such information can then be used to determine useful doses and routes for administration in the animal to be treated, including humans.

Various pharmaceutical compositions suitable for different routes of administration and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

In one embodiment of the present invention, there is provided an immunogen-carrier which comprises a PapMV coat protein linked genetically to an immunogen that is capable of enhancing a subject's immune response to the immunogen. The immunogen-carrier can be administered parenterally, enterally or orally. In another embodiment of the present invention, the invention provides an immunogen-carrier comprising an immunogen coupled to a carrier that is a virus-like particle (VLP) derived from PapMV, which is capable of enhancing the immune response of a subject to the immunogen.

In accordance with a further embodiment of the present invention, the PapMV VLP and immunogen-carrier are capable of inducing a cellular immune response in a subject. In another embodiment, the PapMV VLP and immunogen-carrier is capable of inducing a CTL response in a subject. The ability of the immunogen-carrier of the present invention to induce a CTL response makes the immunogen-carrier particularly useful in the treatment or prevention of cytopathic viral infections, intracellular pathogen infections, and cancer. Thus, in accordance with one embodiment of the present invention, there is provided a vaccine for the treatment or prevention of cancer, a cytopathic viral infection (such as infection by hepatitis B virus (HBV), hepatitis C virus (HCV) or human immunodeficiency virus (HIV)-1), a viral disease or a intracellular pathogen infection in a subject.

In a further embodiment, there are provided immunogen-carriers, which are conveniently produced by recombinant DNA techniques, which are useful in providing univalent as well as multivalent immunogenic vaccines. The immunogen-carrier may be used as a vaccine to raise an immune response in the subject. The immunogen-carrier initially may be given in an appropriate dosage in order to elicit an immune response. This may be followed by boosting with the immunogen-carrier or immunogen alone. A variation of this approach may include the formation of one or more immunogen-carriers wherein one or more forms of an immunogen are coupled to one or more carrier VLPs and a plurality of such immunogen-carriers is administered.

The administration regime need not differ from any other generally accepted vaccination programs. A single administration in an amount sufficient to elicit an effective immune response may be used. Alternatively, as noted above, other regimes of initial administration of the complex followed by boosting with antigen alone or one or more immunogen-carriers may be used. Similarly, boosting with either the immunogen-carrier or immunogen may occur at times that take place well after the initial administration if antibody titres fall below acceptable levels.

Alternatively, the VLP described herein can be used alone as immunopotentiator or adjuvant to enhance an immune response in humans or non-human animals against targeted antigens. It is preferable that the adjuvant or immunopotentiating VLP be administered concomitantly with the antigen against which an immune response must be raised. However, the adjuvant VLP can be administered previously or subsequently to, depending on the needs, the administration of the antigen to humans or animals. According to a particular embodiment of the present invention, the whole virus-like particle is used for stable and long lasting presentation of peptide epitopes for the vaccination of humans and other animals.

According to another embodiment of the present invention, PapMV and PapMV VLPs are stable and can be stored easily at room temperature. Their ability to resist very high temperature and adverse conditions is due to plant viruses having evolved to resist very difficult conditions that found in the environment. This is a very important advantage, for example, when the vaccine must reach people that are living in poor countries, in regions where access is difficult or for the storage of a diagnostic test for a long period.

Kits

The present invention additionally provides for pharmaceutical kits or packs containing an immunopotentiating composition of the invention for use as an adjuvant or vaccine. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other therapeutic agents for use in combination with the immunopotentiating composition of the invention. The kit may optionally contain instructions or directions outlining the method of use or administration regimen for the immunopotentiating composition and/or additional therapeutic agents.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or similar medically approved delivery vehicle.

To gain a better understanding of the invention described herein, the following examples are set forth. It will be understood that these examples are intended to describe illustrative embodiments of the invention and are not intended to limit the scope of the invention in any way.

EXAMPLES

Example I

Preparation of Immunogen-Carrier VLP

PapMV has a rod-like structure that is made by assembly of the coat protein (CP) subunits. One virus particle contains 1200 subunits. A fusion of the selected peptides with the PapMV CP was made such that the peptide was exposed on the surface of the PapMV particles after in vitro assembly from a PapMV CP expressed and purified from an *E. coli* expression system. The assembly of the viral CP then ensured multimerisation of the peptide and has considerably improved avidity.

Figure 2:
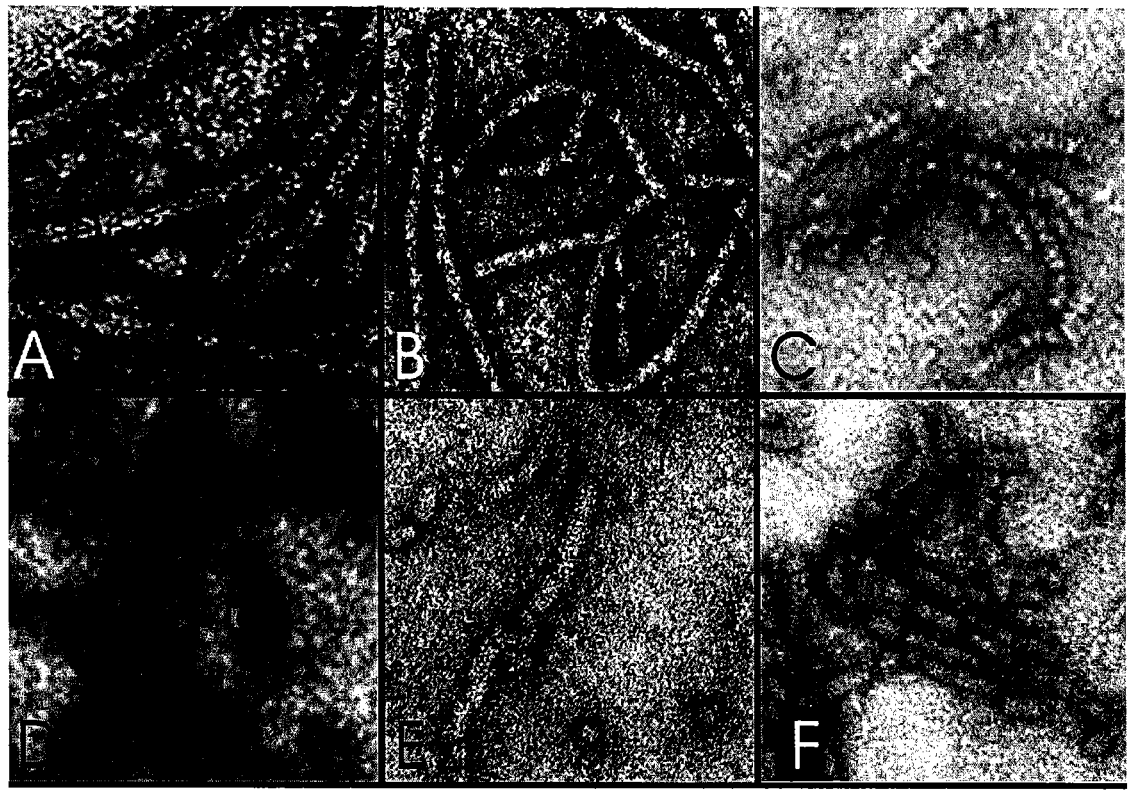
FIG. 2 presents electron micrographs of (A) PapMV purified from infected plants (B) PapMV virus like particles that self-assemble in E. coli upon expression of recombinant coat protein harboring a 6× Histidine tag fusion at the C-terminus, (C) PapMV virus like particles harboring the β9-23 subunit of insulin fused to the C-terminus of the coat protein, (D) PapMV virus like particles harboring the E2 epitope (amino acids 512-536 of the Hepatitis C virus polyprotein) fused to the C-terminus of the coat protein, (E) PapMV virus like particles harboring the E1 epitope (amino acid 285-303 of the Hepatitis C virus polyprotein) fused to the C-terminus of the coat protein, and (F) PapMV virus like particles harboring a peptide (loop 6 peptide) derived from the OmpC protein of *Salmonella enterica typhi* fused to the C-terminus of the coat protein.

Coat protein (CP) gene was cloned and an in vitro assembly system developed using the coat protein (CP) of papaya mosaic virus (PapMV) (FIG. 1). The CP of PapMV was produced in *E. coli* in large amount (FIG. 1A) and produced in vitro PapMV virus-like particles that are very similar to the wt virus (FIG. 2A). It is shown for the first time that a recombinant PapMV CP can assemble in virus-like particles in vitro. Fusion of several peptides to the C-terminus of the CP is allowed by assembly in vitro and gives rise to virus-like particles that are wider than the wt virus because of the fusion (see FIGS. 2B-F: which show CP with a C-terminal (B) 6×Histidine tag, (C) β9-23 subunit of Insulin, (D) E2 epitope (amino acids 512-536 of the Hepatitis C virus polyprotein), (E) E1 epitope (amino acid 285-303 of the Hepatitis C virus polyprotein), and (F) a peptide (loop 6 peptide) derived from the OmpC protein of *Salmonella enterica typhi*). As shown in FIG. 1B the C-terminal peptides are exposed on the surface of the PapMV.

Example II

Immunopotentiation Effect of Immunogen-Carrier VLP

An adjuvant is often used in order to increase the immune response of a candidate vaccine. The enhancement of the inflammatory response favours the migration of more phagocytes to the injection site which, in turn results in an improved antigen presentation by antigen-presenting cells (APC). Alum, emulsions, microparticles and cytokines such as GM-CSF have all been used to increase the immune response of the candidate vaccine. The air pouch model was used to examine whether PapMV induced a proinflammatory event in vivo. In this model, sterile air is injected under the dorsum of mice at days 0 and 3. At day 7, proinflammatory agents can be injected into the air pouch and the inflammatory response measured. This model closely represents subcutaneous injection sites.

In this initial experiment, injection of PapMV into the murine air pouch resulted in the accumulation of approximately $8.5 \times 10^6$ leukocytes, compared to $0.8 \times 10^6$ leukocytes in vehicle-injected mice (PBS). Neutrophils (85%) and monocytes (15%) accumulated in the air pouch 6 hours after injection of PapMV. While quantities as low as 1 μg of PapMV were sufficient to induce the accumulation of leukocytes, maximal accumulation occurred when 100 μg of PapMV was injected. This accumulation was similar to the one induced by injection of 1 μg of LPS, a powerful proinflammatory factor. While these results suggest that PapMV can induce an inflammatory episode, subsequent experiments using PapMV coat protein from which LPS had been expressly removed (less than 0.005 endotoxin units/μg protein; see Example XVII), indicated that these initial results were likely due to the presence of contaminating LPS. Thus, the immunogenic effect of PapMV VLPs as described in detail below and in the following Examples does not depend on LPS-like pro-inflammatory properties.

Figure 3:
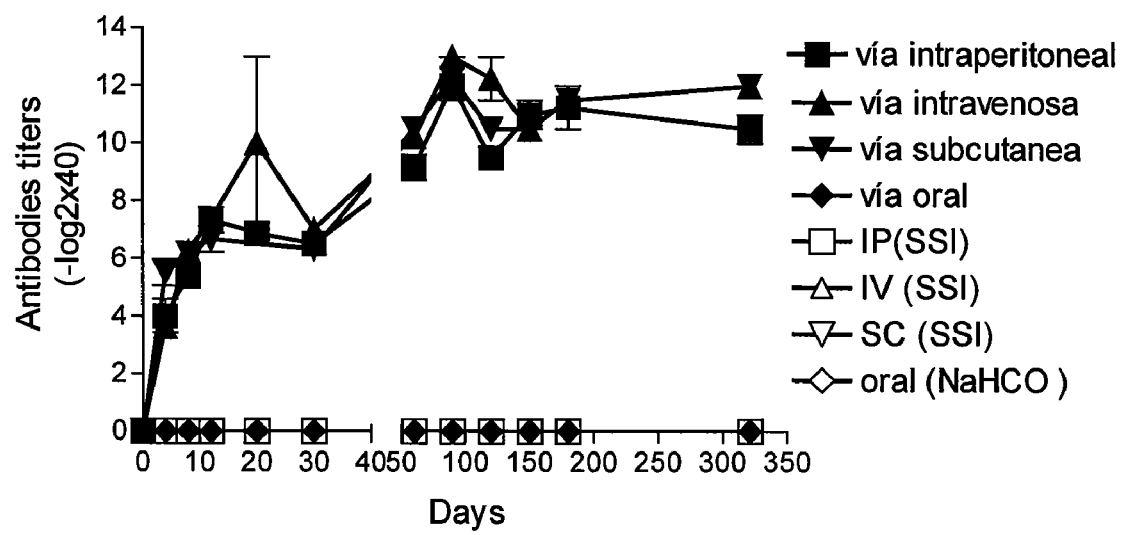
FIG. 3 illustrates the immune response to PapMV in mice (6 for each concentration) that were injected once via intraperitoneal, intravenous or subcutaneous routes with PapMV or received oral administration of PapMV; Isotonic saline solution (ISS) was used as a control.

Furthermore, it was shown in the present experiment that PapMV induces a strong and long lasting humoral response in mice (FIG. 3). 10 mice were injected with three concentrations of PapMV; 1, 10 and 100 μg. Primary antibody response in BALB/c mice immunised with PapMV was efficiently induced independently of the route of immunisation (FIG. 3). High titres were detected at day 5 after immunisation.

A classic curve of a primary IgM response was observed (FIG. 4A). Around day 20, IgM response was absent, even after boosting mice with more viruses. IgG response in immunised mice follows a classic kinetics (FIGS. 4B-E). High titers of anti-PapMV were detected at day 12 after immunisation and proportionally increased after boosting with this virus. Analysis of IgG isotypes showed a preference in the production of IgG2b and IgG1 during the primary and secondary phase of the antibody (Ab) response. IgG3 increased titres during the memory phase of the Ab response (FIGS. 4B-E). These data shows that PapMV is able to induce an efficient Ab response in mice. Primary and secondary responses were efficiently induced as well as a long lasting Ab memory. The preferential production of IgG1 suggests a preferential release of IL-4. IL-4 favours class switching to this kind of IgG. Therefore a balance towards TH2 response could be envisaged in these mice. The lack on IgG2a indicates the absence of IFN-a release, since this cytokine has been involved directly in class switching towards this IgG isotype. Taken together, these data showed the capacity of PapMV to induce an efficient and long lasting antibody response. This result suggests that PapMV particles are excellent vector for the development of a humoral vaccine. The fusion of an immunogen of interest to the VLP will then be recognised as well by the immune system and trigger a strong immune response to the epitope of interest.

Figure 5:
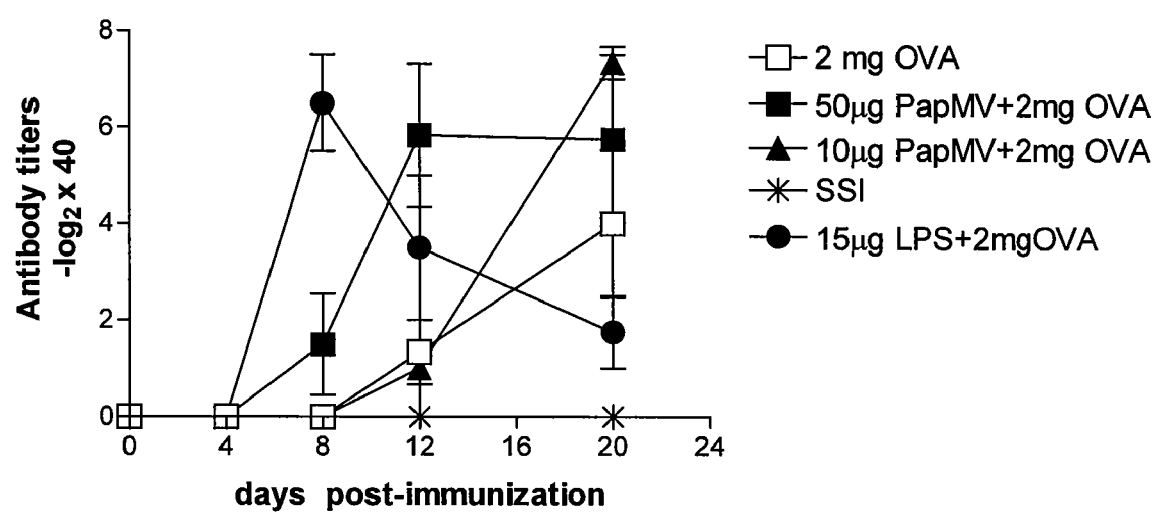
FIG. 5 illustrates the ability of PapMV to act as an adjuvant when administered intraperitoneally to mice in conjunction with the model antigen ovalbumin (OVA).

Also, it was found that PapMV VLPs migrate specifically to the lymph nodes and the spleen after intraperitoneal or subcutaneous injection in Balb/C mice (FIG. 5). This result indicates that PapMV VLPs are excellent carriers because they migrate efficiently to the sites of emergence of the immune response.

Figure 4:
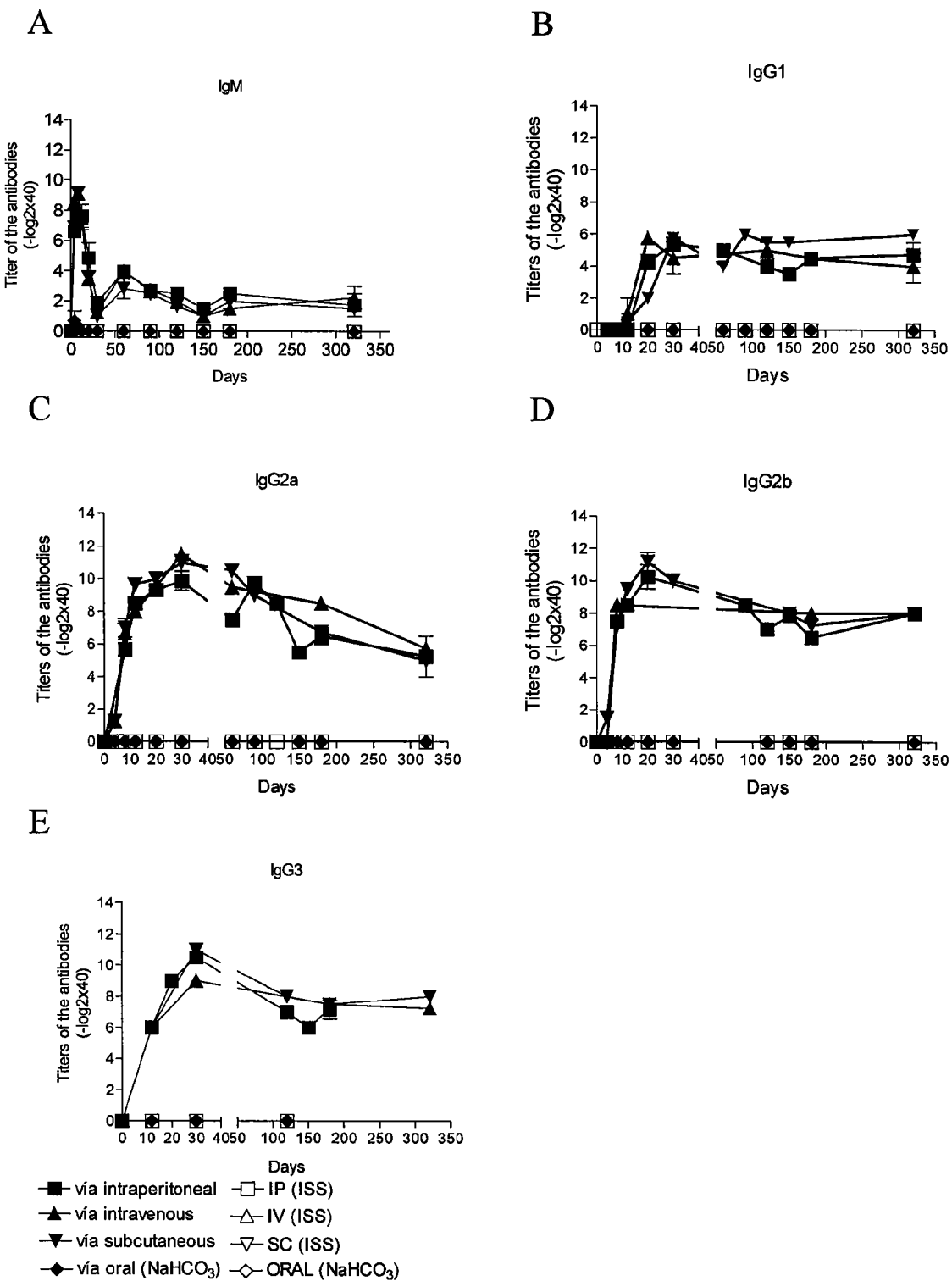
FIG. 4 illustrates an immune response to PapMV in mice (6 for each concentration) that were injected once via intraperitoneal, intravenous or subcutaneous routes with PapMV or received oral administration of PapMV (Isotonic saline solution (ISS) was used as a control); titers of (A) IgM; (B) IgG1; (C) IgG2a; (D) IgG2b, and (E) IgG3, are shown.

Experimental data demonstrate that the PapMV-antigen induces an efficient antibody response in mice (FIG. 3). In fact, primary and secondary responses are efficiently induced as well as a long lasting antibody memory (FIG. 4). Several immunization routes produced efficiently large amounts of antibodies. Only oral immunization did not result in an immune response. It is likely that the $NaHCO_3$ used to neutralize the acid of the stomach damaged the virus particles and affected the immunogenicity of the particles. IgG1, IgG2a, IgG2b and IgG3 were present even 350 days after one injection of 50 μg of PapMV (FIG. 4). Because IgG2a and IgG3 are present and persist, we can deduce that a TH1 response is induced with PapMV. This suggests that PapMV particles are excellent vectors for the development of an immune humoral and cellular response to a foreign antigen. The fusion of an epitope of interest to the PapMV-particle should help to trigger humoral and cellular immune responses against the epitope of interest.

Figure 6:
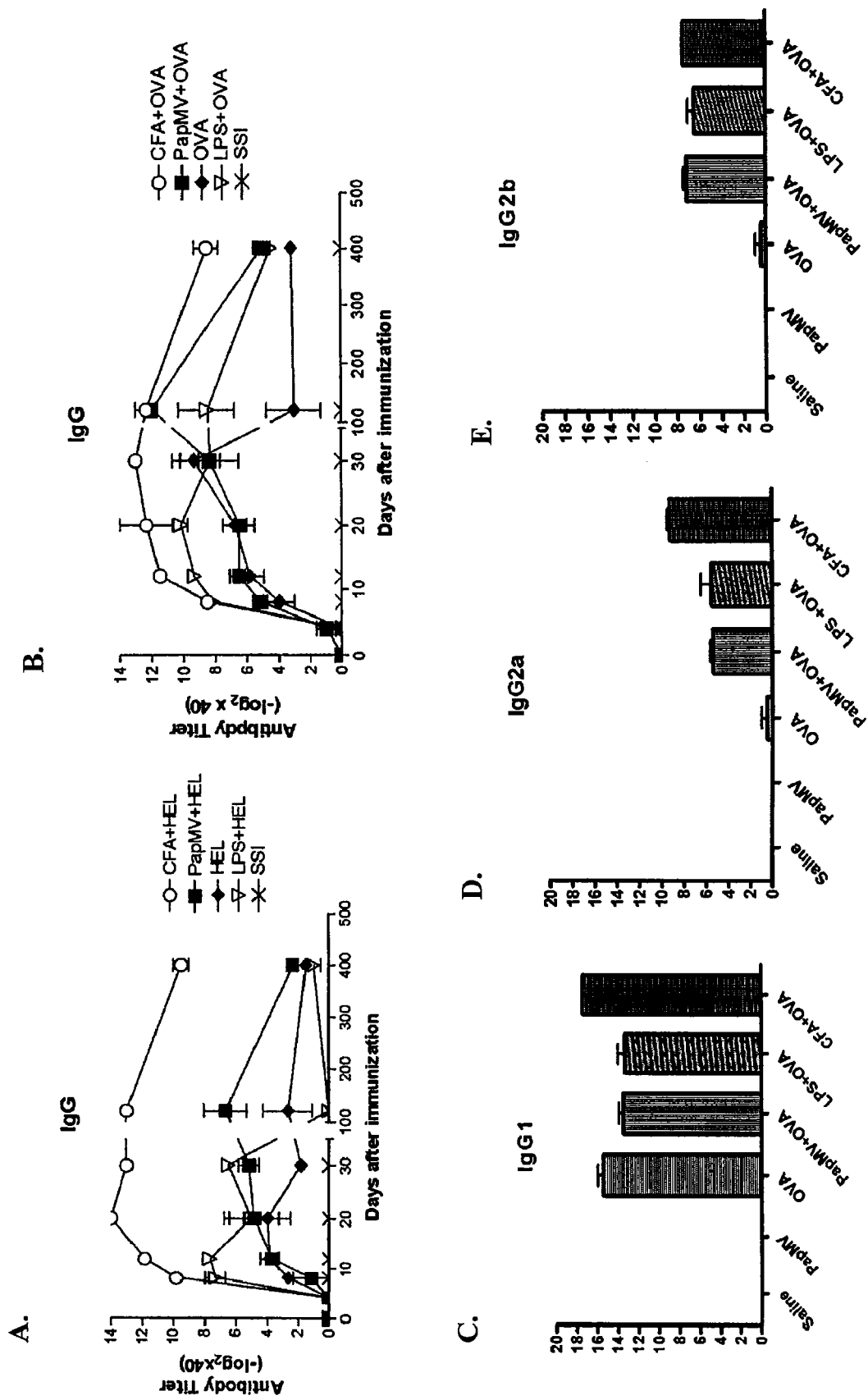
FIG. 6 illustrates the ability of PapMV to strengthen antibody responses to the model antigens (A) hen egg lysozyme (HEL) and (B) ovalbumin (OVA) in BALB/c mice (three per group) immunized on day 0 with antigen alone, antigen plus PapMV, Freund's complete adjuvant (FCA) or LPS from *E. coli* O111:B4. A representative result from 2 experiments is shown. The antibodies of the serum collected from the immunized animals were isotyped by ELISA on the model antigens (HEL or OVA) for (C) IgG1, (D) IgG2a and (E) IgG2b.

Furthermore, PapMV-particles were efficient in inducing an immune response to ovalbumin, a protein known to be a very weak immunogen (FIG. 5). This was established by injecting mice (Balb/C) by intraperitoneal route with 2 mg of ovalbumin alone, or in combination with 50 or 100 μg of PapMV. 6 mice were injected per treatment and samples collected at 0, 4, 8, 12 and 20 days after the injection. Only one injection was made for each treatment. The immune response detected was twice as strong to ovalbumin in presence of PapMV than in its absence, even though ovalbumine is a weak immunogen. This effect is described in more detail in Example XVIII and shown in FIG. 6.

These observations demonstrate that PapMV-particles are rapidly perceived as foreign by the mammalian immune system, which in turn induces signaling and recruitment of cells involved in the defense of the organism.

Example III

Hepatitis C Virus as Vaccination Target

It is known that 20% of infected HCV patients naturally clear the virus. This observation suggests that the immune system can eliminate the viruses if it reacts efficiently. It also suggests that chronically infected patients could be helped by boosting their immune system with a therapeutic vaccine against HCV, which could help to clear the viral infection by raising neutralizing antibodies to the virus.

The 2 epitopes chosen are found at the surface of the HCV virion. The E1 epitope (amino acid 285-303) and E2 epitope (amino acids 512-536), are shown to be strongly immunogenic in patients that have cleared the viral infection (David et al., 2001, J. Virol. 75: 1229-1235). PapMV was engineered to harbour at its C-terminus the fusion of the E1 and E2 peptide of HCV which, can assemble in PapMV virus like particles in vitro (FIGS. 2D and E).

Three epitopes that are found at the surface of the HCV virion of E1 and E2 outside of hypervariable regions 1 (HVR-1) in conserved regions of the viral envelope glycoproteins were chosen. An E1 epitope (amino acid 285-303) and 2 E2 epitopes (amino acids 512-536 and 528-546) were shown to be strongly immunogenic in patients that have cleared the viral infection. Furthermore, one E2 epitope (512-536) was shown to trigger the production of neutralizing antibodies that are found in the sera of patient that cleared the infection. These three regions are good candidates for the development of a HCV vaccine because they are conserved through HCV subtypes and strains and are located outside the hypervariable region of the envelope glycoproteins. The constructs PapMV-E1 and PapMV-E2 were expressed in *E. coli*. The recombinant proteins were purified and assembled in vitro. The assembly of the recombinant coat protein (CP) with the HCV E2 fusions generate rVLPs that are similar to the recombinant wt CP control except that they appear to be slightly larger because of the fusion.

Mice were immunized with the recombinant VLPs that were produced in vitro. LPS was removed using a polymyxin column or by washing with 1% Zwittergent pH 8 on the affinity column and the recombinant VLPs injected into mice intraperitoneally and subcutaneously. 1, 10 and 100 µg of VLPs were used and three mice were injected for each treatment. The immune response to the peptides alone and to the PapMV VLPs was analysed by ELISA (see FIGS. 7A & B). It was observed that IgG were produced to the peptide when presented on the surface of the VLPs (FIG. 7B). This result shows that recombinant PapMV can be used to trigger an excellent immune response at the surface of epitopes and used as vaccine without the help of adjuvant.

Example IV

Immunization Against Typhoid

A membrane protein from *S. typhii* called porin was shown to be a good immunogen because it elicits both antibody and cellular immune response in mice and humans and was able to protect mice against *S. typhi*. Porins are the most abundant protein on the membrane of Gram-negative bacteria and function as passive diffusion channels for low molecular weight molecules. These proteins display a high degree of both structural and functional homology, and are therefore assumed to have a common ancestor. Two small epitopes corresponding to loop 6 and 7 of the *S. typhii* porin that are exposed to the surface of the bacteria were shown to be involved in protective mechanisms elicited by immunization with porins. Those regions are specific for *S. typhii* and are excellent epitope for the development of a recombinant subunit vaccine. Loop 6 of the porin of *S. typhii* was cloned at the C-terminus of the PapMV CP and the recombinant protein was purified and the PapMV virus like particles were produced in vitro with RNA as described above (FIG. 2F).

Example V

Production and Engineering of PapMV VLPs Fused to the gp33 CTL Epitope

In the following Examples (V-VII), PapMV VLPs are shown to efficiently to direct a CTL epitope (LCMV gp33 epitope) to the MHC class I molecule. The gp33 epitope is a peptide derived from the surface glycoprotein of lymphocytic choriomeningitis virus (LCMV) that was shown to be a immunodominant epitope involved in the protection to LCMV infection in mice.

Cloning of the PapMV CP Gene

The PapMV coat protein (CP) gene was amplified by RT-PCR from isolated viral RNA using the following oligonucleotide primers.

Forward CPΔN5 primer:
5'-AGTC<u>CCATGG</u>ATCCAACGTCCAATCTTCTG-3' [SEQ ID NO: 6]

Reverse CPΔN5 primer:
5'-ATGC<u>GGATCC</u>TTACTAATGGTGATGGTGATGGTG [SEQ ID NO: 7]
TTCGGGGGGTGGAAG-3'

The PCR product was digested with NcoI and BamHI and inserted into the vector pET-3d to generate the CPΔN5 PapMV VLP clone, in which 5 amino acids at the N-terminus were deleted from the WT sequence. PapMV VLP also harbors the insertion of an alanine at position 2 of the recombinant protein. The amino acid sequence of the CPΔN5 PapMV VLP clone is shown in FIG. 17C [SEQ ID NO:3]. All the fusion proteins described in this Example were derived from this construct. The DNA sequence encoding the gp33 peptide was cloned at the 3' end of the PapMV CP gene in the BamHI site.

Expression and Purification of Recombinant Proteins from *E. coli*

The *E. coli* expression strain BL21(DE3) RIL (Stratagene, La Jolla, Calif., USA) was transformed with the plasmid pET-3d containing either of the different constructs, and maintained in 2×YT medium containing ampicillin (50 µg/ml). Bacterial cells were grown at 37° C. to an optical density of 0.6 at 600 nm and protein expression was induced with 1 mM isopropyl-β-D-thiogalactopyranoside (IPTG). Induction was continued for 16 h at 25° C. Bacteria were harvested by centrifugation for 15 minutes at 6000 rpm. The pellet was resuspended in ice-cold lysis buffer (50 mM Na H$_2$PO$_4$ [pH 8.00], 300 mM NaCl, 10 mM imidazole, 20 µM PMSF, 1 mg/ml lysosyme) and bacteria were lysed by sonication. The lysate was centrifuged twice for 30 minutes at 13,000 rpm to eliminate cellular debris. The supernatant was incubated with 1 ml of Ni-NTA (Qiagen, Turnberry Lane, Valencia, Calif., USA) under gentle agitation for 4 h at 40° C. Lysates were loaded onto a column and the beads were washed with 3×15 ml of washing buffer (50 mM Na H$_2$PO$_4$ [pH 8.00], 300 mM NaCl) containing increasing concentrations of imidazole (10 mM, 20 mM and 50 mM). The beads were then washed with 15 ml of working buffer (10 mM Tris-HCl pH 8 or 10 mM NaP buffer pH 7.2). Proteins were eluted in working buffer containing 1 M imidazole. The purity of the proteins was determined by SDS-PAGE and confirmed by Western immunoblot analysis using rabbit polyclonal antibodies generated against purified PapMV virus.

Electron Microscopy

VLPs or viruses were diluted in 10 mM Tris-HCl pH 8 and were absorbed for 3 minutes on a carbon-coated formvar grid. The grid was then washed 3 times for 1 minute. The grid was finally drained to evacuate all the residual buffer and used directly for observation at the electron microscopy (EM).

SDS-PAGE and Electroblotting

Proteins were mixed with ⅓ of the final volume of loading buffer containing 5% SDS, 30% glycerol and 0.01% bromophenol blue. SDS-PAGE was performed as described elsewhere (Schägger and von Jagow, 1987, *Anal. Biochem.* 166, 368-379).

Results

In order to analyse MHC class I associated presentation of virus-like particles (VLPs) containing the immunodominant epitope (gp33 peptide: TSGGGKAVYNFATC-6H [SEQ ID NO:8]) of LCMV (PapMV-gp33) in vitro and in vivo, PapMV VLPs were genetically engineered with the gp33 epitope by making a fusion to the C-terminus of the PapMV coat protein (CP) open reading frame. Upon expression of the recombinant chimeric protein in E. coli, production of VLPs similar to the WT CP were observed indicating that the fusion did not affect the assembly of the CP subunit in VLPs in bacteria. The chimeric VLPs were similar in size and in structure to the WT protein. A second chimeric protein containing the gp33 epitope with 3 amino acids flanking each end (N and C terminus) of the LCMV epitope (TSGGG TSIKAVYNFATCGILTR-6H [SEQ ID NO:9]) was also generated (PapMV-gp33-6aa. These VLPs could also assemble in virus-like particles.

Example VI

Processing and Cross-Presentation of the gp33 CTL Epitope Expressed on PapMV VLPs to Specific T Lymphocytes by Dendritic Cells in vitro Spleen cells from C57BL/6 mice were washed with RPMI medium and treated with mitomycin C according to the manufacturer's instructions (SIGMA). CD11c$^+$ dendritic cells (DCs) to be used as antigen presenting cells were purified by autoMACS using CD11c-specific magnetic beads (Miltenyi Biotech). $5 \times 10^4$ CD11c$^+$ cells/well were plated in round bottom microtiter plates in triplicates and pulsed with different quantities of PapMV, PapMV-gp33 or PapMV-gp33-6aa (as described in Example V) for 8 h at 37° C. Responder cytotoxic T lymphocytes (CTLs) were purified from spleen cells taken from gp33-specific TCR transgenic P14 mice (Kyburz, et al., 1993, Eur. J. Immunol. 23:1956-1962) using autoMACS sorting with CD8-specific magnetic beads (Miltenyi biotech). $1 \times 10^6$ purified CD8+ T cells were added to each well containing pulsed DCs and incubated for 48 h at 37° C. CTL proliferation was then measured by BrdU incorporation according to the manufacturer's instructions (Roche). Plates were read on a Luminoskan ascent reader (Thermo electron corp.).

Results

Figure 8:
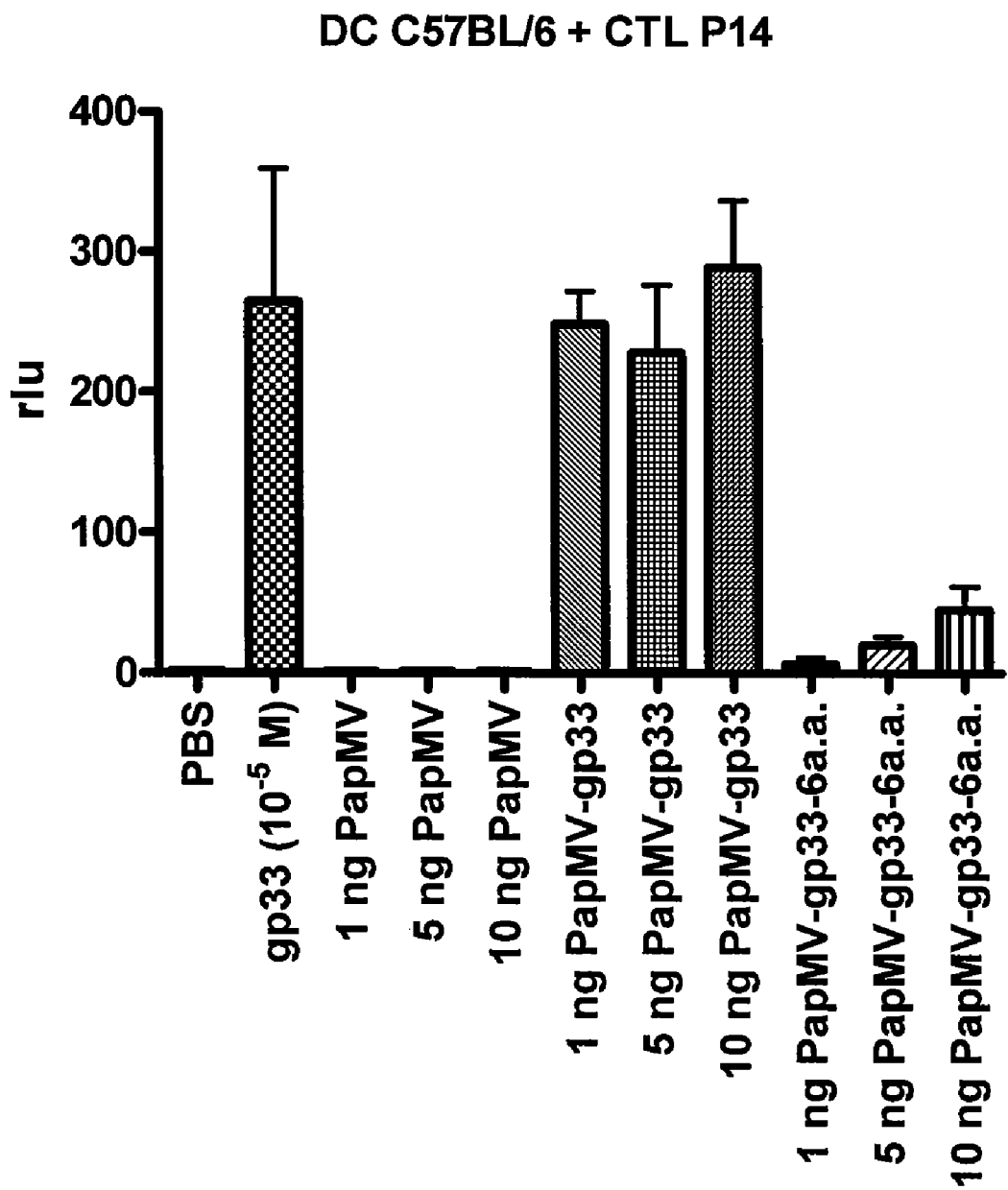
FIG. 8 illustrates that dendritic cells (DCs) process and present the p33 peptide of LCMV from recombinant PapMV virus-like particles (VLPs) expressing the p33 peptide (PapMV-gp33 and PapMV-gp33-6aa) to specific cytotoxic T lymphocytes; proliferation is expressed as relative light units (rlu) [PBS, phosphate buffered saline-pulsed DCs (negative control); gp33, gp33 peptide-pulsed DCs (positive control); PapMV, control PapMV; PapMV-gp33, PapMV VLP expressing the gp33 CTL epitope found in the LCMV glycoprotein sequence, and PapMV-gp33-6aa, PapMV VLP expressing the gp33 CTL epitope flanked by the 3 adjacent amino acids found in the LCMV glycoprotein sequence].

To determine whether the gp33 CTL epitope expressed on PapMV VLPs can be efficiently internalized, processed and cross-presented on MHC-I molecules, purified CD11c$^+$ DCs were pulsed in vitro with different quantities of PapMV VLPs (without fusion), PapMV-gp33 and PapMV-gp33-6aa and their capacity to stimulate the proliferation of gp33-specific TCR transgenic T cells was measured by BrdU incorporation (FIG. 8). Intense proliferation of gp33-specific T cells was induced by DCs pulsed with as little as 1 ng of PapMV-gp33 VLP whereas no significant proliferation was observed even with up to 10 ng of control PapMV. PapMV displaying the gp33 epitope flanked by the 3 adjacent amino acids found in the natural LCMV glycoprotein sequence was less efficiently processed and presented by DCs as indicated by the lower proliferation of gp33-specific CTLs induced by DCs pulsed with PapMV-gp33-6aa.

Example VII

Figure 9:
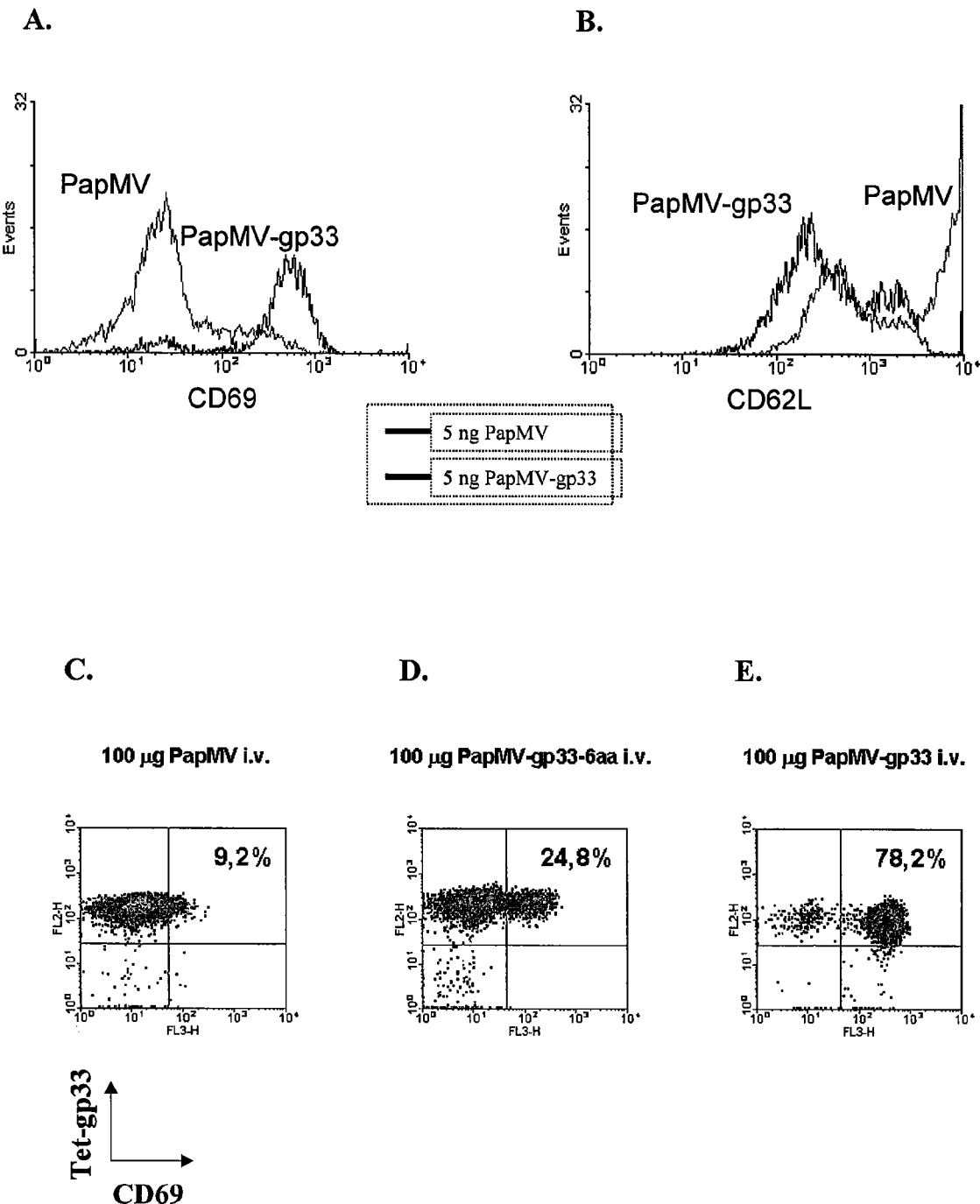
FIG. 9 presents the results of flow cytometry analysis of In vitro stimulation of purified CD8+ p33 tetramer positive T lymphocytes isolated from CD14 mice showing (A) the increase at the surface of the CD8+ p33 tetramer positive cells of the CD69 receptor upon activation with PapMV-gp33 VLPs (displacement to the right as compared to PapMV VLPs which could not increase the CD69 receptors at the surface of the CD8+ p33 tetramer positive cells, and (B) that the level of CD62L was similar with both treatments. Also shown is CD69 upregulation on CTLs isolated from mice immunized with (C) PapMV, (D) PapMV VLP fused to the gp33 CTL epitope flanked by the 3 adjacent amino acids found in the LCMV glycoprotein sequence, and (E) PapMV VLP fused to the gp33 CTL epitope; plots were gated on CD8$^+$ splenocytes and show the percent of tetramer and CD69$^+$ cells.

Cross-Presentation of the gp33 CTL Epitope by PapMV VLPs to gp33-Specific CTLs in vivo The ability of PapMV-gp33 (as described in Example V) to be processed and cross-presented to CTLs in vitro is shown in FIGS. 9A & B. CD8+ p33 tetramer positive T lymphocytes were isolated from CD14 mice. The cells were stimulated with 5 ng of PapMV VLPs or 5 ng of PapMV-gp33 VLPs harboring the p33 peptide at their surface. Flow cytometry analysis showed an increase at the surface of the CD8+ p33 tetramer positive cells of the CD69 receptor upon activation with PapMV-gp33 VLPs (displacement to the right in FIG. 9A). PapMV VLPs could not increase the CD69 receptors at the surface of the CD8+ p33 tetramer positive cells. The level of CD62L was similar with both treatments (FIG. 9B).

For in vivo studies, gp33-specific TCR transgenic P14 mice (Kyburz, et al., 1993, Eur. J. Immunol. 23:1956-1962) were immunized with 100 µg of PapMV, PapMV-gp33 by i.v. injection. 24 h later, spleen cells were isolated and labeled with PE-labeled gp33-specific tetramers, FITC-labeled anti-CD8 antibodies and PerCP-Cy5.5-labeled anti-CD69 antibodies (BD Pharmingen) and analyzed by flow cytometry on a FACS Calibur instrument (BD).

Results

To determine the capacity of PapMV VLPs to be processed and cross-presented to CTLs in vivo, gp33-specific TCR transgenic P14 mice were immunized with 100 µg of PapMV or PapMV-gp33 by i.v. injection. Twenty four hours after injection, spleen cells were isolated and labelled with gp33-specific tetramers, anti-CD8 and anti-CD69 antibodies followed by flow cytometry analysis (FIG. 9B). CD69 is an early activation antigen expressed on CD8$^+$ T cells and its upregulation correlates with the activation of antigen-specific T cells. Injection of 100 µg of PapMV-gp33 induced CD69 upregulation on almost 80% of gp33-specific CTLs whereas less than 10% expressed CD69 following immunization with control PapMV (FIG. 9B). Consistent with the data presented in FIG. 8, PapMV-gp33-6aa induced a partial activation of gp33-specific CTLs indicating that this preparation is less efficiently processed and presented.

Example VIII

Vaccination with PapMV VLPs Fused to the gp33 CTL Epitope Generates gp33-Specific CTLs To determine the ability of PapMV VLPs to induce the generation of specific CTLs, C57BL/6 mice were immunized with 100 µg of PapMV, PapMV-gp33 or PapMV-gp33-6aa (as described in Example V) by i.v. injection and boosted 20 days later with an identical preparation. Five days following the booster injection, spleen cells were isolated and labeled with PE-labeled gp33-specific tetramers and FITC-labeled anti-CD8 antibodies (BD Pharmingen) and analyzed by flow cytometry on a FACS Calibur instrument (BD).

Figure 10:
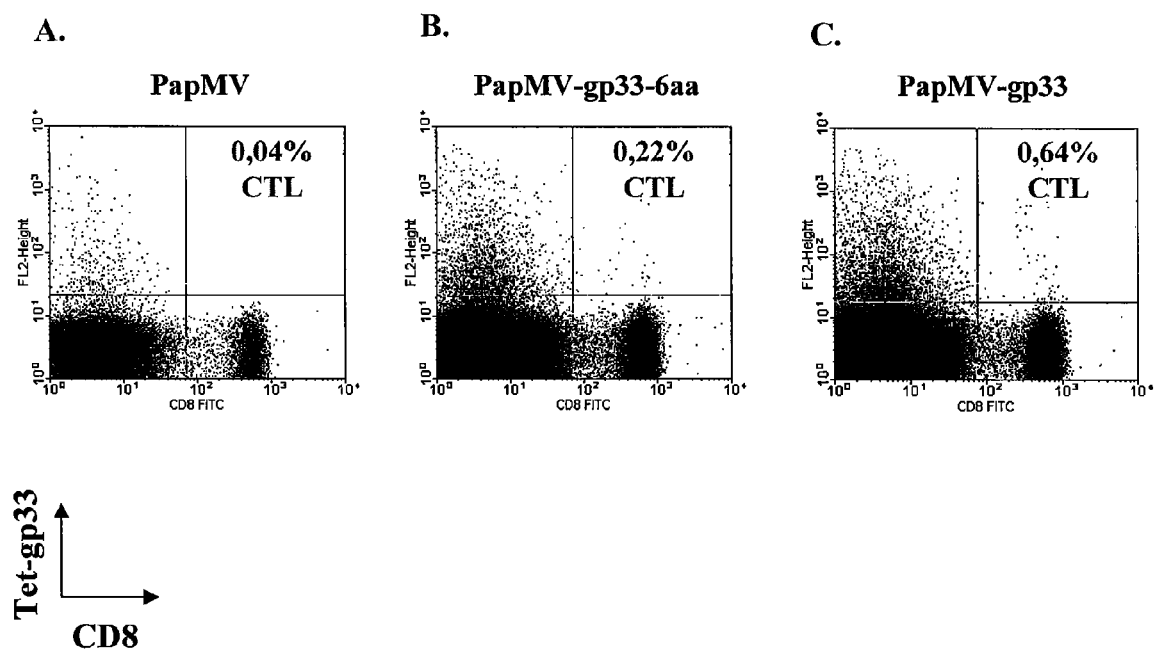
FIG. 10 presents the results of gp33 tetramer staining of CTLs isolated from C57BL/6 mice vaccinated with (A)

Results are shown in FIG. 10. Whereas vaccination with control PapMV induced few gp33-tet$^+$ CTLs, mice immunized with PapMV VLPs expressing the gp33 CTL epitope developed significant and reproducibly detectable gp33-specific CTLs. Again, PapMV-gp33-6aa induced a significant gp33-specific response but with a lower efficiency then PapMV-gp33.

The data presented in Examples V-VIII above demonstrate that PapMV VLPs are able to cross-present a CTL epitope on MHC class I molecules to CTLs. The data shows that cross priming occurs in vitro on DC as well as in vivo. Indicating that the PapMV VLPs are suitable for use to induce CTL responses toward other specific CTL epitopes.

Example IX

Induction of a Humoral Immune Response by PapMV VLPs Fused to an Epitope from the Surface Glycoprotein of MHV-A59

PapMV VLPs containing an epitope from the S surface glycoprotein of mouse hepatitis virus (MHV)-A59 following the basic protocol outlined in Example V. Subcutaneous injection of PapMV-MHV-A59+adjuvant (ACF) in mice resulted in production of anti-PapMV and anti-MHV-A59 IgGs (FIG. 11; the arrow indicates the administration of a booster injection at day 20). PapMV-MHV-A59 was also able to protect mice challenged with a lethal dose of MHV. As shown in FIG. 12, mice immunized and boosted 20 days later with 100 μg of PapMV-MHV-A59+ACF s.c. survived administration of MHV-A59 in an amount normally lethal to non-vaccinated mice.

Example X

Effect of Mutations K97A and E128A on RNA Binding and Self-Assembly of PapMV Coat Protein An E128A mutation was introduced by PCR into the CPΔN5 PapMV gene (prepared as outlined in Example V) as follows. Two small PCR products were first generated using the forward (E128A) primer (SEQ ID NO:16—see Table 1) with the CPΔN5 reverse primer (SEQ ID NO:7) and the forward (CPΔN5) primer (SEQ ID NO:6) with the reverse (E128A) primer (SEQ ID NO:17—see Table 1). These two PCR products were ligated together by PCR using the forward and the reverse primer at each end of the CPΔN5 construct and cloned in pET-3d using the NcoI-BamHI restriction sites as described above to generate a clone expressing the E128A recombinant protein. The clones K97A, R104K105R108/A, R118D120K121/A, K133K137/A, D142D145/A, E148A, R161A and E166E168/A were generated using the same approach as E128A. The primers used for the various PCRs are shown in Table 1.

TABLE 1

Primers used to introduce mutations in the PapMV CP by PCR for amplification of the mutated forms of the CP.

| Primer Name | Sequence | SEQ ID NO |
|---|---|---|
| K97A Forward | GCACAATTGGCTAGTATTGTCGCAGCTTCCGGCACTTCCCTT | 10 |
| K97A Reverse | AAGGGAAGTGCCGGAAGCTGCGACAATACTAGCCAATTGTGC | 11 |
| R104-K105-R108/A Forward | GCTTCCGGCACTTCCCTTGCAGCATTCTGCGCGTACTTCGCGCCAATA | 12 |
| R104-K105-R108/A Reverse | TATTGGCGCGAAGTACGCGCAGAATGCTGCAAGGGAAGTGCCGGAAGC | 13 |
| R118-D120-K121/A Forward | ATAATCTGGAATCTGGCGACGGCCGCAATGGCTCCTGCCAATTGG | 14 |
| R118-D120-K121/A Reverse | CCAATTGGCAGGAGCCATTGCGGCCGTCGCCAGATTCCAGATTAT | 15 |
| E128A Forward | GCTCCTGCCAATTGGGCGGCTTCAGGATACAAG | 16 |
| E128A Reverse | CTTGTATCCTGAAGCCGCCCAATTGGCAGGAGC | 17 |
| K133-K137/A Forward | GCCTCAGGATACGCACCAAGCGCCGCCTTTGCCGCGTTC | 18 |
| K133-K137/A Reverse | GAACGCGGCAAAGGCGGCGCTTGGTGCGTATCCTGAGGC | 19 |

TABLE 1-continued

Primers used to introduce mutations in the PapMV CP by PCR for amplification of the mutated forms of the CP.

| Primer Name | Sequence | SEQ ID NO |
|---|---|---|
| D142-D145/A Forward | TTTGCCGCGTTCGCCTTCTTCGCCGGGGTGGAGAAT | 20 |
| D142-D145/A Reverse | ATTCTCCACCCCGGCGAAGAAGGCGAACGCGGCAAA | 21 |
| E148A Forward | TTCTTCGACGGGGTGGCGAATCCGGCGGCCATG | 22 |
| E148A Reverse | CATGGCCGCCGGATTCGCCACCCCGTCGAAGAA | 23 |
| R161A Forward | CAACCCCCTTCGGGACTAATCGCGTCGCCGACCCAGGAAGAGCGG | 24 |
| R161A Reverse | CCGCTCTTCCTGGGTCGGCGACGCGATTAGTCCCGAAGGGGGTTG | 25 |
| E166-E167-R168/A Forward | CTAATCAGGTCGCCGACCCAGGCAGCGGCGATTGCCAATGCTACCAACAA | 26 |
| E166-E167-R168/A Reverse | TTTGTTGGTAGCATTGGCAATCGCCGCTGCCTGGGTCGGCGACCTGATTAG | 27 |
| Amorces communes N-terminus Forward | ATCGCCATGGCATCCACACCCAACATAGCCTTCCCCGCCATCACC | 28 |
| Amorces communes C-terminus Reverse | ATGCGGATCCTTACTAATGGTGATGGTGATGGTGTTCGGGGGTGGAAG | 29 |

The constructs described above were expressed in *E. coli* expression strain BL21(DE3) RIL (Stratagene, La Jolla, Calif., USA) as described in Example V. SDS-PAGE and electroblotting was also conducted as described in Example V.

Electron Microscopy and Immunogold Labeling

VLPs or viruses were diluted in 10 mM Tris-HCl pH 8 and were absorbed for 3 minutes on a carbon-coated formvar grid. Grids were blocked with 8 mL of BSA (10 mg/mL) for 30 seconds and washed with PBS. Grids were incubated for 30 minutes at room temperature with a rabbit anti-6×H tag antibody (Amersham, Pittsburgh, Pa., USA) diluted 1:10 in PBS. Grids were then washed three times with PBS and incubated at room temperature for 30 minutes with donkey anti-rabbit antibodies conjugated with 6 nm gold particles (Jackson Immuno Research, West Baltimore Pike, West Grove, Pa., USA) and diluted 1:20 in PBS. Grids were then washed with deionized water and stained as described above.

Circular Dichroism Spectroscopy

CD spectra were recorded on an Olis RSM 1000 (Olis, Conway DriveSuites A & B, Bogart, Ga., USA) rapid scanner monochromator at 20° C. For far UV CD (260-190 nm), thermostated quartz cells of 0.1 cm path length were used. Mean residue ellipticity values ([6]mR$_w$ in degxcmzxdmol) were calculated using the equation: $[6]MR_w=[6]*MRW/(10 \times c \times l)$, where [6] is the ellipticity in degrees, MRW is the average molecular weight of the residues in the protein (108 was used in this study), c is the protein concentration in g/ml and l is the path length in cm (Johnson, W. C. (1996) Circular Dichroism Instrumentation in *Circular Dichroism and the Conformational Analysis of Biomolecules* (Fasman, G. D., ed) pp. 635-652, Kluwer Academic/Plenum Publishers).

Near UV CD spectra were recorded (250-350 nm) at RT in a Jasco Model J-710 instrument (Jasco, Commerce Dr. Easton, Md., USA). Recordings were made using a quartz cuvettes (pathlength 0.1 cm). Spectra were averaged from 10 scans of 0.2 nm steps at a rate of 100 nm/min. Rods and Disks samples were respectively at concentration of 1.5 mg/ml and 5.5 mg/ml.

RNA Transcripts and Electrophoretic Mobility Shift Assay (EMSA)

The RNA probe was generated by transcription in vitro using a RiboMAX™ Large Scale RNA Production System-T7 kit (Promega P1300, Madison, Wis., USA) and a clone of 80 nt of the 5' of PapMV in front of the T7 promoter. The clone was linearised with EcoRI before in vitro transcription. The RNA transcript was purified on a G50 Quick Spin Column for DNA/RNA purification (Roche 1273 965). The same method was used to generate a transcript of the 5' 1800 nucleotides of PapMV for the in vitro assembly assay. The RNA probe was dephosphorylated using shrimp alkaline phosphatase (Fermentas, Hanover, Md., USA, EFO511) and labelled with gamma $^{32}$P-ATP using T4 polynucleotide kinase (NEB, Ipswich, Mass., USA, M0201 S). The probe was then purified using the G-50 Quick Spin Columns as before. Labelled RNA was incubated with recombinant proteins at room temperature for 60 minutes. 165 fmol of RNA were used for each reaction and various amounts of purified recombinant proteins in the in vitro assembly buffer, which contained 7.5 U of RNase inhibitor (Amersham Biosciences 27-0816O1). The final volume of the reaction was 10 µL; 2 µL of loading dye was added to the sample before loading onto a 5% native polyacrylamide gel. Electrophoresis was performed in 0.5× Tris-borate-EDTA buffer for 90 minutes at 10 mA. The gel was dried and subjected to autoradiography for 16 hours on Kodak BioMax MS film (Amersham Biosciences V8326886) and developed.

Purification of PapMV and Isolation of Disks

PapMV was purified by differential centrifugation from infected papaya leaves that showed mosaic symptoms. Infected leaves (100 g) were ground in 100 mL 50 mM Tris-HCl (pH 8.0) containing 10 mM EDTA in a commercial blender. The ground leaves were filtered through cheesecloth, 1% of Triton X-100 was added to the filtrate, and the filtrate was stirred gently for 10 min. Chloroform was added drop by drop to a volume equivalent to one-quarter of the volume of the filtrate. The solution was stirred for an additional 30 min at 4° C. and centrifuged for 20 min at 10000 g to remove the precipitate. The supernatant was subjected to high-speed (100 000 g) centrifugation for 120 min. The viral pellet was suspended and subjected to another high-speed centrifugation through a sucrose cushion (30% sucrose) at 100 000 g for 3.5 h. The final viral pellet was suspended in 10 mL of 50 mM Tris (pH 8.0). If color persisted, an additional clarification with chloroform was performed. The purified virus was collected by ultracentrifugation. The isolation of the disks by acetic acid degradation method was performed as described previously (Erickson, et al., 1976, Virology. 72, 514-7).

Trypsin Digest

10 µg of protein was incubated at 370° C. in a volume of 50 µl for 120 minutes in a 100 mM tris HCl buffer pH 8.5 with 0.2 µg of trypsin (Roche, Indianapolis, Ind., USA, 1418475). The reaction was stopped by addition 10 µL of loading dye containing 5% SDS, 5 mM DTT and 40% glycerol. The sample was boiled 5 minutes prior loading on a SDS-PAGE gels. The proteins were visualised by Coomassie blue staining.

Results

Alignment of the amino acids sequences of 19 potexviruses CPs between amino acid 90 to 169 of PapMV CP revealed a consensus sequence as shown in FIG. 13A. The amino acid corresponding to position 128 of the PapMV CP is an A in most potexviruses (underlined), an E in three different potexviruses including PapMV (bold), and T, V, S or Q occur in this position in the other 5 potexvirus sequences. The consensus was made using the CP sequences of BaMV: Bamboo mosaic virus; P1AMV: Plantago asiatica mosaic virus; TVX: Tulip virus X; CsCMV: Cassava common mosaic virus; C1YMV: Clover yellow mosaic virus; HVX: Hosta virus X; LVX: Lily virus X; CymMV: Cymbidium mosaic virus; PAMV: Potato aucuba mosaic virus; NMV: Narcissus mosaic virus; PepMV: Pepino mosaic virus; FoMV: Foxtail mosaic virus; ScaVX: Scallion virus X; WC1MV: White clover mosaic virus; SMYEV: Strawberry mild yellow edge virus; PVX: Potato virus X; AltMV: Alternanthera mosaic virus; CVX Cactus virus X; PapMV: Papaya mosaic virus.

The identified consensus sequence shows the charged residues R104, K133, K137, and R161 believed to be involved in an interaction with the genomic RNA and play an important role in assembly and packaging of the viral genome (Abouhaidar, & Lai, 1989, J. Gen. Virol. 70, 1871-5). It also contains acidic residues that could be important for the interaction with the genomic RNA, as shown for Tobacco mosaic virus (TMV) CP (Stubbs, G., 1999, Trans. R. Soc. B. Biol. Sci. 354, 551-7). Based on these observations, charged residues in the region 91 to 169 were selected as candidates for site specific mutagenesis.

The PapMV CP harbours two M residues at positions 1 and 6 of the CP open reading frame (ORF). It is not clear if both of these initiation codons are used during replication of the virus. However, it has been shown that a large proportion of the CP of the purified virus lacks several amino acids at the N-terminus (Zhang, et al., 1993, J. Mol. Biol. 234, 885-7). To ensure production of only one open reading frame in E. coli, the N-terminal 5 amino acids were removed such that $M^6$ served as an initiation codon. The introduction of the initiation codon in the NcoI site introduced an extra A that is found in all the constructs. A 6×H tag was added at the C-terminus of the protein to facilitate the purification process. The recombinant protein CPΔN5 was expressed in E. coli BL21 (pLysS) and showed a slightly larger molecular weight (MW) than that of WT CP extracted from purified virus (see FIG. 13B, lane 3 and 8). The difference observed between the two proteins is probably caused by the 6×H tag fusion at the C-terminus. The recombinant protein was affinity purified using a $Ni^{2+}$ column and eluted using 1M imidazole (FIG. 13B, lane 3). The yield of the purified recombinant protein was estimated at 40-50 mg/L. Western blot assay using an antibody raised against the WT PapMP CP confirmed that the purified protein was indeed PapMV CP (FIG. 13, lane 9).

Nine different mutants were generated that harbour one, two or three A substitutions. Five mutants R118-D120-K121/A, K133-K137/A, D142-D145/A, R161A and E166E167-R168/A produced unstable proteins and were undetectable or expressed at very low level. It is likely that mutagenesis in this conserved region affected the native folding of the CP. The mutants K97A, R104K105R108/A, E128A and E148A could be expressed to level similar to CPΔN5 and easily purified using a 6×H tag as shown with the CPΔN5. However, the removal of imidazole during the dialysis made the mutants R104K105R108/A and E148A aggregate and precipitate and it is likely that the mutations affected the folding of the protein. Results of the expression and purification of recombinant CP4N5, K97A, R104K105R108/A, E128A and E148A is shown in FIG. 13B. Lanes 1-7: Coomassie staining profile of the recombinant proteins. lane 1: E. coli lysate before induction of CPΔN5, lane 2: E. coli lysate of CPΔN5

16 hours post-induction with 1 mM IPTG, lane 3: recombinant CPΔN5 purified using a Ni$^{2+}$ column; lane 4: purified K97A, lane 5: purified R104K105R108/A lane 6: purified E128A lane 7: purified E148A, lane 8: PapMV CP from virus purified from plants. Lanes 9-14: Western blotting of purified recombinant proteins revealed with IgG directed against PapMV CP. Lane 9: Purified CPΔNS, lane 10: purified K97A, lane 11: R104K105R108/A, lane 12; E128A, lane 13; E148A and lane 14: purified virus from infected plants.

The construct CPΔN5 self assembled into VLPs in *E. coli* as shown by the electron micrograph of the purified recombinant protein. The VLPs were similar in shape and in diameter to the native virus particles. To analyse and quantify the proportion of the purified protein that was found as VLPs, VLPs and smaller aggregates were separated by ultracentrifugation at 100,000 g for 2 hours. Most of the CPΔN5 proteins (80%) were found in the supernatant. VLPs were found in the pellet and account for 20% of the total purified recombinant protein. However, the purified protein K97A remained in the supernatant after ultracentrifugation. On the contrary, the recombinant protein E128A was found totally in the pellet after ultracentrifugation.

Electron microscopy revealed that E128A VLPs isolated from the high speed pellet are similar to the WT virus. The length of 150 VLPs for each CPΔN5 and E128A was measured and the average length was determined. CPΔN5 VLPs appeared 10 times shorter (50 nm) than the native virus that is 500 nm in length as predicted. However, E128A VLPs are approximately 3 times longer than CPΔN5 VLPs suggesting that this mutant can more efficiently support the initiation and elongation of assembly. Finally, an electron micrograph of the purified K97A protein revealed disorganised aggregates of 15 to 50 nm in diameter. The outline of the aggregates was irregular showing that this protein can not organise itself into VLPs.

The purification of the VLPs using the Ni$^{2+}$ column was efficient suggesting that the 6×H tag is located at the surface and available for interaction with the affinity column. To confirm this hypothesis, an immunogold labelling experiment was performed on CPΔN5 VLPs using anti-6×His tag rabbit antiserum followed by a secondary donkey anti-rabbit labelled with gold particles. As expected, the VLPs were decorated with the gold particles, thus demonstrating that the fusion of a peptide (6×H) to the C-terminus is tolerated and exposed to the surface of VLPs. This surface exposure of C-terminally fused peptides demonstrates the suitability of the C-terminus as an appropriate point to which to attach an immunogen.

Circular dichroism (CD) spectrophotometry was used to compare the secondary structure of the recombinant proteins with the WT virus. The secondary structure of CPΔN5 was estimated to be 49% α-helices and 15% random coil. The CD spectra of CPΔN5 VLPs and WT virus showed a slightly different profile (FIG. 14A). The CD signal measured at 208 nm was more pronounced for the WT virus than the CPΔN5 VLPs (FIG. 14A). Interestingly, the CD signal measured with E128A VLPs at 208 nm superimposed with the WT virus (FIG. 14A).

The CD signal of the isolated disks (high speed supernatant of the purified protein) of CPΔN5 was identical to isolated disks from the purified virus using the acetic acid method (FIG. 14B). It is interesting to notice that the CD signal measured with disks in general at 208 nm was less pronounced than with VLPs. This result suggests that the content in α-helices is increased when the disks assemble in VLPs. Finally, the folding of the purified protein of K97A was compared with high speed supernatant of CPΔN5. Both proteins showed an identical CD profile (FIG. 14E).

Spectra between 250 and 350 nm were also obtained to measure the absorption of aromatic residues and tryptophan residues in the protein. A change in the environment of those residues affects the signal recorded and indicates variation in the tertiary structure. The VLPs of CPΔN5 and E128A appeared to be similar (FIG. 14D), indicating that the tertiary structures are the same for both VLPs. The spectra of CPΔN5 disks and K97A were very similar which suggests that both proteins have a similar tertiary structure (FIG. 14E). The slight differences in the intensity of the curves between the samples were probably due to a small variation in protein concentrations.

80% of the purified recombinant CPΔN5 and all the K97A proteins were found as multimers (disks) in the supernatant after ultracentrifugation. To measure the level of multimerisation of these proteins, the high speed supernatant of CPΔN5 and the purified protein K97A were analsed using Superdex™ 200. For CPΔN5, most of the proteins were eluted as a high molecular weight complex of 450 kDa (FIG. 15A) which corresponds to a multimer of approximately 20 subunits (molecular weight of the protein subunit is 23 kDa). The second peak eluting at 81.27 ml was collected and loaded on a Superdex™ 75 column to improve the resolution. The protein eluted as a 39 kDa protein. A sample from this peak was submitted to SDS-PAGE and showed a unique band; smaller than CPΔN5 that corresponds to a degradation product of CPΔN5. It is possible that this degraded protein is unable to form a high molecular complex and remains as a dimer in solution.

The elution profile of K97A can be divided in 3 major peaks (FIG. 15B). The second peak was eluted at 50 ml and overlapped with the CPΔN5 disks (FIG. 20A) which probably corresponds to the disk structure. The first peak eluted between 41 and 43 ml and corresponds to aggregated material that is greater than 700 kDa in size. The elution pattern is wide and shows a shoulder that suggests that this material is not uniform and may correspond to an aggregate of K97A disks agglutinated together by non specific interactions. The third peak was not analysed further and probably corresponds to a truncated protein as shown for the CPΔN5 construct. These results confirm that K97A is able to form disks with other protein subunits but is unable to assemble into VLPs in *E. coli*.

CPΔN5 disks were isolated from the high speed supernatant of the purified proteins by affinity chromatography and used for an in vitro assembly assay. Disks of a diameter of 17 nm were isolated by gel filtration. 50 ml of CPΔN5 disks at a concentration of 1 mg/ml were incubated with 0.05 mg of RNA for 30 minutes at room temperature. Electron microscopy demonstrated that the RNA and the protein were assembled into VLPs of regular length (150 nm) that correspond to the length of the RNA (5' 1800 nt of PapMV) used for the in vitro assembly assay. This result demonstrates clearly that disks of approximately 20 subunits are the building blocks of the VLPs in vitro. The purified K97A recombinant protein failed to assemble the RNA in VLPs under these conditions.

The K97A and E128A mutations showed completely opposite effects on the PapMV CP. To evaluate if CPΔN5 and E128A VLPs contain RNA, the 280/260 ratio of the different VLPs was measured on the spectrophotometer and compared with the proteins of the purified virus (Table 2). As expected, the VLPs showed a smaller 280/260 ratio than disks because of their lower level of RNA. The 280/260 ration of the E128A VLPs was comparable to the purified virus. Interestingly, this ratio was 50% higher with CPΔN5 VLPs. The 280/260 ratio of the isolated disks of CPΔN5 and K97A was comparable to the disks extracted with acetic acid of the purified virus.

TABLE 2

OD 280/260 for PapMV VLPs

| Virus or VLP | | | Discs extracted from: | | |
|---|---|---|---|---|---|
| Purified PapMV | CPΔN5 VLP | E128A VLP | Purified PapMV | CPΔN5 VLP | E128A VLP |
| 0.75 | 1.10 | 0.75 | 1.5 | 1.64 | 1.55 |

To evaluate if the ability to make VLPs was directly related to the affinity of CP for RNA, disks from CPΔN5 and the E128A mutants were isolated and compared to K97A. The high speed supernatant of CPΔN5 was used for isolation of the 450 kDa multimer (disks). Since the E128A mutant makes only VLPs in *E. coli*, these were disrupted using acetic acid treatment and E128A disks were isolated (Abouhaidar, & Bancroft, 1978, *Virology*. 90, 54-9). Different amount of disks were incubated in a volume of 10 μl containing 165 fmol of a $^{32}$P-labelled RNA probe made from a transcript of 80 nucleotides of the 5' non coding region of PapMV. The protein-RNA complex was separated by an electrophoresis mobility shift assay (EMSA). The disks of CPΔN5 interacted with the probe in a cooperative manner and induced a shift with 500 ng (22 pmol) of proteins. This result shows that the CPΔN5 disks, which are free of RNA after isolation, are able to interact with RNA in vitro only when a molar ratio of 1,000 (disks/RNA) is reached which, corresponds to a weak affinity for RNA. When a similar experiment was performed with the isolated disks of the mutant E128A and the same probe, the E128A disks bound RNA more efficiently than CPΔN5. As little as 50 ng of protein was sufficient to create a protein RNA complex. Purified K97A proteins in the same conditions failed, even at higher concentration (up to 1500 ng) to induce the formation of a protein RNA complex. The EMSA was repeated with RNAs extracted from CPΔN5 VLPs that were labelled as described previously and the same results were obtained with this RNA that do not contain the PapMV packaging signal.

To evaluate the stability of the VLPs and measure if the assembly of the disks into a rod structure improved the stability of the complex, their resistance to heat was monitored by CD spectrophotometry. CPΔN5 VLPs and the virus both resist to high temperature (over 60° C.) before showing any sign of fatigue (FIG. 16A). The purified PapMV was the most stable structure tested and could resist temperatures approaching 100° C. The temperature of inactivation reported for PapMV is 70° C. CPΔN5 VLPs were more sensitive than the WT virus probably due to the presence of the 6×His tag located at the C-terminus. The E128A VLPs appeared more sensitive to heat and showed sign of fatigue at 42° C. (FIG. 16A). Disks were rapidly denatured at 40° C. (FIG. 16B). This result suggests that the packing of the disks in the rod structure considerably improves stability.

Treatment of PapMV with trypsin results in a cleavage, presumably at amino acid 198 at the C-terminus. Under these conditions, the remaining protein was resistant to the protease. A similar assay was performed on the purified virion and recombinant VLPs and disks and indicated that PapMV did not seem to be affected by trypsin. Electron microscopy confirmed that treated virus was identical in appearance to untreated virus, however, both the isolated disks from CPΔN5 and the CPΔN5 VLPs were very sensitive to trypsin and several bands of lower molecular weight corresponding to degraded fragments were generated, suggesting that several positively charged residues are exposed and available at the surface of the VLPs. E128A showed similar resistance to trypsin as the WT virus.

Example XI

Production and Engineering of PapMV VLPs Fused to the gp33 CTL Epitope

Cloning of the Recombinant PapMV-p33 Construct

To fuse the LCMV p33 peptide at the C-terminus of CPΔN5 (cloned as described in Example V), the following oligonucleotides were prepared.

5'-CTAGTGGTGGCGGTCTGTTGCTGAAAGCGG    [SEQ ID NO: 30]
TGTATAACTTTGCGACCATGA-3',
and

5'-CGCGTCATGGTCGCAAAGTTATACACCGCT    [SEQ ID NO: 31]
TTCAGCAACAGACCGCCACCA-3'.

The two oligonucleotides were annealed in 10 mM Tris, pH 8 and 50 mM NaCl and used directly for cloning in the plasmid containing the sequence encoding the PapMV CPΔN5 CP linearized with SpeI and MluI. The p33 peptide was flanked by 3 leucine and 3 glycine residues at its N-terminus and 2 threonine and 1 arginine residues at the C-terminus. The insertion was positioned between the C-terminus of the PapMV CP and a 6×His tag (see FIG. 18A).

Expression and Purification of Recombinant Proteins from *E. coli*

The *E. coli* expression strain BL21 (DE3) RIL (Stratagene, La Jolla, Calif., USA) was transformed with the pET-3d plasmid containing the constructs of interest, and maintained in 2×YT medium containing ampicillin (50 mg/ml). Recombinant proteins were purified by affinity chromatography on a nickel sepharose column as previously described (22). Two additional washing steps were done sequentially using 10 mM Tris-HCl 50 mM Imidazole 0.5% Triton X100 pH8, and then 10 mM Tris-HCl, 50 mM Imidazol, 1% Zwittergent pH8 to remove endotoxin contamination. Protein purity was determined by SDS-PAGE and confirmed by immunoblot analysis using rabbit polyclonal antibodies specific to PapMV. LPS levels were determined by the limulus amebocyte lysate assay according to manufacturer's instructions (Cambrex Bio Science, Walkersville, Md.) and were always under 0.005 endotoxin units (EU)/μg of protein.

Electron Microscopy

VLPs were diluted in 10 mM Tris-HCl pH 8 and were absorbed for 3 min on a carboncoated formvar grid. The grid was then washed 3 times for 1 min using the same buffer and stained with 0.1% uranyl acetate for 10 min at room temperature. The grids were then observed on a Jeol JEM220FS transmission electron microscope.

Results

Bacterial expression of control PapMV CP or PapMV-p33 yielded 29 kDa proteins. Extensive washes were performed to remove all traces of LPS and VLPs were isolated by high-speed ultracentrifugation. Electron microscopy analysis revealed that PapMV-p33 VLPs displayed a rod-like structure similar to that of control PapMV VLPs suggesting that expression of foreign epitopes did not impair VLP formation.

Example XII

Dendritic Cell Internalization of PapMV VLPs and Acquired Maturation Phenotype Mice Female 6-10 week-old C57BL/6 mice were purchased from Charles River (Saint-Constant, Canada). P14 TCR-transgenic mice were obtained from P. Ohashi (Princess Margaret Hospital, Toronto, Canada). P14 mice express a transgenic Vα2 and Vβ8.1 TCR specific for the p33 CTL epitope from the LCMV surface glycoprotein; 70-90% of their CD8+ T cells are p33-specific.

Cells, Virus and Peptides

LCMV WE was obtained from R. M. Zinkernagel (Institute of Experimental Immunology, Zurich, Switzerland). The p33 synthetic peptide KAVYNFATM [SEQ ID NO:4] corresponding to a $H-2^b$-restricted CTL epitope from the LCMV surface glycoprotein was synthesized by Sigma-Genosys (Oakville, Ontario). EL-4 thymoma cells ($H-2^b$) were grown in MEM (Invitrogen Life Technologies, Burlington, Ontario) containing 10% heat-inactivated FBS (Invitrogen). MC57G fibroblasts were cultured in MEM containing 5% heat-inactivated FBS.

Antibodies and Flow Cytometry

For cytometry analysis of mouse surface antigens, the following mAbs were used: anti-CD4-FITC (clone H129.19), anti-CD8a-FITC (clone 53-6.7), anti-CD11c-FITC (clone HL3), anti-CD40-PE (clone 3/23), anti-CD45R-FITC (clone RA3-6B2), anti-CD69-PerCP-Cy5.5 (clone H1.2F3), anti-CD80-PE (clone 16-10A1), anti-CD86-PE (clone GL1), isotype controls for the anti-CD40 and anti-CD86 mAbs (Rat $IgG_{2a}$, ?) and anti-CD80 mAbs (Armenian Hamster IgG2, ?) (all from BD Biosciences, Mississauga, Ontario). FITC-coupled F4/80 mAb (clone BM8) was obtained from E-Bioscience (San Diego, Calif.). Stainings were performed for 20 min at 4° C. PE-coupled p33-$H-2^b$ tetrameric complexes (Tet-gp33) were synthesized and staining was performed for 20 min at 37° C. All cytometry analysis were performed on a FACScalibur cytometer (BD Bioscience) and data were analyzed using the WinMDI software.

Isolation of Splenic DCs

Spleens of C57BL/6 mice were treated with 400 U/mL collagenase type IV (Roche Diagnostics, Laval, Quebec) for 45 min at 37° C., 5% $CO_2$. Spleen cells were isolated by passing through a 100 µm cell strainer and incubated 20 min at 4° C. with CD11c-specific colloidal paramagnetic beads (Miltenyi Biotec, Auburn, Calif.) in pre-filtered running buffer (0.5% BSA in PBS). After washing the cells once with running buffer, CD11c$^+$ spleen cells were positively selected using an autoMACS system (Miltenyi Biotec). The purity of the positive fraction was always above 95%. Where indicated, the negative fraction was kept for subsequent analysis. CD11c+ cells were cultured in MEM 10% and were analyzed by flow cytometry after staining with FITC-coupled anti-mouse CD11c mAbs.

Capture Assay of PapMV-Like Particles

PapMV-like particles were labelled using an Alexa Fluor 647 Protein Labelling Kit (Molecular Probes, Eugene, Oreg.) according to manufacturer's instructions. Labelling efficiency was determined by spectrophotometry and was similar for both control and PapMV-p33 VLPs. For the in vivo capture assay, C57BL/6 mice were injected i.v. with 100 µg of labelled VLPs and CD11c$^+$ cells were purified from spleens 2 h post-injection. Samples from the negative fraction obtain after purification of splenic CD11c$^+$ cells were stained with FITC-coupled anti-mouse CD45R, F4/80, X? 8a or CD4 mAbs. For the in vitro capture assay, purified CD11c$^+$ spleen cells from C57BL/6 mice were pulsed 2 h with various concentrations (0.5, 1 or 5 µg) of Alexa Fluor 647-labelled VLPs.

Confocal Microscopy

For the in vivo internalization assay, mice were injected with 100 µg of Alexa Fluor 647-labelled VLPs i.v. and spleens were collected 2 h later. CD11c$^+$ spleen cells were adhered on slides coated with poly-L-lysine (Sigma-Aldrich) by centrifugation at 650 rpm for 1 min. Cells were fixed with 10% formalin for 20 min and labelled 45 min at room temperature with Alexa Fluor 488-conjugated wheatgerm agglutinin (Molecular Probes) as a membrane marker. After 3 washes with PBS, slides were mounted using ProLong Gold antifade reagent (Molecular Probes) and analyzed using a Zeiss LSM 510 META scanning confocal microscope mounted on an Axiovert 100 oil immersion objective (Carl Zeiss, Jena, Germany). Images were processed using the LSM 510 v3.2 software (Carl Zeiss). For the in vitro capture assay, purified CD11c$^+$ spleen cells from naïve C57BL/6 mice were incubated 2 h at 37° C. with different quantities (0.5, 1 or 5 µg) of Alexa Fluor 647-labelled VLPs. Cells were then washed, stained and analyzed as described above.

In vivo DCs Maturation Assay

C57BL/6 mice were immunized i.v. with 100 µg of control PapMV VLPs, PapMV-p33 VLPs or with 25 µg of LPS from *E. coli* serotype 5 (Sigma-Aldrich, Oakville, Ontario) as a positive control. At 2, 6 or 24 h post-injection, CD11c+ spleen cells were stained with FITC-coupled anti-mouse CD11c mAb in combination with PE-coupled anti-mouse CD40, CD80, CD86 or isotype control mAbs. Samples were acquired and analyzed by flow cytometry as described above.

Results

The capacity of various murine splenic cells to take-up PapMV VLPs labeled with Alexa-Fluor 647 in vivo was evaluated. The amount of VLPs associated with different cell types was determined by flow cytometry (FIG. 19) and indicated that all APCs (DCs, B cells and macrophages) were able to take-up labeled PapMV-p33 VLPs to varying extents but DCs were the most efficient with more than 40% of CD11c$^+$ cells being associated with PapMV-p33 labeled-VLPs. As expected, both CD4$^+$ and CD8$^+$ T cells did not significantly uptake VLPs. Interestingly, higher amounts of PapMV-p33 VLPs were associated with all APC types compared to control PapMV VLPs suggesting that the presence of the CTL epitope influences VLP uptake. To determine whether this is due to differences in VLP capture and/or internalization, splenic DCs were purified and pulsed in vitro for 2 h with labeled-VLPs and the levels of VLPs associated with DCs were determined by flow cytometry. Both VLPs associated with purified DCs with similar efficiency suggesting that differences observed in vivo were probably the result of different degradation or dissemination kinetics. Confocal microscopy analysis of sorted CD11c$^+$ DCs from VLP immunized mice confirmed that the fluorescently labeled material was mostly localized in the cytoplasm. Fluorescently labeled PapMV-p33 VLPs were mostly found in large vesicular structures in contrast to control PapMV particles that appeared more evenly distributed in the cytoplasm. This suggests that insertion of the p33 epitope in PapMV VLPs possibly modified their structure allowing them to be internalized by DCs in a more stable particulate form.

As mature DCs are the most efficient APC type capable of priming naive T cells, the ability of PapMV VLP uptake by splenic DCs to lead to DC maturation was evaluated. Six hours following i.v. immunization of C57BL/6 mice with PapMV VLPs, splenic CD11c$^+$ DCs were isolated by magnetic cell sorting and the upregulation of cosignaling molecules (CD40, CD80 and CD86) was determined by flow cytometry (FIG. 20). Both control PapMV and PapMV-p33 VLPs similarly induced significant upregulation of CD40 and CD86 suggesting that the presence of the p33 epitope does not affect this process. On the other hand, surface expression of CD80 was only slightly augmented. Similar results were obtained 24 h post injection with, however a slight increase in CD80 expression. To ensure that maturation was not resulting from traces of LPS contaminating the preparations, endotoxin levels in each purified VLP stocks was quantified using the limulus amebocyte lysate assay. The corresponding trace amounts of contaminating LPS were administered to C57BL/6 mice and cytometric analysis of cosignaling molecules expression levels on DCs revealed that such minute amounts of LPS had no significant effect on DC maturation. These results suggest that PapMV VLPs possess an intrinsic adjuvant-like property that induces DC maturation.

Example XIII

Cross-Presentation of the gp33 CTL Epitope by PapMV VLPs to gp33-Specific CTLs in vitro and in vivo T Cell Proliferation Assay For the in vitro assay, CD11c+ spleen cells were treated 2 h with mitomycin C (Sigma-Aldrich). Following three washes in MEM 5% FBS, $5 \times 10^4$ cells/well were added in 96-well round-bottom plates and pulsed 8 h with various concentrations (10, 100, 500 or 1000 ng) of control PapMV or PapMV-p33 VLPs (prepared as described in Example XII). LCMV p33 synthetic peptide-pulsed DCs served as positive controls. Magnetically isolated splenic p33-specific CD8 T lymphocytes from P14 transgenic mice were added ($1 \times 10^5$/well) to pulsed DCs. After 24 h, 0.4 µCi of $^3$H-thymidine was added to each well and cells were cultured for another 24 h. Cells were harvested with a MACH 2 Harvester 96 (TomTec, Hamden, Conn.) and proliferation of p33-specific CD8+ T lymphocytes was evaluated by measuring $^3$H-thymidine incorporation in cellular DNA with a Trillux 1450 MicroBeta counter (Perkin-Elmer, Woodbridge, Ontario). Surface expression of CD69 on proliferating p33-specific CD8+ T lymphocytes was also analyzed. Briefly, cells were stained with PE-coupled p33-H-$2^b$ tetrameric complexes, FITC-coupled anti-mouse CD8a and PerCP-coupled antimouse CD69 mAbs. Samples were acquired and analyzed by flow cytometry as described above. For the in vivo assay, P14 transgenic mice were injected i.v. with 100 µg of control PapMV or PapMV-p33 VLPs. Spleens were collected 24 h post-immunization and the activation state of p33-specific CD8+ T lymphocytes was evaluated as described above.

Results

To assess whether the LCMV p33 CTL epitope displayed on PapMV VLPs could be correctly cleaved, processed and presented by DCs to specific T cells, purified splenic CD11c+ DCs were pulsed for 8 h with various concentrations of VLPs and co-cultured with p33-specific naive CTLs isolated from TCR transgenic P14 mice. Proliferation of p33-specific CTLs was assessed by thymidine incorporation (FIG. 21). PapMV-p33 was very efficiently processed and presented by DCs as it induced high levels of CTL proliferation. As little as 100 ng of VLP (equivalent to 2 ng of free peptide) induced significant T cell proliferation whereas up to 1 µg of control PapMV VLPs did not. The ability of pulsed DCs to activate p33-specific naive T cells was next analyzed by quantifying the upregulation of the T cell activation marker CD69 by flow cytometry (see Example XII, flow cytometry) (FIG. 22A). P33-specific CTLs co-cultured with PapMV-p33 pulsed DCs became fully activated with more than 90% upregulating CD69. To determine whether the efficient capture, processing and presentation of heterologous epitopes presented on PapMV VLPs could also be observed in vivo, p33-specific P14 TCR transgenic mice (see Example XII) were injected i.v. with 100 µg of PapMV VLPs and the activation of splenic p33-specific CTLs was analyzed 24 h after injection by evaluating CD69 surface expression (FIG. 22B). More than 80% of splenic p33-specific T cells from PapMV-p33M-injected P14 mice express CD69, compared to less than 4% for mice injected with control PapMV VLPs. Taken together, these results clearly demonstrate that DCs can efficiently process and crosspresent the p33 CTL epitope displayed on PapMV VLPs.

Example XIV

Vaccination and Immunization with PapMV-gp33 VLPs

Detection of p33-Specific $CD^{8+}$ T Lymphocytes in Immunized Mice

C57BL/6 mice were injected i.v. with 100 µg of VLPs in PBS without adjuvant followed by administration of two identical booster injections at 10-day intervals. Spleens of immunized mice were collected 7 days following the last recall injection. Cells were stained with PE-coupled p33-H-2b tetrameric complexes and FITC-coupled anti-mouse CD8alpha mAb. 7-AAD (BD Bioscience) was used for exclusion of dead cells. Samples (50,000 events in the lymphocyte gate) were acquired and analyzed by flow cytometry as described above. Statistical analysis was done by an unpaired t test using the GraphPad Prism 4.0 software.

$^{51}$Cr Release Assay

Following two or three i.v. injections of 100 µg of PapMV VLPs at 10-day intervals without adjuvant, mice were challenged with 200 PFU of LCMV 7 days after the last booster injection. Five days following LCMV infection of immunized mice, spleen cells were tested for their cytotoxic activity in a standard $^{51}$Cr release assay. Briefly, EL-4 target cells were pulsed with $10^{-6}$ M of p33 synthetic peptide and labelled with 250 mCi $^{51}$Cr for 2 h at 37° C. on a rocking platform. Labelled EL-4 cells were washed three times with MEM 2% FBS and 104 cells were added to splenic effector cells in 96-well round-bottom plates and incubated for 5 h at 37° C. Thirty microliters of each supernatant was mixed for 30 min with 150 µL of OptiPhase SuperMix (Perkin-Elmer). Radioactivity release was measured using a Trillux 1450 MicroBeta counter (Perkin-Elmer). The percentage of specific lysis was calculated as 100×(experimental release-spontaneous release)/(maximum release-spontaneous release). Maximum release was accomplish by adding 2% Triton X-100 (prepared in MEM) to target cells alone and spontaneous release was obtained by incubating target cells without effector cells.

LCMV Focus Assay

Immunized C57BL/6 mice were injected i.v. with 200 PFU of LCMV WE as described above. Five days post-infection spleens were collected and a LCMV focus-forming assay was performed as previously described (Battegay, M., et al., 1991, J. Virol. Methods, 33:191-198). Briefly, 2-fold serial dilutions of spleen homogenates were added onto MC57G cell monolayers in 24-well culture plates. Cells were cultured for 48 h under an overlay of 1% methylcellulose and fixed with 25% formalin in PBS. Fixed cells were stained with rat anti-LCMV VL-4 mAb, HRP-conjugated goat anti-rat mAbs (Jackson ImmunoResearch, West Grove, Pa.) and HRP-conjugated swine anti-goat mAbs (Biosource, Camarillo, Calif.). Ortho-phenylene diamine (Sigma-Aldrich) was used to reveal the infectious foci.

Results

The ability of PapMV-p33 VLPs to induce the development of a specific CTL response in mice was evaluated. Total spleen cells isolated from mice injected with PapMV VLPs were directly analyzed ex vivo by p33-tetramer staining (FIG. 23). Mice administered with PapMV-p33 VLPs developed significant numbers of p33-specific T cells (0.47±0.05%) compared to mice injected with control PapMV VLPs (0.06±0.008%) (p<0.0001, N=6) giving a frequency of about one p33-specific cell per 200 CD8$^+$ T cells. This shows that PapMV VLPs can efficiently prime peptide-specific T cell responses in vivo without the need for using adjuvant.

Acute LCMV infection is exclusively controlled by CTLs (Byrne, J. A. & Oldstone, 1984, J. Virol., 51:682-686; Moskophidis, D., et al., 1987, J. Virol., 61:1867-1874; Zinkernagel, R. M. & Welsh, R. M., 1976, J. Immunol., 117:1495-1502). To determine whether the CTL responses induced by PapMV VLP immunization could protect against viral infections, vaccinated mice were challenged with LCMV as described above. To visualize CTL expansion, the number of p33-specific T cells was determined by tetramer staining 5 days following infection (FIG. 24A), at a time when p33-specific T cells generated by the primary response to LCMV are not yet detectable. Mice having received two injections of PapMV-p33 VLPs showed p33-specific T cell frequencies of ~3.3% of CD8$^+$ T cells whereas mice receiving three injections had even higher numbers of specific T cells (~7.3%) suggesting that the frequency of specific T cells generated by vaccination increased through repeated injections. Importantly, mice vaccinated with either two or three injections of the control PapMV VLPs showed no detectable p33-specific CTLs (FIG. 24A). Whether these CTLs displayed lytic effector function was then evaluated using a standard $^{51}$Cr release assay (FIG. 24B). Cytolytic activity levels in the PapMV-p33 vaccinated group correlated with the numbers of p33-specific T cells detected by tetramer staining. In contrast, mice vaccinated with control PapMV VLPs did not show any specific cytotoxic activity (FIG. 24B). To determine if such cytotoxic responses are protective against LCMV infection, splenic viral titers were determined 5 days following challenge (FIG. 25). Mice having received one or two booster injections of PapMV-p33 VLPs were partially protected from LCMV infection whereas mice receiving three boosts of the same VLP preparation were fully protected as indicated by the absence of detectable virus in the spleen. In contrast, mice receiving three booster injections of control PapMV VLPs showed high LCMV titers in the spleen. Taken together these results demonstrate that vaccination with PapMV-p33 VLPs induces the development of p33-specific effector T cells in a dose-dependant manner and that protection from LCMV infection correlates with the number of effector T cells generated.

Example XV

Production and Engineering of a PapMV-gp100 VLP

Cloning and Engineering of the PapMV-gp100 Construct

A construct comprising the CPΔN5 PapMV CP fused to the HLA-A*0201 epitope from the well defined gp100 melanoma antigen was prepared as follows. The PapMV CP construct (CPΔN5) used for this study is described above (see Example V). To generate the PapMV-gp100 construct, the following oligonucleotides were used.

```
Sense oligonucleotide:
5'-CTAGTTCTTCTGCGTTCACCATCATGGACC      [SEQ ID NO: 32]
AGGTTCCGTTCTCTGTTTCTGTTTCTCAGC
TGA-3',
and Antisense oligonucleotide:
5'-CTAGTCAGCTGAGAAACAGAAACAGAGAAC      [SEQ ID NO: 33]
GGAACCTGGTCCATGATGGTGAACGCAGAA
GAA-3'.
```

The two oligonucleotides were annealed and cloned into the SpeI and MluI sites of the CPΔN5 clone linearized with the same enzymes. The resulting clone PapMV-gp100 comprised the CPΔN5 PapMV CP gene with the gp100 peptide fused at the C-terminus followed by a 6×His tag to facilitate the purification process (see FIG. 18B). The 5 amino acids on each side of each of the HLA-A*0201 epitope were retained in order to favour natural processing by the proteasome as in the native gp100 protein. The sequences of the PapMV clone was confirmed by DNA sequencing.

Expression of PapMV and PapMV gp100 in E. coli

The expression and purification steps were performed as described above in Example X. Three modifications were made to this protocol: the bacteria were lysed by one passage through the French Press; before the elution step, 2 washing steps were added to remove the LPS contaminants from the preparations, one with 10 mM Tris-HCl 50 mM imidazole 0.5% Triton X100 ph8, and another one with 10 mM Tris-HCl 50 mM imidazole 1% Zwittergent ph8. For the PapMV gp100 and PapMV CP proteins, the eluted proteins were subjected to a high speed ultracentrifugation (100 000 g) for 120 min in a Beckman 50.2 TI rotor. VLPs pellets were resuspended in endotoxin-free PBS (Sigma). Finally, protein solutions were filtered using 0.45 µM filters. The protein concentrations were evaluated by BCA protein kit (Pierce). The level of LPS in the purified proteins were evaluated with the Limulus test under manufacturer's instructions (Cambrex) and was below 0.005 Endotoxin Units (EU)/µg of protein. The gp100 peptide was synthesized by GLBiochem Shangai LTD and resuspended in a DMSO (Sigma). This procedure yielded more than 20 mg of purified VLPs per liter of bacterial culture.

Electron Microscopy and SDS-PAGE

The proteins were diluted in PBS and absorbed for 3 min on a carbon-coated formvar grid. The grids were washed 2 times with deionized water and stained with uranyl acetate 0.1% during 10 min at room temperature. The grids were then observed on an on a Jeol JEM220FS transmission electron microscope. The average length of 100 VLPs was evaluated using the Adobe Photoshop software.

SDS-PAGE analyses were performed using the mini-protean system from Bio-Rad (Hercules, Calif.). Proteins were revealed by Coomassie blue staining (Bio-Rad). In some experiments, proteinase K (Invitrogen) was added at a final concentration of 13 µg/ml.

Results

Electron microscopy analysis of the different PapMV VLPs produced in E. coli revealed the typical long rod-shaped structure ranging from 80 to 200 nm in length and a diameter of 15 nm for PapMV VLPs and 16 nm for the engineered PapMV-gp100 VLP indicating that the PapMV-gp100 fusion was able to spontaneously assemble into VLPs in E. coli that are similar in size and shape to the PapMV VLPs.

Stability is an important attribute for a vaccine. SDS-PAGE analysis was performed on fresh and 7-month old VLP preparations in PBS at 4° C. No evidence of degradation was detected on the gel. Furthermore, the preparations were incubated for an additional 7 days at room temperature or at 37°

C., without any noticeable degradation. Finally, the PapMV preparations were incubated with proteinase K as a positive control for degradation, which resulted in the rapid degradation of the engineered PapMV VLP. The PapMV VLP without fusions was more resistant to proteinase K suggesting that the fusion at the C-terminus probably locally destabilizes this region and increases susceptibility to this enzyme.

Example XVI

In vitro Processing and Cross-Presentation of the gp100 Epitope Expressed on PapMVs VLPs Media and Cell Culture T lymphocytes, dendritic cells (DC), and CD40-stimulated B lymphocytes (CD40-B) were cultured as described in the art (Lapointe et al., 2003, Can. Res. 63:653-662) in complete medium, which is Iscove's Modified Dulbecco's Medium (Invitrogen; Carlsbad, Calif.; and Wisent; St-Bruno, Québec, Canada) supplemented with 7.5% human serum (heat-inactivated, prepared from normal donors), 2 mM L-glutamine, 100 U/ml penicillin/streptomycin and 10 µg/ml gentamicin (the last 3 from Invitrogen and Wisent).

CD40-activated B cells were expanded and cultured from peripheral blood mononuclear cells (PBMC) as described previously (Lapointe et al., 2003, Can. Res. 63:653-662) by addition of 500 ng/ml of a soluble trimeric CD40L (Immunex Corporation; Seattle, Wash.) and 500 U/ml recombinant human IL-4 (Peprotech; Rocky Hill, N.J.).

DCs were generated from PBMC collected by apheresis preparations from normal donors (Lapointe et al., 2000, Eur. J. Immunol. 30:3291-3298), by modifying the original protocol described by Sallusto et al., 1994, J. Exp. Med. 179: 1109-1118. Briefly, PBMC were enriched from blood by centrifugation on a lymphocyte separation medium (Wisent). Monocytes were enriched following 2 hours adherence in tissue culture flasks or plates at 37° C. ($3 \times 10^7$ cells in T-25, $1.5 \times 10^7$ cells/well in 6 well flat bottom plates or $5 \times 10^6$ cells/well in 24 well flat bottom plates, all from Costar, Corning, N.Y.). Adherent cells were washed once with PBS (Wisent) and then cultured in complete medium supplemented with 100 ng/ml of GM-CSF (1,000 U/ml) and 500 ng/ml of IL-4 (1,000 U/ml) (both from Peprotech, Rocky Hill, N.J.). GM-CSF and IL-4 were added again on days 3 and 5. PapMV VLP and PapMV-gp100 (prepared as described in Example XV) were added on day 6 and harvested at day 7 for recognition and expansion experiments.

The melanoma cell line 1088mel was established at the Surgery Branch (NCI/NIH). SK23, T2, and breast tumor cell lines MDA231 were obtained from the American Type Culture Collection (ATCC; Manassas, Va.). All tumor cell lines were cultured in RPMI 1640 medium supplemented with 10% heat-inactivated FBS, 2 mM L-glutamine, 100 U/ml penicillin/streptomycin and 10 µg/ml gentamicin.

Cross-Presentation from PapMV Pulsed APC

Different target cells were analyzed for MHC class I presentation of defined epitopes with gp100-specific T cells. Gp100-specific CD8$^+$ T cell clones were kindly provided by the National Cancer Institute; NIH, Bethesda, Md. and were specific to both the native HLA-A*0201-restricted epitope in position 209-217 (ITD QVP FSV [SEQ ID NO:34]) and to the modified version with a M in position 210 (IMD QVP FSV [SEQ ID NO:5]), which enhances the stability of the peptide/MHC complex. Gp100-specific T cells were expanded using the rapid expansion protocol described by Dudley et al., 1999, J. Immunother, 22:288-298.

To evaluate cross-presentation mediated by PapMV VLPs, CD40-activated B cells or DC were pulsed with PapMV VLPs at 10-50 µg/ml for 20 hours. Cells were harvested, washed twice with PBS, and seeded in complete media (at $4-10 \times 10^4$ cells/well) in 96 well-plates. Gp100-specific T cells were added at $2-10 \times 10^4$ cells/well in complete media for 20 hours. Culture supernatants were harvested and interferon (IFN)-γ was evaluated by ELISA. In some experiments, APC were pre-treated for 1 hour with 50-70 µM chloroquine (Sigma, St-Louis, Mo.), 20-25 µg/mL lactacystin or 1.3-3.3 µM MG-132 (the latter two from Calbiochem, San Diego, Calif.). Cells were washed with PBS and re-suspended in media containing 1/20 of the original inhibitor concentration. Treated cells were pulsed with the PapMV VLPs and analysis of MHC class I mediated presentation was performed as described above.

Results

DC and CD40-activated B lymphocytes were pulsed with the different versions of PapMV VLPs, and co-cultured with defined T cells specific to MHC class I epitopes from the gp100 antigen. As shown in FIG. 26, only APC pulsed with PapMV gp100 were recognized by the gp100-specific T cell clone. The specificity of the T cell cultures was confirmed by pulsing CD40-activated B cells with the synthetic peptides corresponding to each epitopes.

To confirm that HLA-A*02 was the restriction element involved in peptide presentation, similar experiments were performed with APC prepared from 2 additional HLA-A*02 donors, and 2 others negative for this allele. The gp100-specific T cell clone was reactive only with PapMV gp100-pulsed HLA-A*02$^+$ APC (FIG. 27A), further confirming that APC expressing the relevant restriction element are necessary for antigenic presentation. Finally, presentation by MHC class I was controlled using antibodies blocking either MHC class I, or class II or HLA-DR presentation, as previously described (Lapointe et al., 2003, Can. Res. 63:2836-2843; Lapointe et al., 2001, J. Immunol. 167:4758-4764). As a control, a melanoma line expressing both HLA-A*0201 and gp100 was co-cultured with the gp100-specific T cell clone, and only antibody blocking MHC class I presentation abrogated the recognition, as expected (FIG. 27B). Co-culture of gp100-specific T cell clones with lines either HLA-A*02$^-$/gp100$^+$, or +/−, or −/− failed to provoke IFN-γ secretion as previously demonstrated (Dudley et al., 1999, J. Immunother. 22:288-298; Lapointe et al., 2001, J. Immunol. 167:4758-4764).

Antigens have to be processed by proteases to generate epitopes recognized by T cells, and for MHC class I epitopes, classical processing is mediated by the proteasome. Furthermore, and as known in the art, cross-presentation of exogenous antigen by MHC class I can also be mediated by cathepsins and other residents of the endosomal pathway (Rock and Shen, 2005, Immunol. Rev. 207:166-183). Interestingly, VLP from PapMV can get internalized in vesicles when pulsed on APC (data not shown), if the processing of the PapMV VLPs was mediated by the proteasome. Two different proteasome inhibitors were exploited, namely, lactacystin and MG-132, and their activities controlled by blocking classical MHC class I presentation of the HLA-A*0201 epitope from gp100 by melanoma cells (FIG. 28).

Overall, these data suggests that the MHC class I cross-presentation mediated by the PapMV VLPs is proteasome-independent.

Example XVII

Immunogenicity of PapMV VLPs Fused to a Hepatitis C Virus Epitope

Cloning and Engineering of the PapMV Coat Protein

The PapMV CP gene was amplified by RT/PCR from isolated viral RNA using the following primers:

```
5'-AGTCCCATGGCATCCACACCCAACATA       [SEQ ID NO: 35]
GCCTTC-3',
and

5'-GATCGGATCCTTACTAATGGTGATGGTGAT    [SEQ ID NO: 36]
GGTGACGCGTGGTACTAGTTTCGGGGGGTGGAA
GGAATTGGATGGTTGG-3'.
```

The PCR product was cloned as an NcoI/BamHI fragment into pET 3D (New England Biolabs).

To generate the PapMVCP-E2 construct, the following oligonucleotides were used:

```
5'-GATCACTAGTGTGGTGGTGGGTACCACCGA    [SEQ ID NO: 37]
TCGTAGCGGTGCGCCGACCTACAGCTGGGGTGC
GAACGATACGCGTCATG-3',
and 5'-CATGACGCGTATCGTTCGCACCCCAGCTGT    [SEQ ID NO: 38]
AGGTCGGCGCACCGCTACGATCGGTGGTACCCA
CCACCACACTAGTGATC-3'.
```

These two oligonucleotides were annealed together and digested with SpeI and MluI before ligation into the SpeI/MluI-linearized PapMVCP clone.

The expression vector for the truncated coat protein E2 fusion, PapMVCP$_{27-215}$-E2, was constructed from the PapMVCP-E2 plasmid by first preparing the following two oligonucleotides (including an NcoI restriction site) designed to delete the 26 first amino acids of the PapMV CP were used for PCR:

```
forward primer:
5'-AGTCCCATGGCCGATCCAACGTCCAATCT     [SEQ ID NO: 39]
TCTG-3',
and reverse primer:
5'-ACGTCCATGGTATATCTCCTTCTTA         [SEQ ID NO: 40]
AAG-3'.
```

The PCR product was then self-ligated. The expression vector for PapMVCP$_{27-215}$ was derived from the PapMVCP plasmid following the same procedure as for the construction of the PapMVCP$_{27-215}$-E2 clone. The sequences of all PapMV clones were confirmed by DNA sequencing.

PapMVCP-E2 and PapMVCP$_{27-215}$-E2 Expression and Purification

Expression and purification of PapMVCP constructs were performed as follows. Briefly, the bacteria were lysed through a French Press and then loaded onto a Ni$_{2+}$ column, washed with 10 mM Tris-HCl 50 mM Imidazole 0.5% Triton X100 pH8, then with 10 mM Tris-HCl, 50 mM Imidazol, 1% Zwittergent pH8 to remove endotoxin contamination. For the PapMVCP-E2 protein, the elution solution was subjected to high speed centrifugation (100 000 g) for 120 min in a Beckman 50.2 TI rotor. The VLP pellet was resuspended in endotoxin-free PBS (Sigma). For the PapMVCP$_{27-215}$-E2 protein, after dialysis in PBS using a 6-8 kDa molecular weight cut-off membrane (Spectra), 2 ml (at a concentration of 2.75 mg/ml) of PapMVCP$_{27-215}$-E2 was loaded onto a Superdex 200 column (GE Healthcare) previously equilibrated with 1×PBS. The molecular weight of PapMVCP$_{27-215}$-E2 was calculated from a standard curve constructed from the elution profile of reference markers (ribonuclease A, chymotrypsigen A, albumin, ovalbumin).

The same protocol was followed for the production and purification of PapMVCP and PapMVCP$_{27-215}$. The E2 peptide was synthesized by GLBiochem Shangai LTD and resuspended in a endotoxin free PBS (Sigma). Protein solutions were filtrated using 0.45 µM filters before use. The amount of protein was evaluated using a BCA protein kit (Pierce). The level of LPS in the purified protein was evaluated with the Limulus test according to the manufacturer's instructions (Cambrex) and was below 0.005 endotoxin units (EU)/µg of protein.

SDS-PAGE, Electroblotting and Electron Microscopy

SDS-PAGE and electroblotting were performed as described in the previous examples. Proteins were diluted in PBS and were absorbed for 3 min on a carbon-coated formvar grid. The grids were washed twice with deionised water and stained with 0.1% uranyl acetate for 10 min at room temperature. The grids were then observed on a Jeol JEM220FS transmission electron microscope. Average VLP length was evaluated by measuring 100 VLPs using Adobe Photoshop software.

Immunization

Five 4- to 8-week-old C3H/HeJ mice (Charles Rivers Laboratories) were injected subcutaneously with 25 µg of PapMVCP-E2, PapMVCP$_{27-215}$-E2 or the equivalent amount of the E2 peptide (2 µg) or endotoxin-free PBS (Sigma). Primary immunization was followed by one booster dose given 2 weeks later. Blood samples were obtained at different time points and stored at −20° C. until analysis. All the experimental protocols were approved by the Laval University animal protection committee.

ELISA Quantification

Costar High Binding 96-well plates (Corning, N.Y., USA) were coated overnight at 4° C. with 100-200 µl/well of P3, P3E2, PapMVCP, PapMVCP$_{27-215}$, or PapMVCP-E2 diluted to a concentration of 1 µg/ml in 0.1 M NaHCO$_3$ buffer pH 9.6. The plates were blocked with PBS/0.1% Tween-20/2% BSA (150 µl/well) for 1 hour at 37° C. After washing three times with PBS/0.1% Tween-20, sera were added in 2-fold serial dilution beginning from 1:50 and incubated for 1 hour at 37° C. Following incubation, the plates were washed three times and incubated with 100 µl of peroxidase-conjugated goat anti-mouse IgG, IgG1, IgG2a, IgG2b (all from Jackson Immunoresarch), IgG3 (Rockland) at a dilution of 1/10,000 in PBS/0.1% Tween-20/2% BSA for 1 hour at 37° C. After three washes, the presence of IgG was detected with 100 µl of TMB-S according to the manufacturer's instructions; the reaction was stopped by adding 100 µl of 0.18 mM H$_2$SO$_4$ and the OD was read at 450 nm. The results are expressed as antibody endpoint titer, determined when the OD value is 3-fold the background value obtained with a 1:50 dilution of serum from PBS mice.

For the determination of antibody levels in human sera, the same conditions were applied, except that the peroxidase-conjugated goat anti-human IgG as secondary antibodies were used at a dilution of 1/80000. Sera from infected HCV patients were provided by B. Willems (Hopital Saint Luc, CHUM): the results are expressed as antibody endpoint titer, defined as when the OD value is 3-fold the background value obtained with a 1:25 dilution of serum from a pool of sera from 15 non-infected patients.

Splenocyte Restimulation

CD-1 mice (22 weeks old) were immunized with PapMVCP-E2 (25 µg) on days 0, 15, 30, 45 before being sacrificed on day 65. Spleens were removed and suspended in DMEM ($2\times10^5$ cells/well). Red blood cells were removed with hypertonic ammonium chloride solution. Splenocytes were washed and resuspended in 200 µl of DMEM medium (DMEM supplemented with 10% FBS [HyClone], 100 U/ml penicillin, 100 µg/ml streptomycin, 2 mM L-glutamine, 1 mM sodium pyruvate, and 50 µM β-mercaptoethanol) to a concentration of $2.5\times10_5$ cells/ml in 96-well flat-bottom microplates (Costar). Samples were incubated four days with 25 µg/ml of PapMVCP or PapMVCP-E2 VLPs. Concavalin A (ConA—10 µg/ml) and PBS were used as positive and negative controls. Cells culture supernatants were collected and cytokines were measured using the liquid mouse 10 cytokines kit (Qiagen).

Air Pouch in Mice

Air pouches were raised in 10- to 12-week-old CD-1 mice (Charles River Laboratories). Air pouches were raised on the dorsum by subcutaneous injection of 3 ml of sterile air on days 0 and 3. On day 7, one ml of recombinant PapMVCP (1 to 10 µg/ml), LPS (10 µg/ml) or PBS were injected in the air pouches. Six hours after the treatment, the mice were killed by asphyxiation using $CO_2$. The air pouches were washed once with 1 ml PBS-5 mM EDTA, and then twice with 2 ml of PBS-5 mM EDTA, and the exudates were centrifuged at 500×g for 5 min at room temperature. Cells were counted with a hematocytometer following acetic blue staining.

Bone Marrow Cell Extraction and Differentiation in APCs

Bone-marrow progenitors cells were obtained from the femurs of BALB/c mice and cultured for 6 days in dendritic cells differentiation bone marrow medium (95% RPMI with 1% penicillin-streptomycin and supplemented with 5%x63-GM-CSF supernatant media culture; the x63-GM247 CSF cell line was provided by B. Ludewig, Research Department, Kantonal Hospital St. Gallen, Switzerland). Medium was partially replaced on day 2 and 4. On day 6, the medium was replaced by medium without L×63 conditioned medium. On day 7, enrichment of APCs was verified by flow cytometry using FITC anti-CD11c and PE-Cy5.5 anti-CD11b surface markers (BD Biosciences). The preparation contained 25% of CD11c+Cd11+ cells, and more than 80% of CD11b+ cells. We refer to this preparation as APCs.

Flow Cytometry

To evaluate the internalization of the PapMVCP-E2 or PaPMVCP$_{27-215}$-E2 in APCs, 1 million of bone marrow derived APCs were incubated for 2 hours at 37° C. with either 25 µg of PapMVE2 or PaPMVCP$_{27-215}$-E2. Briefly, cells were blocked with PBS 10% FBS and anti-CD16/CD32 (1 µg/1 million cells) 15 min at 4° C. After 2 washes with PBS, cells were fixed with PBS/2% paraformaldehyde for 10 min at room temperature. After 2 washes with permeabilization buffer (PBS 10% FBS 0.2% Triton X-100), cells were incubated for 45 min at 4° C. with the rabbit polyclonal antibodies diluted 1/200 in permeabilization buffer. After 2 washes with permeabilization buffer, cells were incubated for 45 min at 4° C. with the secondary antibodies anti-rabbit IgG alexa 488 (Molecular Probes) diluted 1/5000 in permeabilization buffer. After washing with PBS, cells were immediately analysed with a EPICS-XL cytofluorimeter. Data analysis was performed using WINMDI2.8. The rabbit polyclonal Ab used for detection was produced in our own facilities: rabbit preimmune serum was used as a negative control.

Confocal Microscopy

APCs were grown (200,000 cells/well) in a 12-well plates (Corning, N.Y., USA) containing sterile slides in the bottom following the same differentiation protocol as described previously. For antigen internalization studies, 5 µg of antigen/200000 cells was used. The fixation, permeabilization, primary and secondary antibodies incubation steps were as described for flow cytometry. Slides were analysed immediately with a Fluoview Fv300 confocal microscope with a ×60 oil immersion objective. Fluorescence images were acquired sequentially to avoid non-specific channel interference and by x-z sectioning. Pictures were then digitally processed with Image J software.

Statistical Analysis

Nonparametric Krustal-Wallis and Dunn's multiple comparison tests were used for statistical analysis. A value of $P<0.05$ was considered statistically significant. Statistical analyses were performed with the program PRISM 3.03.

Results

The purified recombinant proteins showed the expected molecular weights of 23 kDa (PapMVCP$_{27-215}$-E2) and 26 kDa for PapMVCP and PapMVCP-E2 (FIG. 1B), and endotoxin levels were always below 0.005 EU/µg of protein. Electron microscopy (EM) observations confirmed that the addition of the E2 peptide at the C-terminus of the PapMVCP did not affect the ability of the protein to self-assemble into VLPs that are similar to the recombinant PapMVCP VLPs. As expected, PapMVCP$_{27-215}$-E2 was unable to form VLPs and remained as a monomeric form as previously shown (Leclerc et al., 1998, J Biol Chem, 273:29015-21). The lengths of the VLPs are variable, with a size range of 201±80 nm. A 201 nm length protein represents 560 copies of the CP presenting the E2 peptide in a repetitive and crystalline fashion.

To test the pro-inflammatory properties of PapMVCP VLPs, the mouse air pouch model was used. Injection of 10 µg of PapMVCP VLPs with very low LP content (<0.005 EU/µg) failed to induce the recruitment of leucocytes into the pouch of CD1 mice six hours after the treatment. In contrast, injection of LPS at doses of 1,000 and 1 EU was very effective in inducing the recruitment of leucocytes (FIG. 29). This result suggests that PapMVCP VLPs are not pro-inflammatory after 6 hours and that the very low level of LPS in PapMVCP protein samples would not exert any notable immunogenic effects in subsequent experiments.

The capacity of the monomeric (PapMVCP$_{27-215}$-E2) and the multimeric (PapMVCP-E2) forms to be internalized in bone marrow derived APCs enriched in bone-marrow-derived dendritic cells (BMDDC) was tested. Flow cytometry analysis showed that APCs become efficiently immunolabelled by both the multimeric and the monomeric forms (95.3% for the PapMVCP-E2 VLP and 92.6% for the PapMVCP$_{27-215}$-E2 VLP). To visualize the interaction between the recombinant proteins and the APCs, the treated APCs were observed by confocal microscopy. In both cases, the immunolabelled PapMVCP signal was clearly vesicular, intracytoplasmic and perinuclear. Both recombinant proteins were efficiently internalized in the APCs.

To examine the capacity of PapMVCP VLPs to induce an immune response, C3H/HeJ mice were injected subcutaneously with 25 µg of the recombinant VLPs (PapMVCP-E2) or 25 µg of the monomeric form (PapMVCP$_{27-215}$-E2). The amount of E2 peptide present in each dose is estimated at 2 µg. A booster dose was given on day 15 after primary immunization. Mice sera were assayed for anti-PapMVCP, PapMVCP$_{27-215}$ and anti-E2 peptide antibodies. Anti-CP IgG was clearly detected in mice immunized with PapMVCP-E2 on day 12, while only a weak level of anti-CP was detected in the sera of mice vaccinated with PapMVCP$_{27-215}$-E2, even after the booster on day 15 (FIG. 30A). To detect anti-peptide antibodies, ELISA plates were coated with either a carrier (cauliflower mosaic virus pIII protein) protein alone or fused to the HCV E2 epitope (PIII-E2). The carrier protein fusion was used to detect anti-peptide IgG to stabilize the peptide and ease the purification process from *E. coli*. Only sera of mice immunized with PapMV-E2 showed IgG antibodies against the carrier protein fused to the E2 peptide (PIII-E2), increasing after the booster on day 15 (FIG. 30B). No antibody response was detectable against the carrier alone (PIII) for all sera (FIG. 30C). To examine the specificity of the antibody response elicited by the VLPs, sera from mice immunized with VLPs without the peptide or with another peptide (derived from HCV E1 glycoprotein) were tested against PIII and PIII-E2. Antibodies to these latter proteins were not detected, confirming the specificity of the E2 antibodies. The multimeric form was able to trigger a long-lasting response against both the CP and the E2 epitope: moreover, from day 23 to day 120, the antibody titre against the capsid decreased only on a 1 $\log_2$ scale (FIG. 30A), while the antibody titre against the peptide decreased on a 4 $\log_2$ scale (FIG. 30B). Isotyping of the anti-peptide antibodies revealed a Th1/Th2 balanced profile, with a prevalence of IgG1, IgG2a, IgG2b antibodies and a less pronounced production of IgG3 (FIG. 30D). A similar immunization protocol was performed in Balb/C mice with identical results: the same Th1/Th2 profile was observed with a similar IgG isotyping profile directed against both the PapMVCP and the E2 epitope.

To analyse the TH1/TH2 profile obtained with the IgG isotypes, a T-cell proliferation assay was performed. High levels of IL-2, suggesting lymphoproliferation, were secreted by splenocytes, in amounts similar to the positive control, when reactivated with PapMVCP and PapMVCP-E2 (FIG. 31A). IL-4 was also secreted when splenocytes were reactivated with PapMVCP and PapMVCP-E2 (IL-4 profile, FIG. 31B). No detectable level of these 2 cytokines was induced by reactivation with PIII-E2 or PIII. The detection of those typical TH1 and TH2 cytokines (Karulin et al., 2000, J Immunol, 164:1862-72) is consistent with the profile of the antibody isotypes.

In addition, the ability of the peptide derived from the HCV surface glycoprotein E2 that is fused to the C-terminal of the PapMV CP to correctly mimic the native conformation of the peptide at the surface of the virus was evaluated by testing serum from HCV-infected patients for reaction against PapMVCP-E2 VLPs. Of eight sera from HCV patients tested, one (patient no. 6) reacted with E2 peptide at the surface of PapMVCP-E2 VLPs, while the same serum did not react against PapMVCP VLPs. When the E2 peptide was fused in the context of the carrier protein (PIII), the same serum was reactive to the peptide. A second serum (patient no. 5) also reacted weakly to the E2 peptide. This result suggests that the chosen E2 peptide is presented on the VLP in a similar manner to the WT E2 epitope at the surface of HCV.

Example XVIII

Adjuvant Effect of PaPMV

PapMV Purification

PapMV was purified as described in Example X.

Antigens

LPS-free OVA Grade VI was purchased from Sigma-Aldrich Chemical Co, St Louis, Mo. Hen egg white lysozyme (HEL) was purchased from Research Organics Inc. Cleveland, Ohio. LPS from *E. coli* O111:B4 was purchased from Sigma-Aldrich, St Louis, Mo.

Immunizations

BALB/c mice, 6-8 weeks old, were bred and kept under the animal facilities of the Experimental Medicine Department, Faculty of Medicine, National Autonomous University of Mexico (UNAM), and were cared for in conformity with good laboratory practice guidelines. To study the effects of adjuvant, groups of mice were immunized i.p. on day 0 with 2 mg of OVA or HEL alone or with 30 mg of PapMV, CFA 1:1 (v/v), or 5 mg of LPS from *E. coli* O111:B4 (Sigma-Aldrich). Control mice were injected with saline solution only. Blood samples were collected from the retro-orbital sinus at various times, as indicated in FIG. 6. Individual serum samples were stored at −20° C. until analysis. Three mice were used in each experiment.

Determination of Antibody Titers by ELISA

High-binding 96-well polystyrene plates (Corning®, New York, N.Y.) were coated with 1 mg/mL of PapMV, 100 mg/mL of HEL, or 150 mg/mL OVA in 0.1 M carbonate-bicarbonate buffer (pH 9.5). Plates were incubated for 1 h at 37° C. and then overnight at 4° C. Before use the next morning, plates were washed three times in PBS (pH 7.2) containing 0.05% Tween-20 (PBS-T) (Sigma-Aldrich). Nonspecific binding was blocked with 5% nonfat dry milk diluted in PBS (PBS-M) for 1 h at 37° C. After washing, mice serum was diluted 1:40 in PBS-M, and 2-fold serial dilutions were added to the wells. Plates were incubated for 1 h at 37° C. and then washed four times with PBS-T. Peroxidase-conjugated rabbit anti-mouse IgM (optimal dilution 1:1000) IgG, IgG1, IgG2a, IgG2b antibodies (Zymed, San Francisco, Calif.) or IgG3 (optimal dilution 1:3000) (Rockland, Gilbertsville, Pa.) was added, and the plates were incubated for 1 h at 37° C. and washed three times with PBS-T. Orthophenylenediamine (0.5 mg/mL; Sigma-Aldrich) in 0.1 M citrate buffer (pH 5.6) containing 30% hydrogen peroxide was used as the enzyme substrate. The reaction was stopped with 2.5 N H2SO4, and the absorbance was determined at 490 nm using an automatic ELISA plate reader (Dynex Technologies MRII, Chantilly, Va., USA) with BIOLINX 2.22 software. Antibody titers are given as −log 2 dilution 40. A positive titer was defined as 3 SD above the mean value of the negative control.

Results

The translation of innate immune response into antibody response is observed when adjuvants are co-administered to poor immunogenic vaccines. Adjuvants are substances capable of strengthen or augment the antibody or cellular immune response against an antigen. To determine whether PapMV is an adjuvant that can promote a long-lasting antibody response to other antigens, BALB/c mice were immunized with OVA or HEL either alone or together with the following adjuvants: PapMV, CFA, or LPS. The IgG antibody titer specific for OVA or HEL was measured by ELISA at the time points indicated (FIGS. 6A and B). PapMV adjuvant effect was observed on the total IgG response to OVA and HEL in immunized animals. An adjuvant effect induced by PapMV was observed for HEL on day 30 after immunization, when the antibody titer increased 8-fold compared with the antibody titer induced by HEL alone. This difference in antibody titer was maintained until day 120 but not on day 400 (FIG. 4A). Although LPS induced an adjuvant effect only in the first 30 days after immunization, CFA showed the strongest adjuvant effect from day 8 to the end of the experiment on day 400 after immunization (FIG. 4A). For immunization with OVA, the adjuvant effect on total IgG antibody titers was observed only until day 120 after the first immunization, after which antibody titer decreased with time and was 4-fold higher compared with OVA on day 400 (FIG. 4B). Further analysis was performed on day 20 to identify which IgG subclasses were induced by OVA and OVA coimmunized with adjuvants (where PapMV did not show an adjuvant effect on the total IgG response). PapMV, LPS, and CFA induced OVA-specific IgG2a and IgG2b antibody titers, whereas OVA alone induced only IgG1-specific antibody titers (FIG. 4C-E). No adjuvant effect for IgG1 was observed when OVA was coimmunized with any of the adjuvants used. These results show that PapMV, LPS, and CFA induce an adjuvant effect on the IgG subclass responses to OVA. Moreover, PapMV exhibits adjuvant properties that induce a long-lasting increase in specific antibody titers to model antigens. Taken together, these data suggest that PapMV has intrinsic adjuvant properties that may have mediated the translation of the innate response into the antigen-specific long-lasting antibody response observed.

The disclosure of all patents, publications, including published patent applications, and database entries referenced in this specification are expressly (specifically) incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention as outlined in the claims appended hereto.

We claim:

1. An immunopotentiating composition comprising one or more immunogens and an adjuvant, the adjuvant comprising a PapMV virus-like particle (VLP) comprising a plurality of PapMV coat proteins, wherein the coat proteins are capable of self-assembly to form a VLP, wherein the one or more immunogens are fused to a C-terminus of said coat protein comprised by said VLP.

2. A method of preparing the immunopotentiating composition of claim 1, said method comprising:
   (a) providing a polynucleotide encoding a PapMV coat protein fused at the C-terminus to one or more immunogens;
   (b) expressing said polynucleotide in *Escherichia coli* to provide said PapMV coat protein fused at the C-terminus to one or more immunogens;
   (c) allowing said PapMV coat protein fused at the C-terminus to one or more immunogens to multimerise and assemble to form VLPs, and
   (d) combining said VLPs with a physiologically acceptable carrier.

3. A recombinant fusion protein comprising PapMV coat protein and one or more immunogens fused to the C-terminus of said coat protein, wherein said recombinant fusion protein is capable of self-assembly to form virus-like particles (VLPs).

4. A pharmaceutical kit comprising the immunopotentiating composition of claim 1.

5. The immunopotentiating composition of claim 1, wherein said PapMV coat protein is a wild-type PapMV coat protein.

6. The immunopotentiating composition of claim 1, wherein said coat protein has an amino acid sequence having at least 95% sequence identity over its full length to the sequence as set forth in SEQ ID NO:1.

7. The immunopotentiating composition of claim 1, wherein said coat protein comprises an amino acid sequence having at least 97% sequence identity over its full length to the sequence as set forth in SEQ ID NO:1.

8. The immunopotentiating composition of claim 1, wherein said coat protein comprises a deletion of between one and about ten amino acids from the N-terminus.

9. The immunopotentiating composition of claim 1, wherein said coat protein comprises a deletion of between one and about five amino acids from the N-terminus.

10. The immunopotentiating composition of claim 1, wherein said coat protein comprises an amino acid sequence as set forth in SEQ ID NO:3.

11. The immunopotentiating composition of claim 1, wherein said coat protein comprises a deletion of between one and about ten amino acids from the C-terminus.

12. The immunopotentiating composition of claim 1, wherein said coat protein comprises a substitution of glutamate for a neutral amino acid at position 128.

13. The immunopotentiating composition of claim 1, wherein said coat protein comprises a substitution of glutamate for alanine at position 128.

14. The immunopotentiating composition of claim 12, wherein said coat protein further comprises a deletion of between one and about ten amino acids from the N-terminus.

15. The immunopotentiating composition of claim 12, wherein said coat protein further comprises a deletion of between one and about five amino acids from the N-terminus.

16. The immunopotentiating composition of claim 12, wherein said coat protein further comprises a deletion of between one and about ten amino acids from the C-terminus.

17. The immunopotentiating composition of claim 1, wherein said one or more immunogens comprise a viral immunogen, a bacterial immunogen or a cancer immunogen.

18. The immunopotentiating composition of claim 1, wherein said one or more immunogens are cytopathic virus immunogens, intracellular pathogen immunogens or cancer immunogens.

19. The immunopotentiating composition of claim 1, wherein said one or more immunogens comprise a hepatitis C immunogen, a hepatitis B immunogen, a *Salmonella typhi* immunogen, a human immunodeficiency virus immunogen or a cancer immunogen.

20. The immunopotentiating composition of claim 1, wherein said immunopotentiating composition is capable of inducing a humoral and/or cellular immune response in an animal.

21. The recombinant fusion protein of claim 3, wherein said coat protein comprises an amino acid sequence having at least 95% sequence identity over its full length to the sequence as set forth in SEQ ID NO:1.

22. The recombinant fusion protein of claim 3, wherein said coat protein comprises an amino acid sequence having at least 97% sequence identity over its full length to the sequence as set forth in SEQ ID NO:1.

23. The recombinant fusion protein of claim 3, wherein said coat protein comprises a deletion of between one and about ten amino acids from the N-terminus.

24. The recombinant fusion protein of claim 3, wherein said coat protein comprises a deletion of between one and about five amino acids from the N-terminus.

25. The recombinant fusion protein of claim 3, wherein said coat protein comprises an amino acid sequence as set forth in SEQ ID NO:3.

26. The recombinant fusion protein of claim 3, wherein said coat protein comprises a deletion of between one and about ten amino acids from the C-terminus.

27. The recombinant fusion protein of claim 3, wherein said one or more immunogens comprise a viral immunogen, a bacterial immunogen or a cancer immunogen.

28. The recombinant fusion protein of claim 3, wherein said one or more immunogens comprise a cytopathic virus immunogen, a intracellular pathogen immunogen or a cancer immunogen.

29. The recombinant fusion protein of claim 3, wherein said one or more immunogens comprise a hepatitis C immunogen, a hepatitis B immunogen, a *Salmonella typhi* immunogen, a human immunodeficiency virus immunogen or a cancer immunogen.

30. A recombinant PapMV coat protein comprising an amino acid sequence as set forth in SEQ ID NO:1 in which glutamate at position 128 has been substituted for a neutral amino acid.

31. The recombinant PapMV coat protein of claim 30, wherein glutamate at position 128 has been substituted for alanine.

32. The recombinant PapMV coat protein of claim 30 further comprising a deletion of between one and ten amino acids from the N-terminus.

33. The recombinant PapMV coat protein of claim 30 further comprising a deletion of between one and five amino acids from the N-terminus.

34. The recombinant PapMV coat protein of claim 30 further comprising a deletion of between one and ten amino acids from the C-terminus.

35. The recombinant PapMV coat protein of claim 30 further comprising a fusion of one or more immunogens at the C-terminus.

36. The immunopotentiating composition of claim 20, wherein said animal is a human.

37. The immunopotentiating composition of claim 20, wherein the animal is a non-human animal.

38. The immunopotentiating composition of claim 1, wherein the one or more immunogens comprise one or more epitopes together with sequences which flank said one or more epitopes.

39. The recombinant fusion protein of claim 3, wherein the one or more immunogens comprise one or more epitopes together with sequences which flank said one or more epitopes.

40. The recombinant PapMV coat protein of claim 35, wherein the one or more immunogens comprise one or more epitopes together with sequences which flank said one or more epitopes.

41. The immunopotentiating composition of claim 1, wherein the coat protein comprises a deletion of five amino acids from the N-terminus of the wild-type PapMV coat protein sequence and further comprises an insertion of alanine at position 2 of the coat protein.

42. The recombinant fusion protein of claim 3, wherein the coat protein comprises a deletion of five amino acids from the N-terminus of the wild-type PapMV coat protein sequence and further comprises an insertion of alanine at position 2 of the coat protein.

43. The immunopotentiating composition of claim 20, wherein said humoral immune response is a memory immune response.

44. A PapMV virus-like particle comprising a plurality of the recombinant fusion proteins of claim 3.

* * * * *

SEQUENCE LISTING

```
<160> NUMBER OF SEQ ID NOS: 40

<210> SEQ ID NO 1
<211> LENGTH: 215
<212> TYPE: PRT
<213> ORGANISM: Papaya mosaic virus

<400> SEQUENCE: 1

Met Ser Lys Ser Ser Met Ser Thr Pro Asn Ile Ala Phe Pro Ala Ile
  1               5                  10                  15

Thr Gln Glu Gln Met Ser Ser Ile Lys Val Asp Pro Thr Ser Asn Leu
             20                  25                  30

Leu Pro Ser Gln Glu Gln Leu Lys Ser Val Ser Thr Leu Met Val Ala
         35                  40                  45

Ala Lys Val Pro Ala Ala Ser Val Thr Thr Val Ala Leu Glu Leu Val
     50                  55                  60

Asn Phe Cys Tyr Asp Asn Gly Ser Ser Ala Tyr Thr Thr Val Thr Gly
 65                  70                  75                  80

Pro Ser Ser Ile Pro Glu Ile Ser Leu Ala Gln Leu Ala Ser Ile Val
                 85                  90                  95

Lys Ala Ser Gly Thr Ser Leu Arg Lys Phe Cys Arg Tyr Phe Ala Pro
            100                 105                 110

Ile Ile Trp Asn Leu Arg Thr Asp Lys Met Ala Pro Ala Asn Trp Glu
        115                 120                 125

Ala Ser Gly Tyr Lys Pro Ser Ala Lys Phe Ala Ala Phe Asp Phe Phe
    130                 135                 140

Asp Gly Val Glu Asn Pro Ala Ala Met Gln Pro Pro Ser Gly Leu Ile
145                 150                 155                 160

Arg Ser Pro Thr Gln Glu Glu Arg Ile Ala Asn Ala Thr Asn Lys Gln
                165                 170                 175

Val His Leu Phe Gln Ala Ala Ala Gln Asp Asn Asn Phe Thr Ser Asn
            180                 185                 190

Ser Ala Phe Ile Thr Lys Gly Gln Ile Ser Gly Ser Thr Pro Thr Ile
        195                 200                 205

Gln Phe Leu Pro Pro Pro Glu
    210                 215

<210> SEQ ID NO 2
<211> LENGTH: 648
<212> TYPE: DNA
<213> ORGANISM: Papaya mosaic virus

<400> SEQUENCE: 2
```

```
atgtctaagt caagtatgtc cacacccaac atagccttcc ccgccatcac ccaggaacag    60
atgagctcga ttaaggtcga tccaacgtcc aatcttctgc cctcccaaga gcagttaaag   120
tcagtgtcca ccctcatggt agctgctaag gttccagcag ccagtgttac aactgtggca   180
ttggagttgg tcaacttctg ctatgacaat gggtccagcg cgtacaccac agtgactggc   240
ccatcatcaa taccggagat atcactggca caattggcta gtattgtcaa agcttccggc   300
acttccctta gaaaattctg ccggtacttc gcgccaataa tctggaatct gaggacggac   360
aaaatggctc ctgccaattg ggaggcttca ggatacaagc caagcgccaa atttgccgcg   420
ttcgacttct tcgacggggt ggagaatccg gcggccatgc aaccccttc gggactaatc     480 aggtcgccga cccaggaaga gcggattgcc aatgctacca acaaacaggt gcatctcttc   540
caagccgcgg cacaggacaa caactttacc agcaactccg ccttcatcac caaaggccaa   600
atttctgggt caaccccaac catccaattc cttccacccc ccgaataa               648
```

<210> SEQ ID NO 3
<211> LENGTH: 211
<212> TYPE: PRT
<213> ORGANISM: Artificial Sequence
<220> FEATURE:
<223> OTHER INFORMATION: CPdeltaN5 PapMV VLP

<400> SEQUENCE: 3

```
Met Ala Ser Thr Pro Asn Ile Ala Phe Pro Ala Ile Thr Gln Glu Gln
 1               5                  10                  15

Met Ser Ser Ile Lys Val Asp Pro Thr Ser Asn Leu Leu Pro Ser Gln
             20                  25                  30

Glu Gln Leu Lys Ser Val Ser Thr Leu Met Val Ala Ala Lys Val Pro
         35                  40                  45

Ala Ala Ser Val Thr Thr Val Ala Leu Glu Leu Val Asn Phe Cys Tyr
     50                  55                  60

Asp Asn Gly Ser Ser Ala Tyr Thr Thr Val Thr Gly Pro Ser Ser Ile
 65                  70                  75                  80

Pro Glu Ile Ser Leu Ala Gln Leu Ala Ser Ile Val Lys Ala Ser Gly
                 85                  90                  95

Thr Ser Leu Arg Lys Phe Cys Arg Tyr Phe Ala Pro Ile Ile Trp Asn
            100                 105                 110

Leu Arg Thr Asp Lys Met Ala Pro Ala Asn Trp Glu Ala Ser Gly Tyr
        115                 120                 125

Lys Pro Ser Ala Lys Phe Ala Ala Phe Asp Phe Asp Gly Val Glu
    130                 135                 140

Asn Pro Ala Ala Met Gln Pro Pro Ser Gly Leu Thr Arg Ser Pro Thr
145                 150                 155                 160

Gln Glu Glu Arg Ile Ala Asn Ala Thr Asn Lys Gln Val His Leu Phe
                165                 170                 175

Gln Ala Ala Ala Gln Asp Asn Asn Phe Ala Ser Asn Ser Ala Phe Ile
            180                 185                 190

Thr Lys Gly Gln Ile Ser Gly Ser Thr Pro Thr Ile Gln Phe Leu Pro
        195                 200                 205

Pro Pro Glu
    210
```

<210> SEQ ID NO 4
<211> LENGTH: 9
<212> TYPE: PRT
<213> ORGANISM: Artificial Sequence -continued

```
<220> FEATURE:
<223> OTHER INFORMATION: gp33 peptide

<400> SEQUENCE: 4

Lys Ala Val Tyr Asn Phe Ala Thr Met
1               5

<210> SEQ ID NO 5
<211> LENGTH: 9
<212> TYPE: PRT
<213> ORGANISM: Artificial Sequence
<220> FEATURE:
<223> OTHER INFORMATION: Modified Gp100 peptide

<400> SEQUENCE: 5

Ile Met Asp Gln Val Pro Phe Ser Val
1               5

<210> SEQ ID NO 6
<211> LENGTH: 30
<212> TYPE: DNA
<213> ORGANISM: Artificial Sequence
<220> FEATURE:
<223> OTHER INFORMATION: Forward CPdeltaN5 Primer

<400> SEQUENCE: 6
agtcccatgg atccaacgtc caatcttctg                                       30

<210> SEQ ID NO 7
<211> LENGTH: 49
<212> TYPE: DNA
<213> ORGANISM: Artificial Sequence
<220> FEATURE:
<223> OTHER INFORMATION: Reverse CPdeltaN5 primer

<400> SEQUENCE: 7
atgcggatcc ttactaatgg tgatggtgat ggtgttcggg gggtggaag                  49

<210> SEQ ID NO 8
<211> LENGTH: 20
<212> TYPE: PRT
<213> ORGANISM: Artificial Sequence
<220> FEATURE:
<223> OTHER INFORMATION: Extended gp33 peptide

<400> SEQUENCE: 8

Thr Ser Gly Gly Gly Lys Ala Val Tyr Asn Phe Ala Thr Cys His His
1               5                   10                  15

His His His His
            20

<210> SEQ ID NO 9
<211> LENGTH: 28
<212> TYPE: PRT
<213> ORGANISM: Artificial Sequence
<220> FEATURE:
<223> OTHER INFORMATION: Modified extended gp33 peptide

<400> SEQUENCE: 9

Thr Ser Gly Gly Gly Thr Ser Ile Lys Ala Val Tyr Asn Phe Ala Thr
1               5                   10                  15

Cys Gly Ile Leu Thr Arg His His His His His His
            20                  25

<210> SEQ ID NO 10
<211> LENGTH: 42
```

```
<212> TYPE: DNA
<213> ORGANISM: Artificial Sequence
<220> FEATURE:
<223> OTHER INFORMATION: Primer

<400> SEQUENCE: 10
gcacaattgg ctagtattgt cgcagcttcc ggcacttccc tt                    42

<210> SEQ ID NO 11
<211> LENGTH: 42
<212> TYPE: DNA
<213> ORGANISM: Artificial Sequence
<220> FEATURE:
<223> OTHER INFORMATION: Primer

<400> SEQUENCE: 11
aagggaagtg ccggaagctg cgacaatact agccaattgt gc                    42

<210> SEQ ID NO 12
<211> LENGTH: 48
<212> TYPE: DNA
<213> ORGANISM: Artificial Sequence
<220> FEATURE:
<223> OTHER INFORMATION: Primer

<400> SEQUENCE: 12
gcttccggca cttcccttgc agcattctgc gcgtacttcg cgccaata              48

<210> SEQ ID NO 13
<211> LENGTH: 48
<212> TYPE: DNA
<213> ORGANISM: Artificial Sequence
<220> FEATURE:
<223> OTHER INFORMATION: Primer

<400> SEQUENCE: 13
tattggcgcg aagtacgcgc agaatgctgc aagggaagtg ccggaagc              48

<210> SEQ ID NO 14
<211> LENGTH: 45
<212> TYPE: DNA
<213> ORGANISM: Artificial Sequence
<220> FEATURE:
<223> OTHER INFORMATION: Primer

<400> SEQUENCE: 14
ataatctgga atctggcgac ggccgcaatg gctcctgcca attgg                 45

<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15
ccaattggca ggagccattg cggccgtcgc cagattccag attat                 45

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
gctcctgcca attgggcggc ttcaggatac aag                              33
```

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
cttgtatcct gaagccgccc aattggcagg agc                           33

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
gcctcaggat acgcaccaag cgccgccttt gccgcgttc                     39

<210> SEQ ID NO 19
<211> LENGTH: 39
<212> TYPE: DNA
<213> ORGANISM: Artificial Sequence
<220> FEATURE:
<223> OTHER INFORMATION: Primer

<400> SEQUENCE: 19
gaacgcggca aaggcggcgc ttggtgcgta tcctgaggc                     39

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
tttgccgcgt tcgccttctt cgccggggtg gagaat                        36

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
attctccacc ccggcgaaga aggcgaacgc ggcaaa                        36

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
ttcttcgacg gggtggcgaa tccggcggcc atg                           33

<210> SEQ ID NO 23
<211> LENGTH: 33
<212> TYPE: DNA
<213> ORGANISM: Artificial Sequence
<220> FEATURE:
<223> OTHER INFORMATION: Primer

```
<400> SEQUENCE: 23
catggccgcc ggattcgcca ccccgtcgaa gaa                          33

<210> SEQ ID NO 24
<211> LENGTH: 45
<212> TYPE: DNA
<213> ORGANISM: Artificial Sequence
<220> FEATURE:
<223> OTHER INFORMATION: Primer

<400> SEQUENCE: 24
caaccccctt cgggactaat cgcgtcgccg acccaggaag agcgg             45

<210> SEQ ID NO 25
<211> LENGTH: 45
<212> TYPE: DNA
<213> ORGANISM: Artificial Sequence
<220> FEATURE:
<223> OTHER INFORMATION: Primer

<400> SEQUENCE: 25
ccgctcttcc tgggtcggcg acgcgattag tcccgaaggg ggttg             45

<210> SEQ ID NO 26
<211> LENGTH: 50
<212> TYPE: DNA
<213> ORGANISM: Artificial Sequence
<220> FEATURE:
<223> OTHER INFORMATION: Primer

<400> SEQUENCE: 26
ctaatcaggt cgccgaccca ggcagcggcg attgccaatg ctaccaacaa        50

<210> SEQ ID NO 27
<211> LENGTH: 51
<212> TYPE: DNA
<213> ORGANISM: Artificial Sequence
<220> FEATURE:
<223> OTHER INFORMATION: Primer

<400> SEQUENCE: 27
tttgttggta gcattggcaa tcgccgctgc ctgggtcggc gacctgatta g      51

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
atcgccatgg catccacacc caacatagcc ttccccgcca tcacc             45

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
atgcggatcc ttactaatgg tgatggtgat ggtgttcggg gggtggaag         49

<210> SEQ ID NO 30
<211> LENGTH: 51
```

```
<212> TYPE: DNA
<213> ORGANISM: Artificial Sequence
<220> FEATURE:
<223> OTHER INFORMATION: Primer

<400> SEQUENCE: 30
ctagtggtgg cggtctgttg ctgaaagcgg tgtataactt tgcgaccatg a          51

<210> SEQ ID NO 31
<211> LENGTH: 51
<212> TYPE: DNA
<213> ORGANISM: Artificial Sequence
<220> FEATURE:
<223> OTHER INFORMATION: Primer

<400> SEQUENCE: 31
cgcgtcatgg tcgcaaagtt ataccgct ttcagcaaca gaccgccacc a             51

<210> SEQ ID NO 32
<211> LENGTH: 63
<212> TYPE: DNA
<213> ORGANISM: Artificial Sequence
<220> FEATURE:
<223> OTHER INFORMATION: Primer

<400> SEQUENCE: 32
ctagttcttc tgcgttcacc atcatggacc aggttccgtt ctctgtttct gtttctcagc  60
tga                                                               63

<210> SEQ ID NO 33
<211> LENGTH: 63
<212> TYPE: DNA
<213> ORGANISM: Artificial Sequence
<220> FEATURE:
<223> OTHER INFORMATION: Primer

<400> SEQUENCE: 33
ctagtcagct gagaaacaga aacagagaac ggaacctggt ccatgatggt gaacgcagaa  60
gaa                                                               63

<210> SEQ ID NO 34
<211> LENGTH: 9
<212> TYPE: PRT
<213> ORGANISM: Artificial Sequence
<220> FEATURE:
<223> OTHER INFORMATION: Gp100 peptide

<400> SEQUENCE: 34

Ile Thr Asp Gln Val Pro Phe Ser Val
 1               5

<210> SEQ ID NO 35
<211> LENGTH: 33
<212> TYPE: DNA
<213> ORGANISM: Artificial Sequence
<220> FEATURE:
<223> OTHER INFORMATION: Primer

<400> SEQUENCE: 35
agtcccatgg catccacacc caacatagcc ttc                              33

<210> SEQ ID NO 36
<211> LENGTH: 79
<212> TYPE: DNA
<213> ORGANISM: Artificial Sequence
<220> FEATURE:
```

```
<223> OTHER INFORMATION: Primer

<400> SEQUENCE: 36
gatcggatcc ttactaatgg tgatggtgat ggtgacgcgt ggtactagtt tcggggggtg      60
gaaggaattg gatggttgg                                                  79

<210> SEQ ID NO 37
<211> LENGTH: 80
<212> TYPE: DNA
<213> ORGANISM: Artificial Sequence
<220> FEATURE:
<223> OTHER INFORMATION: Primer

<400> SEQUENCE: 37
gatcactagt gtggtggtgg gtaccaccga tcgtagcggt gcgccgacct acagctgggg      60
tgcgaacgat acgcgtcatg                                                 80

<210> SEQ ID NO 38
<211> LENGTH: 80
<212> TYPE: DNA
<213> ORGANISM: Artificial Sequence
<220> FEATURE:
<223> OTHER INFORMATION: Primer

<400> SEQUENCE: 38
catgacgcgt atcgttcgca ccccagctgt aggtcggcgc accgctacga tcggtggtac      60
ccaccaccac actagtgatc                                                 80

<210> SEQ ID NO 39
<211> LENGTH: 33
<212> TYPE: DNA
<213> ORGANISM: Artificial Sequence
<220> FEATURE:
<223> OTHER INFORMATION: Primer

<400> SEQUENCE: 39
agtcccatgg ccgatccaac gtccaatctt ctg                                  33

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
acgtccatgg tatatctcct tcttaaag                                        28
```